(12) United States Patent
Belorgey et al.

(10) Patent No.: US 11,345,907 B2
(45) Date of Patent: May 31, 2022

(54) METHOD FOR PRODUCING ALBICANOL COMPOUNDS

(71) Applicant: FIRMENICH SA, Satigny (CH)

(72) Inventors: Didier Belorgey, Shanghai (CN); Xiu-Feng He, Shanghai (CN); Qi Wang, Shanghai (CN); Lily Ji-Xiu Zhang, Shanghai (CN)

(73) Assignee: Firmenich SA, Satigny (CH)

( * ) Notice: Subject to any disclaimer, the term of this patent is extended or adjusted under 35 U.S.C. 154(b) by 0 days.

(21) Appl. No.: 17/059,071

(22) PCT Filed: May 28, 2019

(86) PCT No.: PCT/EP2019/063824
§ 371 (c)(1),
(2) Date: Nov. 25, 2020

(87) PCT Pub. No.: WO2019/229064
PCT Pub. Date: Dec. 5, 2019

(65) Prior Publication Data
US 2021/0254039 A1    Aug. 19, 2021

(30) Foreign Application Priority Data

May 29, 2018   (WO) ................. PCT/CN2018/088902
Aug. 10, 2018  (EP) ..................................... 18188427

(51) Int. Cl.
*C12N 9/88* (2006.01)
*C12P 7/02* (2006.01)
(Continued)

(52) U.S. Cl.
CPC ............ *C12N 9/88* (2013.01); *C12N 9/14* (2013.01); *C12P 5/002* (2013.01); *C12P 5/007* (2013.01);
(Continued)

(58) Field of Classification Search
None
See application file for complete search history.

(56) References Cited

U.S. PATENT DOCUMENTS

2015/0059018 A1   2/2015  Bouwmeester et al.
2018/0208948 A1*  7/2018  Daviet ................. C12Y 402/03
(Continued)

FOREIGN PATENT DOCUMENTS

WO   2013058655 A1   4/2013
WO   2017077125 A1   5/2017

OTHER PUBLICATIONS

International Search Report and Written Opinion for corresponding PCT/EP2019/063824 dated Jan. 27, 2020, 20 pages.
(Continued)

*Primary Examiner* — Richard C Ekstrom
(74) *Attorney, Agent, or Firm* — Armstrong Teasdale LLP

(57) ABSTRACT

Described herein is a method of producing a drimane sesquiterpene, such as an albicanol compound and/or derivatives thereof, by contacting at least one polypeptide with farnesyl diphosphate (FPP) with a polypeptide of the Haloacid dehalogenase-like (HAD-like) hydrolase superfamily as obtainable from plants of the genus *Dryopteris*, in particular of the species *Dryopteris fragrans*. The method may be performed in vitro or in vivo. Also described herein are amino acid sequences of polypeptides useful in the methods and nucleic acids encoding the polypeptides described. Also described herein are host cells or organisms genetically modified to express the polypeptides and useful to produce a drimane sesquiterpene such as an albicanol compound.

8 Claims, 20 Drawing Sheets
Specification includes a Sequence Listing.

drimane structure (+)-albicanol (−)-drimenol

(51) Int. Cl.
*C12P 5/00* (2006.01)
*C12N 9/14* (2006.01)

(52) U.S. Cl.
CPC .............. *C12P 7/02* (2013.01); *C12Y 301/07* (2013.01); *C12Y 301/07007* (2013.01)

(56) References Cited

U.S. PATENT DOCUMENTS

| | | | |
|---|---|---|---|
| 2018/0251797 A1* | 9/2018 | Zhang | C12P 7/04 |
| 2019/0093131 A1 | 3/2019 | Liu et al. | |
| 2020/0056210 A1* | 2/2020 | Li | C12N 9/88 |
| 2020/0140898 A1* | 5/2020 | Schalk | C12P 7/02 |
| 2021/0254039 A1* | 8/2021 | Belorgey | C12N 9/14 |

OTHER PUBLICATIONS

Anonymous, "UPI0005E78528", Mar. 28, 2015 (Mar. 28, 2015), Retrieved from the Internet: URL:https://www.uniprot.org/uniparc/UPI0005E78528 XP055562918.

Anonymous, "UPI0009C53597", Apr. 6, 2017 (Apr. 6, 2017), Retrieved from the Internet: URL:https://www.uniprot.org/uniparc/UPI0009C53597XP055562921.

* cited by examiner

Fig. 1
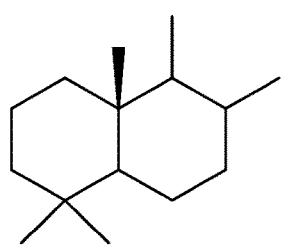
drimane structure
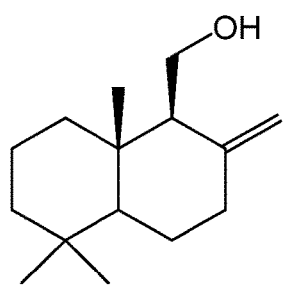
(+)-albicanol
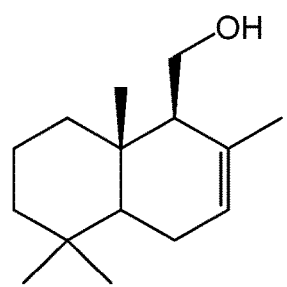
(-)-drimenol

Fig. 9A

| | | | | |
|---|---|---|---|---|
| DfHAD | | | ---MEFSASAPPPR | LASVILLEPL 21 |
| DfHAD-9(V274A) | | | ---MEFSASAPPPR | LASVILLEPL 21 |
| DfHAD-8(K532R) | | | ---MEFSASAPPPR | LASVILLEPL 21 |
| CvTps1 | | | -------MTTIHRRH | TTLILDLGDV 18 |
| LoTps1 | | | ----------MY | TALILDLGDV 12 |
| OCH93767.1 | | | -------MSAAVRY | TTTLILDLGDV 17 |
| EMD37666.1 | | | -------MSAAAQY | TTTLILDLGDV 17 |
| EMD37666-8 | | | -------MSAAAQY | TTTLILDLGDV 17 |
| XP_001217376.1 | | | -------MAITKGPV | KALILDFSNV 18 |
| OJJ98394.1 | | | -------MPSV | KALVLDFAGV 14 |
| GAO87501.1 | | | ------MTRQKSPQY | KAIIFDLGDV 19 |
| XP_008034151.1 | | | -------MASPHRRY | TTLILDLGDV 18 |
| XP_007369631.1 | | | -------MASIHRRY | TTLILDLGDV 18 |
| ACQ026372 | MRRNVLNKAT | HSQSPLKPNI | ------MV | RALILDLGDV 30 |
| KIA75676.1 | | | ----------MV | QAIIFDLGGV 12 |
| XP_001820867.2 | | | ------MTRWKSSQY | RALILDLGDV 19 |
| CEN60542.1 | | | ----------MV | SNLILD1GDV 12 |
| XP_009547469.1 | | | -------MSMIPRC | NALIFDLGDV 17 |
| KLO09124.1 | MSIHGSSMSS YSSTVPSMTS SPASTSTPSS PASSIHEIGP | VPEARRKGQC | NALIFDLGDV 60 |
| OJI95797.1 | | | ---------MGST | KALVVDFGNV 14 |

Fig. 9B

```
                                                                                                    120
                                                                                                     |
DfHAD          GFLLTPHY-S SQLPKKLLRR LLCTRIWHRY QRGRLRLRDA AMLLAQLPFL AVSDHPWALD  80
DfHAD-9(V274A) GFLLTPHY-S SQLPKKLLRR LLCTRIWHRY QRGRLRLRDA AMLLAQLPFL AVSDHPWALD  80
DfHAD-8(K532R) GFLLTPHY-S SQLPKKLLRR LLCTRIWHRY QRGRLRLRDA AMLLAQLPFL AVSDHPWALD  80
CvTpsl         LFRWSPKT-E TAIPPROLKE ILTSVTWFEY ERGQISQTE- CYERCAAEFK VDPLVIAEAF  76
LoTpsl         LFSWSTT-N TTIPPROLKE ILSSPAWFEY ERGRITQAE- CYERVSAEFS LDATAVAEAF  70
OCH93767.1     LFTWSPKT-K TSISPRTLKE ILNSATWYEY ERGSITQHE- CYERVGVEFG IAPSEIHNAF  75
EMD37666.1     LFTWSPKT-K TSISPRTLKE ILNSATWYEY ERGRISQDE- CYERVGTEFG IAPSEIDNAF  75
EMD37666-B     LFTWSPKT-K TSIPPRTLKE ILNSATWYEY ERGRISQDE- CYERVGTEFG IAPSEIDNAF  75
XP_001217376.1 LCSWKPPS-N VAVPPO-LKM IMSSOIWHDY ECCGRYSRED- CYARVADRFH ISAADMEDTL  76
OJJ98394.1     LCSWTPPA-E SPLSPAQLKQ LMSSEIWFEY ERGRYSEEE- CYAKLVERFS ISAADMASTM  72
GAO87501.1     FFTWDAPK-D TAVLPNLFKK MLTSPTWSDY ERGKLSEES- CYERLAEQFD VDSSEIARSL  77
XP_008034151.1 LFSWSSKT-N TPIPPKKLKE ILSSLTWFEY ERGRVSSEFS LDAATIAEAF  76
XP_007369631.1 LFRWSPKT-E TAIPPQOLKD ILSSVTWFEY ERGRCAEEFK IEASVIAEAF  76
ACgO06372      LLTWSDSTPK SPLPPKIVKG ILRSLTWFEY EKGNLTESQ- TYGQVAQEFG VDASEVKASF  89
KIA75676.1     LFNWDAPK-S TPVSRKTLSQ MLHSDIWGEY ECGOLTEPE- SYKALASRYS CQAQDVADTF  70
XP_001820086.2 -LTWDLPE-D TVISAQ-FKR MLTSQTWSDY ERGNLSENG- CYQRLAEDFG IDSADIAHTV  77
CEN60542.1     LFNWDAPA-S TPISRKTLGO MLHSEIWGEY ERGHLTEDE- AYNALAKRYS CEAKDVAHTF  70
XP_009547469.1 LFTWSPKT-S TSISPRTMKS ILSSTTWHQY ETGHISOGD- CYRLIGNQFS IDPQEVGLAF  75
KLO09124.1     LFTWSAET-K TTISPKLLKK EKGNIGEQE- AYDAVAKEFG VPSSEVGAAF 118
OJJ95797.1     LCTWTPPR-E LSIPPKKLKQ IMSSDIWLDY ERGIYKSEDE CYLAVATRFG VSPSDLSSVM  73
```

Fig. 9C

```
                                        140                    160
                                          |                      |
       DfHAD  NLASLLRPTA VRAVPWMLLL LDFLRDELHL KVVCATNSSP EELQELRHQF PALFAKVDAT 140
DfHAD-9(V274A) NLASLLRPTA VRAVPWMLLL LDFLRDELHL KVVCATNSSP EELQELRHQF PALFAKVDAT 140
DfHAD-8(K532R) NLASLLRPTA VRAVPWMLLL LDFLRDELHL KVVCATNSSP EELQELRHQF PALFAKVDAT 140
       CvTps1 KQARESLRPN KAFIALIREL RHQMHGDLTV LALSNISLPD YEYIMSLS-- SDWATVFNRV 134
       LoTps1 RQARDSLRPN QKFLTLIREL RQQSHGELTV FALSNISLPD YEFIMALD-- SKWTSVFDRV 128
    OCH93767.1 KQARDSMESN DELIALVREL KEOSDGELLV FALSNISLPD YEYVLTKP-- ADWS-IFDKV 132
    EMD37666.1 KQARDSMESN DELIALVREL KTQLDGELLV FALSNISLPD YEYVLTKP-- ADWS-IFDKV 132
    EMD37666.0 KQARDSMESN DELIALVREL KTQLDGELLV FALSNISLPD YEYVLTKP-- ADWS-IFDKV 132
XP_001217376.1 KQARKSLQVH HETLLFLQQY KKDAGGELMV CGMTNTPRPE QDVMHSIN-- AEYP-VFDRI 133
    OJJ98394.1 EQARQSLELN HAVLQLVSEI RKRNPG-LKV YGMTNTPHAE QDCVNRIV-- NSYP-VFDHV 128
    GAO87501.1 RKAQQSLTTD AAIVSLISEI R-ALAGHIAI YAMSNISAPA YAAVLQTQ-- PEMG-IFDGV 133
XP_008034151.1 QQARDSLRPN EEFLALIREL RQQTHGQLTV LALSNISLPD YEYIMALO-- SDWTSVFDRV 134
XP_007369631.1 KQARGSLRPN EEFIALIRDL RREMHGDLTV LALSNISLPD YEYIMSLS-- SDWTTVFDRV 134
    ACG06372 EAARDSLKSN PMLLQLIRSL K--DSGHVI YAMSNISAPD WEFLKTRADL SDWA-LFDRV 145
    KIA75676.1 YLARESLRLD ATFKTFLQDL KQRANGSLRV YGMSNISQPD YEVILLSKA- DDLS-LFDKI 127
XP_001820867.2 RQARESLVTD TAIMNISEI R-AGANHIAI FAMSNISOPD YAALLLDH-- RGMC-SFDRV 133
    CEN60542.1 VLARESLRLD TKFKTFLQTL KQNANGSLRV YGMSNISKPD FEVLLGKA-- DDWT-LFDKI 127
XP_009547469.1 QQARDSLQPN VDFIHFIRAL KAESHGTLRV FAMSNISQPD YAVLRTKD-- ADWA-VFDDI 132
    KLO09124.1 OCARDSLOSN PRLVSLIREL KS--QYDLKV YAMSNISAPD WEVLRTKATP EEWA-MFDRV 175
    OJJ957797.1 KKARESLQPN TATLNHLSHL KKTQPG-LRI YGLTNTPLPE QSSVRSIA-- QEWP-IFDHI 129
```

| | | | | | | | |
|---|---|---|---|---|---|---|---|
| | | 260 | | 280 | | 300 | |
| DfHAD | DELTARASSG | QLRDAQLIRR | IVCAMHGPAV | SAVVSGSITS | SGPQTAKIEE | LPTAADSHLR | 260 |
| DfHAD-9(V274A) | DELTARASSG | QLRDAQLIRR | IVCAMHGPAV | SAVVSGSITS | SGPQTAKIEE | LPTAADSHLR | 260 |
| DfHAD-8(K532R) | DELTARASSG | QLRDAQLIRR | IVCAMHGPAV | SAVVSGSITS | SGPQTAKIEE | LPTAADSHLR | 260 |
| CvTps1 | ---------- | --NEANVFRQ | LRNIFGNPVS | RGQGYLRKHA | G--------- | ---------- | 217 |
| LgTps1 | ---------- | --SQDNVFRM | LRNIFGDPIH | RGRDYLRQHA | G--------- | ---------- | 211 |
| OCH93767.1 | ---------- | --KHEDVMRA | LRNIFGDPVR | RGREYLRRNA | R--------- | ---------- | 215 |
| EMD37666.1 | ---------- | --KQEDVMRA | LRNIFGDPVR | RGREYLRRNA | M--------- | ---------- | 215 |
| EMD37666-B | ---------- | --KQEDVMRA | LRNIFGDPVR | RGREYLRRNA | M--------- | ---------- | 215 |
| XP_001217376.1 | ---------- | --SQQDLRRV | VLNFLGDPVH | RGLQFLAANA | K--------- | ---------- | 216 |
| OJJ98394.1 | ---------- | --NVTDFKQQ | IINVTGDPVS | RGLRYLRSNA | K--------- | ---------- | 211 |
| GAO87501.1 | ---------- | --GAGELSRQ | LRNLVLOPVQ | RGREFLRRNA | G--------- | ---------- | 216 |
| XP_008034151.1 | ---------- | --SQENVFQT | LRNIFGDPIH | RGRDYLRRHA | G--------- | ---------- | 217 |
| XP_007369031.1 | ---------- | --NOANVFRQ | LKNIFGDPIR | RGQEYLRGHA | G--------- | ---------- | 217 |
| ACg006372 | ---------- | --DINNVIRQ | LKNLCEDPIH | RARSFLYANK | T--------- | ---------- | 228 |
| KJA75676.1 | ---------- | --DKEDVQRQ | LRNLFGSPAE | RGREYLSINK | T--------- | ---------- | 210 |
| XP_001820867.2 | ---------- | --NAAELGRQ | LRNLIFDPVE | RGREFLRRNA | G--------- | ---------- | 216 |
| CEN60542.1 | ---------- | --KKDEVQRQ | LTNIFGSPAE | RGLEYLSANK | T--------- | ---------- | 210 |
| XP_009547469.1 | ---------- | --SMDNVKRA | LRYLISDPIR | RGREFLQARA | G--------- | ---------- | 215 |
| KL009124.1 | ---------- | --SFENVARQ | LKNYVADPIG | RAEAWLRDNA | K--------- | ---------- | 258 |
| OJJ95797.1 | ---------- | --SHDQLSRQ | LGNVLGDPIQ | RGHNFLLSNA | K--------- | ---------- | 212 |

Fig. 9F

| | | | 320 | | | 340 | | | 360 | |
|---|---|---|---|---|---|---|---|---|---|---|
| DfHAD | SAALTSAQQF | FLKVIAPHRP | EKPFVQLPSL | TSEGIRIYDT | FAQFVIADLL | DDTRFLPMQS | 320 |
| DfHAD-9(V274A) | SAALTSAQQF | FLKAIAPHRP | EKPFVQLPSL | TSEGIRIYDT | FAQFVIADLL | DDTRFLPMQS | 320 |
| DfHAD-8(K532R) | SAALTSAQQF | FLKVIAPHRP | EKPFVQLPSL | TSEGIRIYDT | FAQFVIADLL | DDTRFLPMQS | 320 |
| CvTps1 | - | - | - | - | - | - | - | - | - | - | - | - | - | - | - | KLESS | TDNGLTFEEN | FTQLIIYEVT | QDRSLIFTLSE | 252 |
| LoTps1 | - | - | - | - | - | - | - | - | - | - | - | - | - | - | - | RLETS- | TDAGVVFEEN | FTQLLILELT | NDKSLVTLPD | 246 |
| OCH93767.1 | - | - | - | - | - | - | - | - | - | - | - | - | - | - | - | KLESI- | TDHGVAFGEN | FTQLLILELT | SDASLVTLPD | 250 |
| EMD37666.1 | - | - | - | - | - | - | - | - | - | - | - | - | - | - | - | RLESV- | TDHGVAFGEN | FTQLLILELT | NDPSLVTLPD | 250 |
| EMD37666-B | - | - | - | - | - | - | - | - | - | - | - | - | - | - | - | RLESV- | TDHGVAFGEN | FTQLLILELA | NDPSLVTLPD | 250 |
| XP_001217376.1 | - | - | - | - | - | - | - | - | - | - | - | - | - | - | - | KMDSV- | TNTGDTIQDN | FAQLLILELT | QDRELVKLQA | 251 |
| OJI98394.1 | - | - | - | - | - | - | - | - | - | - | - | - | - | - | - | SLLTV- | TSNNSVIHEN | FAQLLILELT | GDRDLIELEP | 246 |
| GAO87501.1 | - | - | - | - | - | - | - | - | - | - | - | - | - | - | - | ALYSI- | CETGQVIREN | FSQLLIIYELT | GDRSLVNLEY | 251 |
| XP_008034151.1 | - | - | - | - | - | - | - | - | - | - | - | - | - | - | - | RLETS- | TDAGVVFEEN | FTQLIIYELT | NDKSLITTSQ | 252 |
| XP_007369631.1 | - | - | - | - | - | - | - | - | - | - | - | - | - | - | - | KLESS- | TDNGLIFEEN | FSQLLILEAI | QDESLVDFVR | 252 |
| ACG06372 | - | - | - | - | - | - | - | - | - | - | - | - | - | - | - | CLNTV- | STDGTIVSEN | FGQLLILEAT | RDPDLVSMHP | 263 |
| KJA75676.1 | - | - | - | - | - | - | - | - | - | - | - | - | - | - | - | KLQSV- | TTTNIPILDN | FSQLLILEAT | GDKSLVSLEY | 245 |
| XP_001820867.2 | - | - | - | - | - | - | - | - | - | - | - | - | - | - | - | EFHSI- | TETDQIVREN | FGQLLILEAT | EDPSLVRMEP | 251 |
| CEN60542.1 | - | - | - | - | - | - | - | - | - | - | - | - | - | - | - | NLQSA- | TTTDIPIQDN | FAQLLILEAT | KDRTLVNYMD | 245 |
| XP_009547469.1 | - | - | - | - | - | - | - | - | - | - | - | - | - | - | - | HLESE- | TNTGIEIGDN | FAQLLILEAT | KDRTLVNYMD | 250 |
| KLO09124.1 | - | - | - | - | - | - | - | - | - | - | - | - | - | - | - | KMLSI- | TDAGVVYEN | FGQMLILEAT | GDRSLVDYVE | 293 |
| OJI57797.1 | - | - | - | - | - | - | - | - | - | - | - | - | - | - | - | QMNST- | TDKGVIIRDN | FAQLLILELT | QNPDLVALET | 247 |

```
                         440↓                                    480↓
DfHAD            FGKVDKDTLN KVLDRMLEQV SEDDGILQVY FDVERPRIDP VVVANTVFLF HLGKRGHEVA 440
DfHAD-9(V274A)   FGKVDKDTLN KVLDRMLEQV SEDDGILQVY FDVERPRIDP VVVANTVFLF HLGKRGHEVA 440
DfHAD-8(K532R)   FGKVDKDTLN KVLDRMLEQV SEDDGILQVY FDVERPRIDP VVVANTVFLF HLGKRGHEVA 440
CvTps1           ---PDRALVD SILDQMLEYV DAD-GIMQTY FDSSRPRIDP FVCVNVLSLF YANGRGRELP 341
LoTps1           ---LDHALVN SVLDEMLKYV DAD-GIMQTY FDHTRPRMDP FVCVNVLSLF HEQGRGHELP 335
OCH93767.1       ---RDAATVS SVMDEMLKYR DAD-GIMQTY FDNGRQRLDP FVNANVLTFF YANGRGHELD 339
EMD37666.1       ---RDPGVIS SVMDEMLNYR RDPGVIS SVMDEMLNYR DPPG-GIMQTY FDDGRQRLDP FVNVNVLTFF YTNGRGHELD 345
EMD37666-B       ---RDPGVIS SVMDEMLNYR DPD-GIMQTY FDDGRQRLDP FVNVNVLTFF YTNGRGHELD 339
XP_001217376.1   ---VAEDVVS SVLDEMLKFV TDD-GIFMTY FDSSRPRVDP VVCINVLGVF CAHNRERDVL 341
QJJ98394.1       ---IHKQVVA DVMDEIMLLL OND-GIVPTY FDPTRPRVDP VVCVNVLSLF AQNGRESELL 336
GAO87501.1       ---ADDNTVN SVLGEISEVA NDE-GIVNTY FDQTRQRIDP AVCVNVLRLF YTYGRGATLP 341
XP_008034151.1   ---PPRTLVN SILDEMLEYV DAD-GIMQTY FDHSRPRMDP FVCVNVLSLF YEYGRGQDLP 341
XP_007369631.1   ---PDRALVN SVLDEMLEYV DAD-GIMQTY FDRSRPRVDP FVCVNVLSLF YENGRGHELP 341
ACg006372        ---IDDKTRN RVMDEILAYQ SED-GIVLVY FDHKRPRIDP VVCVNVLTLF YRYGRGHQLQ 355
KIA75676.1       ---PSPEIAA SVMDEIVTRL NKD-GIVPTY FDSTRPRVDP IVCVNVLTTF AKYGREDELS 335
XP_001820867.2   ---TDTKTAN LLLDQILGLV NAD-EIVTTY FDQTRPRVDP VVCVNVLSMF CTYGRGIALP 341
CEN60542.1       ---TSPDVVN SVIDEIISRR DKD-GIVPTY FDNTRPRVDP IVCVNVLSLF AKYGREHDLP 335
XP_009547469.1   ---RDDGTAN LVMDEMLQYR DED-GIIQTY FDHERPRIDP IVCVNVLTFF YSRGRGSELA 340
KLO09124.1       ---VDEKTRH SVMDEMLTYK NED-GIIATY FDATRPRIDP VVCANVLTFF YKNGRGEELN 384
QJJ95797.1       ---VDKEVVW SVMDEMLTFT NAD-GIFMTY FDRSRPRVDP VVCTNVLNLF CMHGRESEVA 337
```

Fig. 9I

```
                                    500                  520                        540
DfHAD          RSEKFVESVL LQRAYEEGTL YYNLGEAFLV SVARLVHEFK EHFTRSGMRR ALEERLRERA 500
DfHAD-9(V274A) RSEKFVESVL LQRAYEEGTL YYNLGEAFLV SVARLVHEFK EHFTRSGMRR ALEERLRERA 500
DfHAD-8(K532R) RSEKFVESVL LQRAYEEGTL YYNLGEAFLV SVARLVHEFK EHFTRSGMRR ALEERLRERA 500
CvTps1         NTLEWYEVL  LHRAYHGGSR YYLSPDCFLF FMSRLLKRAN DSALQARFRP LFMERVKERV 401
LoTps1         NTLEWVHEVL LHRAYIGGSR YYLSADCFLY F-ISRLFACTS DPVLHHQLKP LF-IERVHERV 395
OCH93767.1     QSLSWVREVL LYRAYLGGSR YYPSADCFLY F-ISRLFACTN DPVLHHQLKP LFVERVHERV 399
EMD37666.1     QCLTWVREVL LYRAYLGGSR YYPSADCFLY F-ISRLFACTN DPVLHHQLKP LFVERVQEQI- 405
EMD37666-B     QCLTWVREVL LYRAYLGGSR YYPSPOLFLF FLARLCLAVR NQSLREQLVL PLVDRLRERV 399
XP_001217376.1 PTFHWIRDIIL INRAYLSGTR YYISPDAFLY FLARLSVFLR MSPLRARLMP LLEERVYERI 401
OJJ98394.1     ATFNWVLDVL RHRAHLHGTR YYSPEVFLY FVSQLCRFSK REPTLQLLET LLTDRLKERI 396
GAO87501.1     LTLQWVSDVL EHRAHLHGTR YYMSADCFLF FMSRLLQRIT DPAVLNRLRP LFVERMHERV 401
XP_008034151.1 KTLEWVYEVL LHRAYHGGSR YYLSPDCFLF FMSRLLKRAD DPAVQARLRP LFVERVNERV 401
XP_007369631.1 RTLDWVYEVL INRACASGTF YYATEEQFLF FLSRLIQSS- -PDVRQRLEG VFKRRVVERF 413
ACg006372     KTLDWVEQVL YHRAYLAGTR YYASPEAFLF LLSQRLQERN 395
KIA75676.1     GTIAWVRDVL AHRAYINGTR YYTSPESFLY GVLALRPLET LLIDRLKERL 401
XP_001820867.2 LTLQWVYDVL YHRAYLGGTR YYGSAEAFLF FFTRAFVRNLR PGTLKQDLHA LLSERVRERL 395
CEN60542.1     ATVAWVRDVL YHRAYLDGTR YYETGECFLF DAALHASLKS LFAERVKERI 400
XP_009547469.1 PTLEWVRGVL KHRAYLDGTR YYFGSDTFLF -PSVYARFAP VFQERVKERM 442
KLO09124.1     ETLDWVYDIL LHRAYLDGTR YYSSPDCFLY  397
OJJ95797.1     ATFDWVLDVL RNSAYLSGSR  DGTRRRELKS LLKQQVSQRI
```

Fig. 9J

```
DfHAD          RAGMQERDDA LALAMRIRAC ALCGLAGEGL TKAAEQELLR LQCKSKGCWG CHPFYRNGSN 560
DfHAD-9(V274A) RAGMQERDDA LALAMRIRAC ALCGLAGEGL TKAAEQELLR LQCKSKGCWG CHPFYRNGSN 560
DfHAD-8(K532R) RAGMQERDDA LALAMRIRAC ALCGLAGEGL TRAAEQELLR LQCKSKGCWG CHPFYRNGSN 560
CvTps1         GAAG-----DS MDLAFRILAA ATIGVH---C PQD-LERLAA AQCED-GGWD MCWFYAFGS- 451
LoTps1         GATG-----DS IDLAFRILAA STVGIQ---C PRD-LESLLA WQCED-GGWD LCWFYQYGS- 445
OCH93767.1     GVQG-----DA LELAFRLLVC ASFNIS---N QPD-MRKLLE WQCQD-GGWE GGNLYRFGT- 449
EMD37666.1     GVEG-----DA LELAFRLLVC ASLDVQ---N AID-MRALLE WQCED-GGWE GGNLYRFGT- 455
EMD37666-B     GVEG-----DA LELAFRLLVC ASLDVQ---N AID-MRALLE WQCED-GGWE GGNLYRFGT- 449
XP_001217376.1 GAPG-----EA VSLAARILAC RSFGID---S ARQ-MDSLRG WQCED-GGWE VEWVYRFAS- 451
OJJ98394.1     GAHG-----DA ISLAMRIYTC KLLGMS---- MLD-ERALRD WQCED-GGFP TSWVYRFGS- 446
GAO87501.1     QVKA-----DT LSLAMRILAC LSVGIS---Q VEVDVRELLA WQCKD-GSWE PGSFYRFGS- 452
XP_008034151.1 SAPG-----DS MELAFRILAG SSVGIQ---F PRD-LEKLLA AQCAD-GGWD LCWFYQYGS- 451
XP_007369631.1 GAAG-----DS MDLAFRILAA ASVGLY---C PRD-LERLTA CQCDD-GGWD LCWFYVFGS- 451
ACg006372      GADG-----DA LAMAMRIHTA ASVGLY---D HVD-LDKLFA LQQND-GSWR DSAFYRFPS- 463
KIA75676.1     KTPV-----DA LALSMRIIAC LTLGIE---S PADDVATLTG WQCGD-GGWP ACVIYKYGA- 446
XP_001820867.2 QVKA-----DP LSLAMRILTC LSVGVS---Q VEVDLRELLS WQCED-GSWE HCPFTRYGL- 452
CEN60542.1     NTPV-----DA LALSMRIQAC HALGFD---A PAD-IATLIT WQDED-GGWA AAVIYKYGA- 445
XP_009547469.1 GAPG-----DA LALAMRILAC AAVGVR---D EID-LRSLLP LQCED-GGWE AGWYKYGS- 450
KLO09124.1     GATG-----DA MSLAMRIIAA ATVKIQ---D RVD-CDALLQ TQEDD-GGFP IGWMYKYGA- 492
OJJ95797.1     GADG-----DS VSLATRLLAS NILGIT---N GRD-RSRLLA LQETD-GGWP AGWVYKFGS- 447
```

Fig. 9K

```
                                     620                  640                  660
                                      |                    |                    |
DfHAD            VLSWIGSEAL TTAYAIAALQ PIDI-- ---------- ---------- ---------- ---------- 584
DfHAD-9(V274A)   VLSWIGSEAL TTAYAIAALQ PIDI-- ---------- ---------- ---------- ---------- 584
DfHAD-8(K532R)   VLSWIGSEAL TTAYAIAALQ PIDI-- ---------- ---------- ---------- ---------- 584
CvTps1           TGIKAGNRGL TTALAVAAIR TAL--- ---------- -G- RPPSPSPSNI SSSS------ 489
LoTps1           TGVKAGNRGL TTALAIKAID SAI--- ---------- -A- RPPSPALSVA SSS------- 482
OCH93767.1       TGLKVTNRGL TTAAAVQAIE ATQ--- ---------- -L- RPPSPAFSVE SPKSPVTPVT 493
EMD37666.1       TGLKVTNRGL TTAAAVQAIE ASQ--- ---------- -R- RPPSPSPSVE STKSPITPVT 499
EMD37666-B       TGLKVTNRGL TTAAAVQAIE ASQ--- ---------- --- RPPSPSPSVE STKSPITPVT 493
XP_001217376.1   FGLNVGNRGL ATAFAVRALE ------ ---------- -R- SPYG-ESAVK ---------- 480
OJJ98394.1       TGVKIGNRGL TTALAIKAIE ------ ---------- --- MPLASLWKSW G--------- 477
GAO87501.1       SKMNVGNRGL TTALATRAVE ------ ---------- --- LYQGTRIRSK GTE------- 485
XP_008034151.1   TGVKAGNRGL TTALAIKAIE SAI--- ---------- -A- RPPSPALSAV SSS------- 488
XP_007369631.1   TGVKAGNRGL TTALAVTAIQ TAI--- ---------- -G- RPPSPSPSAA SSSF------ 489
ACg006372        ARQLASNDGL TTAIAIQAIQ AAE--- ---------- -R- LREDGNVL-- ---------- 495
KIA75676.1       GGLGITNRGV STAFAVKAIT TTPLAVQPEV SVSAGAGGSS RPVGADAAAV SLRPRWRAVV 506
XP_001820867.2   SKVSIGNRGL TTAFVVKAVE ------ ---------- --- MCRGS----- ARR------- 477
CEN60542.1       GGLGITNRGV STAFVKAIT GSPVKTETNI G--------GDGA RAVSAMSSLE SRVSRHSEVA 493
XP_009547469.1   SGVKIGNRGL TTALALNAIE AVE--- ---------- -G- RRTRPKSGKI ---------- 494
KLO09124.1       TGMLLGNKGL STALAIQAIK AVE--- ---------- --S FP-------- ---------- 518
OJI95797.1       SGVQIGNRGL STALALKSIE ------ ---------- --- RQKGPVEAIS SEPEAWWPSL 487
```

Fig. 9L

| | | | | | |
|---|---|---|---|---|---|
| DfHAD | | | | | |
| DfHAD-9(V274A) | | | | | |
| DfHAD-8(K532R) | | | | | |
| CvTps1 | -KLDAPNSFL | GIPRPTSPIR | FGELFRSWRK | N-KPTAKSQ- | 584 |
| LoTps1 | -KSEIPKPIQ | RSLRPLSPRR | FGGFLMPWRR | SQRNGVAVSS | 584 |
| OCH93767.1 | PMLEIPALGL | SISRPSSP-L | LGYFKLPWKK | SAEVH---- | 526 |
| EMD37666.1 | PMLEVPSLGL | SISRPSSP-L | LGYFRLPWKK | SAEVH---- | 521 |
| EMD37666.8 | PMLEVPSLGL | SISRPSSP-L | LGYFRLPWKK | SAEVH---- | 527 |
| XP_001217376.1 | -VMRRIV- | | | | 533 |
| OJJ98394.1 | -LTTDIR- | | | | 527 |
| GAO87501.1 | | | | | 486 |
| XP_008034151.1 | -KLEVPKPIL- | Q--RPLSPRR | LGDFLMPWRR | AQR-EVAVSS | 483 |
| XP_007369631.1 | -RPSSPYKFL | GISRPASPIR | FGDLLRPWRK | MSRSNLKSQ- | 485 |
| ACg006372 | | | | | 524 |
| KIA75676.1 | QSLHPLSRVG | GLVAVIFAAL | HFNLAWLYNV | SLASRIV--- | 527 |
| XP_001820867.2 | --LQPISSVG | DWVRFIIASL | HVHLAWLWNV | LLLSKVV--- | 495 |
| CEN60542.1 | AAPRSSTSSH | RSNRSISRTF | QAYFKASWTS | MKQVAVA--- | 543 |
| XP_009547469.1 | | | | | 477 |
| KLO09124.1 | | | | | 528 |
| OJJ95797.1 | -RLDRLLNVW | PFIDWKGYSP | S--------- | | 531 |
| | | | | | 518 |
| | | | | | 507 |

Fig.10

| Residue number (based on DfHAD) | 174 | 175/176 | 177 | 178 | 179 | 180 | 366 | 367 | 368 | 369 | functional albicanol synthase |
|---|---|---|---|---|---|---|---|---|---|---|---|
| DfHAD | D | SF | D | S | L | E | H | D | L | D |  |
| DfHAD(E180D) | D | SF | D | S | L | D | H | D | L | D | 85% activity lost |
| DfHAD(H366D) | D | SF | D | S | L | E | D | D | L | D | 47% activity lost |
| DfHAD(E180D/H366D) | D | SF | D | S | L | D | D | D | L | D | 99% activity lost |
| DfHAD-Del | D | - | D | S | L | E | H | D | L | D | 90% activity lost |
| DfHAD-Del(E180D) | D | - | D | S | L | D | H | D | L | D | 100% activity lost |
| DfHAD-Del(H366D) | D | - | D | S | L | E | D | D | L | D | 100% activity lost |
| DfHAD-Del(E180D/H366D) | D | - | D | S | L | D | D | D | L | D | 100% activity lost |
| DfHAD-Del(E180D/S178K) | D | - | D | K | L | D | H | D | L | D | 100% activity lost |
| DfHAD-Del(H366D/S178K) | D | - | D | K | L | E | D | D | L | D | 100% activity lost |
| DfHAD-Del(E180D/H336D/S178K) | D | - | D | K | L | D | D | D | L | D | 100% activity lost |
| DfHAD-Del(E180D/H366D/S178K/L368V) | D | - | D | K | L | D | D | D | V | D | 100% activity lost |

SEQUENCE LISTING

<160> NUMBER OF SEQ ID NOS: 29

<210> SEQ ID NO 1
<211> LENGTH: 1755
<212> TYPE: DNA
<213> ORGANISM: Dryopteris fragrans
<220> FEATURE:
<221> NAME/KEY: CDS
<222> LOCATION: (1)..(1755)

<400> SEQUENCE: 1

```
atg gag ttc tct gcc tct gct cct cct cct agg cta gcc agt gtc ata      48
Met Glu Phe Ser Ala Ser Ala Pro Pro Pro Arg Leu Ala Ser Val Ile
1               5                   10                  15 ata ttg gag cct ctc ggc ttc ctc ctc aca cca cac tac tcc tct cag      96
Ile Leu Glu Pro Leu Gly Phe Leu Leu Thr Pro His Tyr Ser Ser Gln
                20                  25                  30 ctt ccc aaa aag ctg ctc cgt cgc ctg ttg tgc act aga atc tgg cac     144
Leu Pro Lys Lys Leu Leu Arg Arg Leu Leu Cys Thr Arg Ile Trp His
            35                  40                  45 agg tat cag cga ggc cgc ctt cgc ctg cgt gac gct gct atg ctg ctc     192
Arg Tyr Gln Arg Gly Arg Leu Arg Leu Arg Asp Ala Ala Met Leu Leu
        50                  55                  60 gcc cag ctc cca ttc cta gct gtg tct gat cac ccc tgg gct ctg gac     240
Ala Gln Leu Pro Phe Leu Ala Val Ser Asp His Pro Trp Ala Leu Asp
65                  70                  75                  80 aat ctc gca agc ctg ctc cgc ccc aca gct gtg cgt gcg gtg cca tgg     288
Asn Leu Ala Ser Leu Leu Arg Pro Thr Ala Val Arg Ala Val Pro Trp
                85                  90                  95 atg ctg ctg ctg ctc gac ttc cta cga gac gag ctc cat ctg aag gta     336
```

-continued

```
                Met Leu Leu Leu Leu Asp Phe Leu Arg Asp Glu Leu His Leu Lys Val
                                100             105             110 gtc tgc gcg acc aac tcc tcc cca gaa gag ctg caa gag ctg cgc cac        384
Val Cys Ala Thr Asn Ser Ser Pro Glu Glu Leu Gln Glu Leu Arg His
            115                 120                 125 cag ttt ccg gcc ctc ttt gcc aag gtc gat gcc acc gtt tct tca ggc        432
Gln Phe Pro Ala Leu Phe Ala Lys Val Asp Ala Thr Val Ser Ser Gly
130                 135                 140 gag gag ggc gtg ggc aag ccg tcc gtg cgc ttc ctg cag gct gcg ttg        480
Glu Glu Gly Val Gly Lys Pro Ser Val Arg Phe Leu Gln Ala Ala Leu
145                 150                 155                 160 gac aaa gcc ggt gtc cac gcg cag caa acc ttg tat ctt gac tct ttt        528
Asp Lys Ala Gly Val His Ala Gln Gln Thr Leu Tyr Leu Asp Ser Phe
                165                 170                 175 gac agc ttg gag acc atc atg gct gca cgc tct ctt ggc atg cat gca        576
Asp Ser Leu Glu Thr Ile Met Ala Ala Arg Ser Leu Gly Met His Ala
            180                 185                 190 cta tct gta gag cca tgc cac att gat gag ctc acc gcc agg gcc tct        624
Leu Ser Val Glu Pro Cys His Ile Asp Glu Leu Thr Ala Arg Ala Ser
        195                 200                 205 tcc ggc cag cta aga gat gca cag ctt ata agg cgt att gtg tgc gcc        672
Ser Gly Gln Leu Arg Asp Ala Gln Leu Ile Arg Arg Ile Val Cys Ala
210                 215                 220 atg cac ggg cca gca gta tct gca gtt gtg tcg ggc agt atc aca tcg        720
Met His Gly Pro Ala Val Ser Ala Val Val Ser Gly Ser Ile Thr Ser
225                 230                 235                 240 tcc ggc cca cag aca gca aag atc gag gaa ttg cca aca gct gct gat        768
Ser Gly Pro Gln Thr Ala Lys Ile Glu Glu Leu Pro Thr Ala Ala Asp
                245                 250                 255 agt cat ctc cgc agc gca gct ctc act tct gct cag cag ttt ttc ctc        816
Ser His Leu Arg Ser Ala Ala Leu Thr Ser Ala Gln Gln Phe Phe Leu
            260                 265                 270 aaa gtt att gct cca cat cgt cct gag aag cca ttc gtc cag ctt cca        864
Lys Val Ile Ala Pro His Arg Pro Glu Lys Pro Phe Val Gln Leu Pro
        275                 280                 285 tct ctc acc tcg gag ggc atc cga ata tac gac acc ttt gca cag ttt        912
Ser Leu Thr Ser Glu Gly Ile Arg Ile Tyr Asp Thr Phe Ala Gln Phe
290                 295                 300 gtc ata gcc gac ctg ctc gac gac acc cgc ttc cta ccc atg caa tct        960
Val Ile Ala Asp Leu Leu Asp Asp Thr Arg Phe Leu Pro Met Gln Ser
305                 310                 315                 320 cct cct ccc aat ggg ctc atc acc ttt gtt aac cca agc gcg tac ctt       1008
Pro Pro Pro Asn Gly Leu Ile Thr Phe Val Asn Pro Ser Ala Tyr Leu
                325                 330                 335 gct gat gat ata aag aat ggc aac agc cat att gtc ccg ggt gtg caa       1056
Ala Asp Asp Ile Lys Asn Gly Asn Ser His Ile Val Pro Gly Val Gln
            340                 345                 350 ttt tac gca tcc gat gcg tgc act ctc atc gac atc cca cat gac cta       1104
Phe Tyr Ala Ser Asp Ala Cys Thr Leu Ile Asp Ile Pro His Asp Leu
        355                 360                 365 gac acc acc tcc gtt ggc ttg tca gta ctg cac aag ttt gga aag gtg       1152
Asp Thr Thr Ser Val Gly Leu Ser Val Leu His Lys Phe Gly Lys Val
370                 375                 380 gac aag gac aca ctc aac aaa gtg cta gac aga atg ctc gag caa gtg       1200
Asp Lys Asp Thr Leu Asn Lys Val Leu Asp Arg Met Leu Glu Gln Val
385                 390                 395                 400 agt gaa gac gac ggc att ctg cag gtg tat ttt gat gtg gag cgt ccg       1248
Ser Glu Asp Asp Gly Ile Leu Gln Val Tyr Phe Asp Val Glu Arg Pro
                405                 410                 415
```

```
cgc atc gat cca gtt gtg gtg gca aac acg gtg ttt ctg ttc cac ttg      1296
Arg Ile Asp Pro Val Val Val Ala Asn Thr Val Phe Leu Phe His Leu
                420                 425                 430 gga aag aga ggg cat gag gtg gcg agg agt gag aag ttt gtg gag agt      1344
Gly Lys Arg Gly His Glu Val Ala Arg Ser Glu Lys Phe Val Glu Ser
            435                 440                 445 gtg ctg ctg cag agg gca tac gaa gaa ggg acg ttg tat tac aac ctg      1392
Val Leu Leu Gln Arg Ala Tyr Glu Glu Gly Thr Leu Tyr Tyr Asn Leu
        450                 455                 460 ggg gaa gca ttt ttg gtg agt gtg gcg agg ctg gtg cac gag ttt aag      1440
Gly Glu Ala Phe Leu Val Ser Val Ala Arg Leu Val His Glu Phe Lys
465                 470                 475                 480 gag cac ttt aca agg agc ggc atg agg agg gca ctg gag gag agg cta      1488
Glu His Phe Thr Arg Ser Gly Met Arg Arg Ala Leu Glu Glu Arg Leu
                485                 490                 495 aga gag cgg gca agg gcg ggc atg caa gag agg gat gat gcg ctg gcg      1536
Arg Glu Arg Ala Arg Ala Gly Met Gln Glu Arg Asp Asp Ala Leu Ala
            500                 505                 510 cta gcc atg cgc att cgt gca tgc gct ttg tgt ggc ctg gcc gga gag      1584
Leu Ala Met Arg Ile Arg Ala Cys Ala Leu Cys Gly Leu Ala Gly Glu
        515                 520                 525 ggc ctc aca aaa gca gca gag cag gag ctt ttg cgc ctg cag tgc aag      1632
Gly Leu Thr Lys Ala Ala Glu Gln Glu Leu Leu Arg Leu Gln Cys Lys
530                 535                 540 tcc aag ggc tgt tgg ggg tgc cac cct ttc tat cgc aat ggc agt aat      1680
Ser Lys Gly Cys Trp Gly Cys His Pro Phe Tyr Arg Asn Gly Ser Asn
545                 550                 555                 560 gtg ctc agc tgg atc ggc agt gag gcc ctt acc act gct tac gct att      1728
Val Leu Ser Trp Ile Gly Ser Glu Ala Leu Thr Thr Ala Tyr Ala Ile
                565                 570                 575 gct gcg cta cag ccc att gat att taa                                  1755
Ala Ala Leu Gln Pro Ile Asp Ile
            580

<210> SEQ ID NO 2
<211> LENGTH: 584
<212> TYPE: PRT
<213> ORGANISM: Dryopteris fragrans

<400> SEQUENCE: 2

Met Glu Phe Ser Ala Ser Ala Pro Pro Arg Leu Ala Ser Val Ile
1               5                   10                  15

Ile Leu Glu Pro Leu Gly Phe Leu Leu Thr Pro His Tyr Ser Ser Gln
                20                  25                  30

Leu Pro Lys Lys Leu Leu Arg Arg Leu Leu Cys Thr Arg Ile Trp His
            35                  40                  45

Arg Tyr Gln Arg Gly Arg Leu Arg Leu Arg Asp Ala Ala Met Leu Leu
        50                  55                  60

Ala Gln Leu Pro Phe Leu Ala Val Ser Asp His Pro Trp Ala Leu Asp
65                  70                  75                  80

Asn Leu Ala Ser Leu Leu Arg Pro Thr Ala Val Arg Ala Val Pro Trp
                85                  90                  95

Met Leu Leu Leu Leu Asp Phe Leu Arg Asp Glu Leu His Leu Lys Val
                100                 105                 110

Val Cys Ala Thr Asn Ser Ser Pro Glu Glu Leu Gln Glu Leu Arg His
            115                 120                 125

Gln Phe Pro Ala Leu Phe Ala Lys Val Asp Ala Thr Val Ser Ser Gly
        130                 135                 140
```

```
Glu Glu Gly Val Gly Lys Pro Ser Val Arg Phe Leu Gln Ala Ala Leu
145                 150                 155                 160

Asp Lys Ala Gly Val His Ala Gln Gln Thr Leu Tyr Leu Asp Ser Phe
            165                 170                 175

Asp Ser Leu Glu Thr Ile Met Ala Ala Arg Ser Leu Gly Met His Ala
        180                 185                 190

Leu Ser Val Glu Pro Cys His Ile Asp Glu Leu Thr Ala Arg Ala Ser
    195                 200                 205

Ser Gly Gln Leu Arg Asp Ala Gln Leu Ile Arg Arg Ile Val Cys Ala
210                 215                 220

Met His Gly Pro Ala Val Ser Ala Val Val Ser Gly Ser Ile Thr Ser
225                 230                 235                 240

Ser Gly Pro Gln Thr Ala Lys Ile Glu Glu Leu Pro Thr Ala Ala Asp
            245                 250                 255

Ser His Leu Arg Ser Ala Ala Leu Thr Ser Ala Gln Gln Phe Phe Leu
        260                 265                 270

Lys Val Ile Ala Pro His Arg Pro Glu Lys Pro Phe Val Gln Leu Pro
    275                 280                 285

Ser Leu Thr Ser Glu Gly Ile Arg Ile Tyr Asp Thr Phe Ala Gln Phe
290                 295                 300

Val Ile Ala Asp Leu Leu Asp Asp Thr Arg Phe Leu Pro Met Gln Ser
305                 310                 315                 320

Pro Pro Pro Asn Gly Leu Ile Thr Phe Val Asn Pro Ser Ala Tyr Leu
            325                 330                 335

Ala Asp Asp Ile Lys Asn Gly Asn Ser His Ile Val Pro Gly Val Gln
        340                 345                 350

Phe Tyr Ala Ser Asp Ala Cys Thr Leu Ile Asp Ile Pro His Asp Leu
    355                 360                 365

Asp Thr Thr Ser Val Gly Leu Ser Val Leu His Lys Phe Gly Lys Val
370                 375                 380

Asp Lys Asp Thr Leu Asn Lys Val Leu Asp Arg Met Leu Glu Gln Val
385                 390                 395                 400

Ser Glu Asp Asp Gly Ile Leu Gln Val Tyr Phe Asp Val Glu Arg Pro
            405                 410                 415

Arg Ile Asp Pro Val Val Ala Asn Thr Val Phe Leu Phe His Leu
        420                 425                 430

Gly Lys Arg Gly His Glu Val Ala Arg Ser Glu Lys Phe Val Glu Ser
    435                 440                 445

Val Leu Leu Gln Arg Ala Tyr Glu Glu Gly Thr Leu Tyr Tyr Asn Leu
450                 455                 460

Gly Glu Ala Phe Leu Val Ser Val Ala Arg Leu Val His Glu Phe Lys
465                 470                 475                 480

Glu His Phe Thr Arg Ser Gly Met Arg Arg Ala Leu Glu Glu Arg Leu
            485                 490                 495

Arg Glu Arg Ala Arg Ala Gly Met Gln Glu Arg Asp Asp Ala Leu Ala
        500                 505                 510

Leu Ala Met Arg Ile Arg Ala Cys Ala Leu Cys Gly Leu Ala Gly Glu
    515                 520                 525

Gly Leu Thr Lys Ala Ala Glu Gln Leu Leu Arg Leu Gln Cys Lys
530                 535                 540

Ser Lys Gly Cys Trp Gly Cys His Pro Phe Tyr Arg Asn Gly Ser Asn
545                 550                 555                 560

Val Leu Ser Trp Ile Gly Ser Glu Ala Leu Thr Thr Ala Tyr Ala Ile
```

```
                    565                 570                 575

Ala Ala Leu Gln Pro Ile Asp Ile
            580

<210> SEQ ID NO 3
<211> LENGTH: 1755
<212> TYPE: DNA
<213> ORGANISM: Dryopteris fragrans
<220> FEATURE:
<221> NAME/KEY: CDS
<222> LOCATION: (1)..(1755)

<400> SEQUENCE: 3 atg gag ttc tct gcc tct gct cct cct cct agg cta gcc agt gtc ata      48
Met Glu Phe Ser Ala Ser Ala Pro Pro Pro Arg Leu Ala Ser Val Ile
1               5                   10                  15 ata ttg gag cct ctc ggc ttc ctc ctc aca cca cac tac tcc tct cag      96
Ile Leu Glu Pro Leu Gly Phe Leu Leu Thr Pro His Tyr Ser Ser Gln
            20                  25                  30 ctt ccc aaa aag ctg ctc cgt cgc ctg ttg tgc act aga atc tgg cac     144
Leu Pro Lys Lys Leu Leu Arg Arg Leu Leu Cys Thr Arg Ile Trp His
        35                  40                  45 agg tat cag cga ggc cgc ctt cgc ctg cgt gac gct gct atg ctg ctc     192
Arg Tyr Gln Arg Gly Arg Leu Arg Leu Arg Asp Ala Ala Met Leu Leu
    50                  55                  60 gcc cag ctc cca ttc cta gct gtg tct gat cac ccc tgg gct ctg gac     240
Ala Gln Leu Pro Phe Leu Ala Val Ser Asp His Pro Trp Ala Leu Asp
65                  70                  75                  80 aat ctc gca agc ctg ctc cgc ccc aca gct gtg cgt gcg gtg cca tgg     288
Asn Leu Ala Ser Leu Leu Arg Pro Thr Ala Val Arg Ala Val Pro Trp
                85                  90                  95 atg ctg ctg ctg ctc gac ttc cta cga gac gag ctc cat ctg aag gta     336
Met Leu Leu Leu Leu Asp Phe Leu Arg Asp Glu Leu His Leu Lys Val
            100                 105                 110 gtc tgc gcg acc aac tcc tcc cca gaa gag ctg caa gag ctg cgc cac     384
Val Cys Ala Thr Asn Ser Ser Pro Glu Glu Leu Gln Glu Leu Arg His
        115                 120                 125 cag ttt ccg gcc ctc ttt gcc aag gtc gat gcc acc gtt tct tca ggc     432
Gln Phe Pro Ala Leu Phe Ala Lys Val Asp Ala Thr Val Ser Ser Gly
    130                 135                 140 gag gag ggc gtg ggc aag ccg tcc gtg cgc ttc ctg cag gct gcg ttg     480
Glu Glu Gly Val Gly Lys Pro Ser Val Arg Phe Leu Gln Ala Ala Leu
145                 150                 155                 160 gac aaa gcc ggt gtc cac gcg cag caa acc ttg tat ctt gac tct ttt     528
Asp Lys Ala Gly Val His Ala Gln Gln Thr Leu Tyr Leu Asp Ser Phe
                165                 170                 175 gac agc ttg gag acc atc atg gct gca cgc tct ctt ggc atg cat gca     576
Asp Ser Leu Glu Thr Ile Met Ala Ala Arg Ser Leu Gly Met His Ala
            180                 185                 190 cta tct gta gag cca tgc cac att gat gag ctc acc gcc agg gcc tct     624
Leu Ser Val Glu Pro Cys His Ile Asp Glu Leu Thr Ala Arg Ala Ser
        195                 200                 205 tcc ggc cag cta aga gat gca cag ctt ata agg cgt att gtg tgc gcc     672
Ser Gly Gln Leu Arg Asp Ala Gln Leu Ile Arg Arg Ile Val Cys Ala
    210                 215                 220 atg cac ggg cca gca gta tct gca gtt gtg tcg ggc agt atc aca tcg     720
Met His Gly Pro Ala Val Ser Ala Val Val Ser Gly Ser Ile Thr Ser
225                 230                 235                 240 tcc ggc cca cag aca gca aag atc gag gaa ttg cca aca gct gct gat     768
Ser Gly Pro Gln Thr Ala Lys Ile Glu Glu Leu Pro Thr Ala Ala Asp
                245                 250                 255
```

```
agt cat ctc cgc agc gca gct ctc act tct gct cag cag ttt ttc ctc      816
Ser His Leu Arg Ser Ala Ala Leu Thr Ser Ala Gln Gln Phe Phe Leu
        260                 265                 270 aaa gtt att gct cca cat cgt cct gag aag cca ttc gtc cag ctt cca      864
Lys Val Ile Ala Pro His Arg Pro Glu Lys Pro Phe Val Gln Leu Pro
        275                 280                 285 tct ctc acc tcg gag ggc atc cga ata tac gac acc ttt gca cag ttt      912
Ser Leu Thr Ser Glu Gly Ile Arg Ile Tyr Asp Thr Phe Ala Gln Phe
        290                 295                 300 gtc ata gcc gac ctg ctc gac gac acc cgc ttc cta ccc atg caa tct      960
Val Ile Ala Asp Leu Leu Asp Asp Thr Arg Phe Leu Pro Met Gln Ser
305                 310                 315                 320 cct cct ccc aat ggg ctc atc acc ttt gtt aac cca agc gcg tac ctt     1008
Pro Pro Pro Asn Gly Leu Ile Thr Phe Val Asn Pro Ser Ala Tyr Leu
                325                 330                 335 gct gat gat ata aag aat ggc aac agc cat att gtc ccg ggt gtg caa     1056
Ala Asp Asp Ile Lys Asn Gly Asn Ser His Ile Val Pro Gly Val Gln
                340                 345                 350 ttt tac gca tcc gat gcg tgc act ctc atc gac atc cca cat gac cta     1104
Phe Tyr Ala Ser Asp Ala Cys Thr Leu Ile Asp Ile Pro His Asp Leu
            355                 360                 365 gac acc acc tcc gtt ggc ttg tca gta ctg cac aag ttt gga aag gtg     1152
Asp Thr Thr Ser Val Gly Leu Ser Val Leu His Lys Phe Gly Lys Val
        370                 375                 380 gac aag gac aca ctc aac aaa gtg cta gac aga atg ctc gag caa gtg     1200
Asp Lys Asp Thr Leu Asn Lys Val Leu Asp Arg Met Leu Glu Gln Val
385                 390                 395                 400 agt gaa gac gac ggc att ctg cag gtg tat ttt gat gtg gag cgt ccg     1248
Ser Glu Asp Asp Gly Ile Leu Gln Val Tyr Phe Asp Val Glu Arg Pro
                405                 410                 415 cgc atc gat cca gtt gtg gtg gca aac acg gtg ttt ctg ttc cac ttg     1296
Arg Ile Asp Pro Val Val Val Ala Asn Thr Val Phe Leu Phe His Leu
                420                 425                 430 gga aag aga ggg cat gag gtg gcg agg agt gag aag ttt gtg gag agt     1344
Gly Lys Arg Gly His Glu Val Ala Arg Ser Glu Lys Phe Val Glu Ser
            435                 440                 445 gtg ctg ctg cag agg gca tac gaa gaa ggg acg ttg tat tac aac ctg     1392
Val Leu Leu Gln Arg Ala Tyr Glu Glu Gly Thr Leu Tyr Tyr Asn Leu
450                 455                 460 ggg gaa gca ttt ttg gtg agt gtg gcg agg ctg gtg cac gag ttt aag     1440
Gly Glu Ala Phe Leu Val Ser Val Ala Arg Leu Val His Glu Phe Lys
465                 470                 475                 480 gag cac ttt aca agg agc ggc atg agg agg gca ctg gag gag agg cta     1488
Glu His Phe Thr Arg Ser Gly Met Arg Arg Ala Leu Glu Glu Arg Leu
                485                 490                 495 aga gag cgg gca agg gcg ggc atg caa gag agg gat gat gcg ctg gcg     1536
Arg Glu Arg Ala Arg Ala Gly Met Gln Glu Arg Asp Asp Ala Leu Ala
                500                 505                 510 ctg gcc atg cgc att cgt gca tgc gct ttg tgt ggc ctg gcc gga gag     1584
Leu Ala Met Arg Ile Arg Ala Cys Ala Leu Cys Gly Leu Ala Gly Glu
            515                 520                 525 ggc ctc aca aga gca gca gag cag gag cta ctg cgc ctg cag tgc aag     1632
Gly Leu Thr Arg Ala Ala Glu Gln Glu Leu Leu Arg Leu Gln Cys Lys
        530                 535                 540 tcc aag ggc tgt tgg ggg tgc cac cct ttc tat cgc aat ggc agt aat     1680
Ser Lys Gly Cys Trp Gly Cys His Pro Phe Tyr Arg Asn Gly Ser Asn
545                 550                 555                 560 gtg ctc agc tgg atc ggc agt gag gcc ctt acc act gct tac gct att     1728
Val Leu Ser Trp Ile Gly Ser Glu Ala Leu Thr Thr Ala Tyr Ala Ile
```

```
                   565                 570                 575
gct gcg cta cag ccc att gat att taa                                  1755
Ala Ala Leu Gln Pro Ile Asp Ile
            580

<210> SEQ ID NO 4
<211> LENGTH: 584
<212> TYPE: PRT
<213> ORGANISM: Dryopteris fragrans

<400> SEQUENCE: 4

Met Glu Phe Ser Ala Ser Ala Pro Pro Arg Leu Ala Ser Val Ile
1               5                   10                  15

Ile Leu Glu Pro Leu Gly Phe Leu Leu Thr Pro His Tyr Ser Ser Gln
                20                  25                  30

Leu Pro Lys Lys Leu Leu Arg Arg Leu Leu Cys Thr Arg Ile Trp His
                35                  40                  45

Arg Tyr Gln Arg Gly Arg Leu Arg Leu Arg Asp Ala Ala Met Leu Leu
        50                  55                  60

Ala Gln Leu Pro Phe Leu Ala Val Ser Asp His Pro Trp Ala Leu Asp
65                  70                  75                  80

Asn Leu Ala Ser Leu Leu Arg Pro Thr Ala Val Arg Ala Val Pro Trp
                85                  90                  95

Met Leu Leu Leu Leu Asp Phe Leu Arg Asp Glu Leu His Leu Lys Val
                100                 105                 110

Val Cys Ala Thr Asn Ser Ser Pro Glu Glu Leu Gln Glu Leu Arg His
            115                 120                 125

Gln Phe Pro Ala Leu Phe Ala Lys Val Asp Ala Thr Val Ser Ser Gly
        130                 135                 140

Glu Glu Gly Val Gly Lys Pro Ser Val Arg Phe Leu Gln Ala Ala Leu
145                 150                 155                 160

Asp Lys Ala Gly Val His Ala Gln Gln Thr Leu Tyr Leu Asp Ser Phe
                165                 170                 175

Asp Ser Leu Glu Thr Ile Met Ala Ala Arg Ser Leu Gly Met His Ala
            180                 185                 190

Leu Ser Val Glu Pro Cys His Ile Asp Glu Leu Thr Ala Arg Ala Ser
        195                 200                 205

Ser Gly Gln Leu Arg Asp Ala Gln Leu Ile Arg Arg Ile Val Cys Ala
    210                 215                 220

Met His Gly Pro Ala Val Ser Ala Val Ser Gly Ser Ile Thr Ser
225                 230                 235                 240

Ser Gly Pro Gln Thr Ala Lys Ile Glu Glu Leu Pro Thr Ala Ala Asp
                245                 250                 255

Ser His Leu Arg Ser Ala Ala Leu Thr Ser Ala Gln Phe Phe Leu
            260                 265                 270

Lys Val Ile Ala Pro His Arg Pro Glu Lys Pro Phe Val Gln Leu Pro
        275                 280                 285

Ser Leu Thr Ser Glu Gly Ile Arg Ile Tyr Asp Thr Phe Ala Gln Phe
    290                 295                 300

Val Ile Ala Asp Leu Leu Asp Thr Arg Phe Leu Pro Met Gln Ser
305                 310                 315                 320

Pro Pro Pro Asn Gly Leu Ile Thr Phe Val Asn Pro Ser Ala Tyr Leu
                325                 330                 335

Ala Asp Asp Ile Lys Asn Gly Asn Ser His Ile Val Pro Gly Val Gln
            340                 345                 350
```

```
Phe Tyr Ala Ser Asp Ala Cys Thr Leu Ile Asp Ile Pro His Asp Leu
            355                 360                 365

Asp Thr Thr Ser Val Gly Leu Ser Val Leu His Lys Phe Gly Lys Val
        370                 375                 380

Asp Lys Asp Thr Leu Asn Lys Val Leu Asp Arg Met Leu Glu Gln Val
385                 390                 395                 400

Ser Glu Asp Asp Gly Ile Leu Gln Val Tyr Phe Asp Val Glu Arg Pro
                405                 410                 415

Arg Ile Asp Pro Val Val Ala Asn Thr Val Phe Leu Phe His Leu
            420                 425                 430

Gly Lys Arg Gly His Glu Val Ala Arg Ser Glu Lys Phe Val Glu Ser
        435                 440                 445

Val Leu Leu Gln Arg Ala Tyr Glu Gly Thr Leu Tyr Tyr Asn Leu
    450                 455                 460

Gly Glu Ala Phe Leu Val Ser Val Ala Arg Leu Val His Glu Phe Lys
465                 470                 475                 480

Glu His Phe Thr Arg Ser Gly Met Arg Ala Leu Glu Glu Arg Leu
                485                 490                 495

Arg Glu Arg Ala Arg Ala Gly Met Gln Glu Arg Asp Asp Ala Leu Ala
            500                 505                 510

Leu Ala Met Arg Ile Arg Ala Cys Ala Leu Cys Gly Leu Ala Gly Glu
        515                 520                 525

Gly Leu Thr Arg Ala Ala Glu Gln Glu Leu Leu Arg Leu Gln Cys Lys
    530                 535                 540

Ser Lys Gly Cys Trp Gly Cys His Pro Phe Tyr Arg Asn Gly Ser Asn
545                 550                 555                 560

Val Leu Ser Trp Ile Gly Ser Glu Ala Leu Thr Thr Ala Tyr Ala Ile
                565                 570                 575

Ala Ala Leu Gln Pro Ile Asp Ile
            580

<210> SEQ ID NO 5
<211> LENGTH: 1755
<212> TYPE: DNA
<213> ORGANISM: Dryopteris fragrans
<220> FEATURE:
<221> NAME/KEY: CDS
<222> LOCATION: (1)..(1755)

<400> SEQUENCE: 5 atg gag ttc tct gcc tct gct cct cct cct agg cta gcc agt gtc ata    48
Met Glu Phe Ser Ala Ser Ala Pro Pro Pro Arg Leu Ala Ser Val Ile
1               5                   10                  15 ata ttg gag cct ctc ggc ttc ctc ctc aca cca cac tac tcc tct cag    96
Ile Leu Glu Pro Leu Gly Phe Leu Leu Thr Pro His Tyr Ser Ser Gln
            20                  25                  30 ctt ccc aaa aag ctg ctc cgt cgc ctg ttg tgc act aga atc tgg cac   144
Leu Pro Lys Lys Leu Leu Arg Arg Leu Leu Cys Thr Arg Ile Trp His
        35                  40                  45 agg tat cag cga ggc cgc ctt cgc ctg cgt gac gct gct atg ctg ctc   192
Arg Tyr Gln Arg Gly Arg Leu Arg Leu Arg Asp Ala Ala Met Leu Leu
    50                  55                  60 gcc cag ctc cca ttc cta gct gtg tct gat cac ccc tgg gct ctg gac   240
Ala Gln Leu Pro Phe Leu Ala Val Ser Asp His Pro Trp Ala Leu Asp
65                  70                  75                  80 aat ctc gca agc ctg ctc cgc ccc aca gct gtg cgt gcg gtg cca tgg   288
Asn Leu Ala Ser Leu Leu Arg Pro Thr Ala Val Arg Ala Val Pro Trp
```

|  |  |  |  |  |  |  |  |  |  |  |  |  |  |  |  |
|---|---|---|---|---|---|---|---|---|---|---|---|---|---|---|---|
|  |  |  |  | 85 |  |  |  | 90 |  |  |  | 95 |  |  |  |
| atg | ctg | ctg | ctg | ctc | gac | ttc | cta | cga | gac | gag | ctc | cat | ctg | aag | gta |
| Met | Leu | Leu | Leu | Leu | Asp | Phe | Leu | Arg | Asp | Glu | Leu | His | Leu | Lys | Val |
|  |  |  | 100 |  |  |  |  | 105 |  |  |  |  | 110 |  |  |

336

| gtc | tgc | gcg | acc | aac | tcc | tcc | cca | gaa | gag | ctg | caa | gag | ctg | cgc | cac |
|---|---|---|---|---|---|---|---|---|---|---|---|---|---|---|---|
| Val | Cys | Ala | Thr | Asn | Ser | Ser | Pro | Glu | Glu | Leu | Gln | Glu | Leu | Arg | His |
|  |  | 115 |  |  |  |  | 120 |  |  |  |  | 125 |  |  |  |

384

| cag | ttt | ccg | gcc | ctc | ttt | gcc | aag | gtc | gat | gcc | acc | gtt | tct | tca | ggc |
|---|---|---|---|---|---|---|---|---|---|---|---|---|---|---|---|
| Gln | Phe | Pro | Ala | Leu | Phe | Ala | Lys | Val | Asp | Ala | Thr | Val | Ser | Ser | Gly |
| 130 |  |  |  |  | 135 |  |  |  |  | 140 |  |  |  |  |  |

432

| gag | gag | ggc | gtg | ggc | aag | ccg | tcc | gtg | cgc | ttc | ctg | cag | gct | gcg | ttg |
|---|---|---|---|---|---|---|---|---|---|---|---|---|---|---|---|
| Glu | Glu | Gly | Val | Gly | Lys | Pro | Ser | Val | Arg | Phe | Leu | Gln | Ala | Ala | Leu |
| 145 |  |  |  | 150 |  |  |  |  | 155 |  |  |  |  | 160 |  |

480

| gac | aaa | gcc | ggt | gtc | cac | gcg | cag | caa | acc | ttg | tat | ctt | gac | tct | ttt |
|---|---|---|---|---|---|---|---|---|---|---|---|---|---|---|---|
| Asp | Lys | Ala | Gly | Val | His | Ala | Gln | Gln | Thr | Leu | Tyr | Leu | Asp | Ser | Phe |
|  |  |  |  | 165 |  |  |  |  | 170 |  |  |  |  | 175 |  |

528

| gac | agc | ttg | gag | acc | atc | atg | gct | gca | cgc | tct | ctt | ggc | atg | cat | gca |
|---|---|---|---|---|---|---|---|---|---|---|---|---|---|---|---|
| Asp | Ser | Leu | Glu | Thr | Ile | Met | Ala | Ala | Arg | Ser | Leu | Gly | Met | His | Ala |
|  |  |  | 180 |  |  |  |  | 185 |  |  |  |  | 190 |  |  |

576

| cta | tct | gta | gag | cca | tgc | cac | att | gat | gag | ctc | acc | gcc | agg | gcc | tct |
|---|---|---|---|---|---|---|---|---|---|---|---|---|---|---|---|
| Leu | Ser | Val | Glu | Pro | Cys | His | Ile | Asp | Glu | Leu | Thr | Ala | Arg | Ala | Ser |
|  |  | 195 |  |  |  |  | 200 |  |  |  |  | 205 |  |  |  |

624

| tcc | ggc | cag | cta | aga | gat | gca | cag | ctt | ata | agg | cgt | att | gtg | tgc | gcc |
|---|---|---|---|---|---|---|---|---|---|---|---|---|---|---|---|
| Ser | Gly | Gln | Leu | Arg | Asp | Ala | Gln | Leu | Ile | Arg | Arg | Ile | Val | Cys | Ala |
| 210 |  |  |  |  | 215 |  |  |  |  | 220 |  |  |  |  |  |

672

| atg | cac | ggg | cca | gca | gta | tct | gca | gtt | gtg | tcg | ggc | agt | atc | aca | tcg |
|---|---|---|---|---|---|---|---|---|---|---|---|---|---|---|---|
| Met | His | Gly | Pro | Ala | Val | Ser | Ala | Val | Val | Ser | Gly | Ser | Ile | Thr | Ser |
| 225 |  |  |  | 230 |  |  |  |  | 235 |  |  |  |  | 240 |  |

720

| tcc | ggc | cca | cag | aca | gca | aag | atc | gag | gaa | ttg | cca | aca | gct | gct | gat |
|---|---|---|---|---|---|---|---|---|---|---|---|---|---|---|---|
| Ser | Gly | Pro | Gln | Thr | Ala | Lys | Ile | Glu | Glu | Leu | Pro | Thr | Ala | Ala | Asp |
|  |  |  |  | 245 |  |  |  |  | 250 |  |  |  |  | 255 |  |

768

| agt | cat | ctc | cgc | agc | gca | gct | ctc | act | tct | gct | cag | cag | ttt | ttc | ctc |
|---|---|---|---|---|---|---|---|---|---|---|---|---|---|---|---|
| Ser | His | Leu | Arg | Ser | Ala | Ala | Leu | Thr | Ser | Ala | Gln | Gln | Phe | Phe | Leu |
|  |  |  | 260 |  |  |  |  | 265 |  |  |  |  | 270 |  |  |

816

| aaa | gct | att | gct | cca | cat | cgt | cct | gag | aag | cca | ttc | gtc | cag | ctt | cca |
|---|---|---|---|---|---|---|---|---|---|---|---|---|---|---|---|
| Lys | Ala | Ile | Ala | Pro | His | Arg | Pro | Glu | Lys | Pro | Phe | Val | Gln | Leu | Pro |
|  |  | 275 |  |  |  |  | 280 |  |  |  |  | 285 |  |  |  |

864

| tct | ctc | acc | tcg | gag | ggc | atc | cga | ata | tac | gac | acc | ttt | gca | cag | ttt |
|---|---|---|---|---|---|---|---|---|---|---|---|---|---|---|---|
| Ser | Leu | Thr | Ser | Glu | Gly | Ile | Arg | Ile | Tyr | Asp | Thr | Phe | Ala | Gln | Phe |
| 290 |  |  |  |  | 295 |  |  |  |  | 300 |  |  |  |  |  |

912

| gtc | ata | gcc | gac | ctg | ctc | gac | gac | acc | cgc | ttc | cta | ccc | atg | caa | tct |
|---|---|---|---|---|---|---|---|---|---|---|---|---|---|---|---|
| Val | Ile | Ala | Asp | Leu | Leu | Asp | Asp | Thr | Arg | Phe | Leu | Pro | Met | Gln | Ser |
| 305 |  |  |  | 310 |  |  |  |  | 315 |  |  |  |  | 320 |  |

960

| cct | cct | ccc | aat | ggg | ctc | atc | acc | ttt | gtt | aac | cca | agc | gcg | tac | ctt |
|---|---|---|---|---|---|---|---|---|---|---|---|---|---|---|---|
| Pro | Pro | Pro | Asn | Gly | Leu | Ile | Thr | Phe | Val | Asn | Pro | Ser | Ala | Tyr | Leu |
|  |  |  |  | 325 |  |  |  |  | 330 |  |  |  |  | 335 |  |

1008

| gct | gat | gat | ata | aag | aat | ggc | aac | agc | cat | att | gtc | ccg | ggt | gtg | caa |
|---|---|---|---|---|---|---|---|---|---|---|---|---|---|---|---|
| Ala | Asp | Asp | Ile | Lys | Asn | Gly | Asn | Ser | His | Ile | Val | Pro | Gly | Val | Gln |
|  |  |  | 340 |  |  |  |  | 345 |  |  |  |  | 350 |  |  |

1056

| ttt | tac | gca | tct | gat | gcg | tgc | act | ctc | atc | gac | atc | cca | cat | gac | cta |
|---|---|---|---|---|---|---|---|---|---|---|---|---|---|---|---|
| Phe | Tyr | Ala | Ser | Asp | Ala | Cys | Thr | Leu | Ile | Asp | Ile | Pro | His | Asp | Leu |
|  |  | 355 |  |  |  |  | 360 |  |  |  |  | 365 |  |  |  |

1104

| gac | acc | acc | tcc | gtt | ggc | ttg | tca | gta | ctg | cac | aag | ttt | gga | aag | gtg |
|---|---|---|---|---|---|---|---|---|---|---|---|---|---|---|---|
| Asp | Thr | Thr | Ser | Val | Gly | Leu | Ser | Val | Leu | His | Lys | Phe | Gly | Lys | Val |
| 370 |  |  |  |  | 375 |  |  |  |  | 380 |  |  |  |  |  |

1152

| gac | aag | gac | aca | ctc | aac | aaa | gtg | cta | gac | aga | atg | ctg | gag | caa | gtg |
|---|---|---|---|---|---|---|---|---|---|---|---|---|---|---|---|
| Asp | Lys | Asp | Thr | Leu | Asn | Lys | Val | Leu | Asp | Arg | Met | Leu | Glu | Gln | Val |
| 385 |  |  |  | 390 |  |  |  |  | 395 |  |  |  |  | 400 |  |

1200

| agt | gaa | gac | gac | ggc | att | ctc | cag | gtg | tat | ttt | gat | gtg | gag | cgt | ccg |
|---|---|---|---|---|---|---|---|---|---|---|---|---|---|---|---|

1248

-continued

```
Ser Glu Asp Asp Gly Ile Leu Gln Val Tyr Phe Asp Val Glu Arg Pro
                405                 410                 415 cgc atc gat cca gtt gtg gtg gca aac acg gtg ttt ctg ttc cac ttg    1296
Arg Ile Asp Pro Val Val Val Ala Asn Thr Val Phe Leu Phe His Leu
                420                 425                 430 gga aag aga ggg cat gag gtg gcg agg agt gag aag ttt gtg gag agt    1344
Gly Lys Arg Gly His Glu Val Ala Arg Ser Glu Lys Phe Val Glu Ser
            435                 440                 445 gtg ctg ctg cag agg gca tac gaa gaa ggg acg ttg tat tac aac ctg    1392
Val Leu Leu Gln Arg Ala Tyr Glu Glu Gly Thr Leu Tyr Tyr Asn Leu
        450                 455                 460 ggg gaa gca ttt ttg gtg agt gtg gcg agg ctg gtg cac gag ttt aag    1440
Gly Glu Ala Phe Leu Val Ser Val Ala Arg Leu Val His Glu Phe Lys
465                 470                 475                 480 gag cac ttt aca agg agc ggc atg agg agg gca ctg gag gag agg cta    1488
Glu His Phe Thr Arg Ser Gly Met Arg Arg Ala Leu Glu Glu Arg Leu
                485                 490                 495 aga gag cgg gca agg gcg ggc atg caa gag agg gat gat gcg ctg gcg    1536
Arg Glu Arg Ala Arg Ala Gly Met Gln Glu Arg Asp Asp Ala Leu Ala
            500                 505                 510 ctg gcc atg cgc att cgt gca tgc gct ttg tgt ggc ctg gcc gga gag    1584
Leu Ala Met Arg Ile Arg Ala Cys Ala Leu Cys Gly Leu Ala Gly Glu
        515                 520                 525 ggc ctc aca aaa gca gca gag cag gag cta ctg cgc ctg cag tgc aag    1632
Gly Leu Thr Lys Ala Ala Glu Gln Glu Leu Leu Arg Leu Gln Cys Lys
530                 535                 540 tcc aag ggc tgt tgg ggg tgc cac cct ttc tat cgc aat ggc agt aat    1680
Ser Lys Gly Cys Trp Gly Cys His Pro Phe Tyr Arg Asn Gly Ser Asn
545                 550                 555                 560 gtg ctc agc tgg atc ggc agt gag gcc ctt acc act gct tac gct att    1728
Val Leu Ser Trp Ile Gly Ser Glu Ala Leu Thr Thr Ala Tyr Ala Ile
                565                 570                 575 gct gcg cta cag ccc att gat att taa                                1755
Ala Ala Leu Gln Pro Ile Asp Ile
            580
```

<210> SEQ ID NO 6
<211> LENGTH: 584
<212> TYPE: PRT
<213> ORGANISM: Dryopteris fragrans

<400> SEQUENCE: 6

```
Met Glu Phe Ser Ala Ser Ala Pro Pro Arg Leu Ala Ser Val Ile
1               5                   10                  15

Ile Leu Glu Pro Leu Gly Phe Leu Leu Thr Pro His Tyr Ser Ser Gln
                20                  25                  30

Leu Pro Lys Lys Leu Leu Arg Arg Leu Leu Cys Thr Arg Ile Trp His
            35                  40                  45

Arg Tyr Gln Arg Gly Arg Leu Arg Leu Arg Asp Ala Ala Met Leu Leu
        50                  55                  60

Ala Gln Leu Pro Phe Leu Ala Val Ser Asp His Pro Trp Ala Leu Asp
65                  70                  75                  80

Asn Leu Ala Ser Leu Leu Arg Pro Thr Ala Val Arg Ala Val Pro Trp
                85                  90                  95

Met Leu Leu Leu Leu Asp Phe Leu Arg Asp Glu Leu His Leu Lys Val
                100                 105                 110

Val Cys Ala Thr Asn Ser Ser Pro Glu Glu Leu Gln Glu Leu Arg His
            115                 120                 125
```

```
Gln Phe Pro Ala Leu Phe Ala Lys Val Asp Ala Thr Val Ser Ser Gly
    130                 135                 140

Glu Glu Gly Val Gly Lys Pro Ser Val Arg Phe Leu Gln Ala Ala Leu
145                 150                 155                 160

Asp Lys Ala Gly Val His Ala Gln Gln Thr Leu Tyr Leu Asp Ser Phe
                165                 170                 175

Asp Ser Leu Glu Thr Ile Met Ala Ala Arg Ser Leu Gly Met His Ala
            180                 185                 190

Leu Ser Val Glu Pro Cys His Ile Asp Glu Leu Thr Ala Arg Ala Ser
        195                 200                 205

Ser Gly Gln Leu Arg Asp Ala Gln Leu Ile Arg Arg Ile Val Cys Ala
210                 215                 220

Met His Gly Pro Ala Val Ser Ala Val Val Ser Gly Ser Ile Thr Ser
225                 230                 235                 240

Ser Gly Pro Gln Thr Ala Lys Ile Glu Glu Leu Pro Thr Ala Ala Asp
                245                 250                 255

Ser His Leu Arg Ser Ala Ala Leu Thr Ser Ala Gln Gln Phe Phe Leu
            260                 265                 270

Lys Ala Ile Ala Pro His Arg Pro Glu Lys Pro Phe Val Gln Leu Pro
        275                 280                 285

Ser Leu Thr Ser Glu Gly Ile Arg Ile Tyr Asp Thr Phe Ala Gln Phe
    290                 295                 300

Val Ile Ala Asp Leu Leu Asp Asp Thr Arg Phe Leu Pro Met Gln Ser
305                 310                 315                 320

Pro Pro Pro Asn Gly Leu Ile Thr Phe Val Asn Pro Ser Ala Tyr Leu
                325                 330                 335

Ala Asp Asp Ile Lys Asn Gly Asn Ser His Ile Val Pro Gly Val Gln
            340                 345                 350

Phe Tyr Ala Ser Asp Ala Cys Thr Leu Ile Asp Ile Pro His Asp Leu
        355                 360                 365

Asp Thr Thr Ser Val Gly Leu Ser Val Leu His Lys Phe Gly Lys Val
    370                 375                 380

Asp Lys Asp Thr Leu Asn Lys Val Leu Asp Arg Met Leu Glu Gln Val
385                 390                 395                 400

Ser Glu Asp Asp Gly Ile Leu Gln Val Tyr Phe Asp Val Glu Arg Pro
                405                 410                 415

Arg Ile Asp Pro Val Val Ala Asn Thr Val Phe Leu Phe His Leu
            420                 425                 430

Gly Lys Arg Gly His Glu Val Ala Arg Ser Glu Lys Phe Val Glu Ser
        435                 440                 445

Val Leu Leu Gln Arg Ala Tyr Glu Glu Gly Thr Leu Tyr Tyr Asn Leu
    450                 455                 460

Gly Glu Ala Phe Leu Val Ser Val Ala Arg Leu Val His Glu Phe Lys
465                 470                 475                 480

Glu His Phe Thr Arg Ser Gly Met Arg Ala Leu Glu Glu Arg Leu
                485                 490                 495

Arg Glu Arg Ala Arg Ala Gly Met Gln Glu Arg Asp Asp Ala Leu Ala
        500                 505                 510

Leu Ala Met Arg Ile Arg Ala Cys Ala Leu Cys Gly Leu Ala Gly Glu
    515                 520                 525

Gly Leu Thr Lys Ala Ala Glu Gln Glu Leu Leu Arg Leu Gln Cys Lys
530                 535                 540

Ser Lys Gly Cys Trp Gly Cys His Pro Phe Tyr Arg Asn Gly Ser Asn
```

```
         545                 550                 555                 560
Val Leu Ser Trp Ile Gly Ser Glu Ala Leu Thr Thr Ala Tyr Ala Ile
                 565                 570                 575

Ala Ala Leu Gln Pro Ile Asp Ile
            580

<210> SEQ ID NO 7
<211> LENGTH: 1755
<212> TYPE: DNA
<213> ORGANISM: Artificial Sequence
<220> FEATURE:
<223> OTHER INFORMATION: Synthesized, Codon-optimized sequence of DfHAD
      by Genscript genetic codon frequency of E. coli

<400> SEQUENCE: 7
atggagttca gcgcgagcgc tccgccgccg cgtctggcga gcgtgatcat tctggaaccg        60
ctgggttttc tgctgacccc gcactacagc agccagctgc gaagaaaact gctgcgtcgt       120
ctgctgtgca cccgtatctg gcaccgttat cagcgtggcc gtctgcgtct gcgtgacgcg       180
gcgatgctgc tggcgcaact gccgttcctg gcggttagcg accaccgtg ggcgctggat        240 aacctggcga gcctgctgcg tccgaccgcg gttcgtgcgg tgccgtggat gctgctgctg       300
ctggactttc tgcgtgatga gctgcacctg aaagtggttt gcgcgaccaa cagcagcccg       360
gaggaactgc aggaactgcg tcaccaattc ccggcgctgt ttgcgaaggt tgacgcgacc       420
gtgagcagcg gcgaggaagg tgttggcaaa ccgagcgtgc gtttcctgca gcggcgctg        480 gataaggcgg gcgtgcacgc gcagcaaacc ctgtacctgg acagctttga tagcctggag       540
accatcatgg cggcgcgtag cctgggtatg cacgcgctga gcgttgagcc gtgccacatt       600
gacgaactga ccgcgcgtgc gagcagcggt cagctgcgtg atgcgcaact gatccgtcgt       660
attgtttgcg cgatgcacgg tccggctgtg agcgcggtgg ttagcggtag catcaccagc       720
agcggtccgc agaccgcgaa aattgaggaa ctgccgaccg cggcggacag ccacctgcgt       780
agcgcggcgc tgaccagcgc gcagcaattc tttctgaaag tgattgcgcc gcaccgtccg       840
gagaagccgt tcgttcaact gccgagcctg accagcgaag gtatccgtat ttatgacacc       900
ttcgcgcagt ttgtgatcgc ggatctgctg gacgataccc gtttcctgcc gatgcaaagc       960
ccgccgccga acggcctgat tacctttgtt aacccgagcg cgtacctggc ggacgatatc      1020
aaaaacggta acagccacat tgttccgggc gtgcagttct atgcgagcga cgcgtgcacc      1080
ctgatcgata ttccgcacga cctggatacc accagcgttg gtctgagcgt gctgcacaag      1140
tttggcaaag ttgacaagga taccctgaac aaggtgctgg atcgtatgct ggagcaagtt      1200
agcgaagacg atggtatcct gcaagtttac tttgacgtgg agcgtccgcg tattgatccg      1260
gtggttgtgg cgaacaccgt gttcctgttt cacctgggta acgtggcca cgaagttgcg       1320 cgtagcgaga agttcgttga aagcgtgctg ctgcagcgtg cgtacgagga aggcaccctg      1380
tactataacc tgggcgaagc gtttctggtt agcgtggcgc gtctggtgca cgagttcaaa      1440
gaacacttta cccgtagcgg tatgcgtcgt gcgctggagg aacgtctgcg tgagcgtgcg      1500
cgtgcgggta tgcaagaacg tgacgatgcg ctggcgctgg cgatgcgtat ccgtgcgtgc      1560
gcgctgtgcg gtctggcggg cgaggtctg accaaggcgg cggagcagga actgctgcgt       1620
ctgcaatgca gagcaaaagg ttgctgggc tgccacccgt tctaccgtaa cggtagcaac       1680
gttctgagct ggatcggcag cgaagcgctg accaccgcgt atgcgattgc ggcgctgcag      1740
ccgatcgaca tttaa                                                        1755
```

<210> SEQ ID NO 8
<211> LENGTH: 1755
<212> TYPE: DNA
<213> ORGANISM: Artificial Sequence
<220> FEATURE:
<223> OTHER INFORMATION: Synthesized, Codon-optimized sequence of DfHAD by Genscript genetic codon frequency of tobacco

<400> SEQUENCE: 8

| | | | | | |
|---|---|---|---|---|---|
| atggaattt | ctgcttcagc | tccacctcca | agacttgctt | cagttattat | tcttgagcct | 60 |
| ttgggatttc | ttttgactcc | acattactct | tcacaattgc | taagaaact | tttgagaagg | 120 |
| cttttgtgta | caagaatttg | gcataggtac | caaaggggta | ggcttagatt | gagggatgct | 180 |
| gctatgcttt | tggctcaact | tccattttg | gctgtttcag | atcatccttg | ggctcttgat | 240 |
| aatttggctt | ctcttttgag | accaactgct | gttaggctg | ttccttggat | gcttttgctt | 300 |
| ttggattttc | ttagagatga | acttcatttg | aaggttgttt | gcgctactaa | ttcttcacca | 360 |
| gaagagcttc | aagagttgag | gcatcaattt | cctgctttgt | ttgctaaggt | tgatgctaca | 420 |
| gtttcttcag | gagaagaggg | agttggtaaa | ccatctgtta | gatttcttca | agctgctttg | 480 |
| gataaggctg | tgttcatgc | tcaacaaact | ctttatttgg | attctttcga | ttcacttgaa | 540 |
| acaattatgg | ctgctaggtc | attgggaatg | catgctcttt | ctgttgaacc | atgtcatatt | 600 |
| gatgagttga | ctgctagagc | ttcttcagga | caattgaggg | atgctcaact | tattagaagg | 660 |
| attgtttgcg | ctatgcatgg | tcctgctgtt | tcagctgttg | tttctggatc | aattacttct | 720 |
| tcaggtccac | aaacagctaa | aattgaagag | cttcctactg | ctgctgattc | tcatttgaga | 780 |
| tcagctgctc | ttacatctgc | tcaacaattt | ttccttaaag | ttattgctcc | acatagacct | 840 |
| gaaaagccat | tgttcaact | tccttctttg | acttcagagg | gaatcaggat | ctatgataca | 900 |
| ttcgctcaat | tcgttatcgc | tgatcttttg | gatgatacta | ggttttgcc | aatgcaatca | 960 |
| cctccaccta | atggtcttat | cacattcgtt | aacccttctg | cttatttggc | tgatgatatt | 1020 |
| aaaaatggta | actcacatat | tgttccaggt | gttcaatttt | acgcttctga | tgcttgtact | 1080 |
| ttgattgata | ttcctcatga | tcttgatact | acatctgttg | gactttcagt | tttgcataag | 1140 |
| ttcggtaaag | ttgataagga | tacacttaat | aaggttttgg | atagaatgct | tgaacaagtt | 1200 |
| tcagaggatg | atggaatcct | tcaagtttac | ttcgatgttg | aaagacctag | gattgatcca | 1260 |
| gttgttgttg | ctaacactgt | ttttcttttc | catttgggaa | aaagaggtca | tgaggttgct | 1320 |
| agatcagaaa | agtttgttga | gtctgttctt | ttgcaaagag | cttacgaaga | gggaactttg | 1380 |
| tattacaatc | ttggtgaagc | ttttcttgtt | tctgttgcta | gacttgttca | tgagtttaag | 1440 |
| gagcatttta | caaggtctgg | aatgagaagg | gctttggaag | agagacttag | ggaaagagct | 1500 |
| agggctggta | tgcaagagag | agatgatgct | cttgctttgg | ctatgagaat | tagggcttgt | 1560 |
| gctctttgcg | gtttggctgg | agaaggtctt | acaaaggctg | ctgaacaaga | gcttttgaga | 1620 |
| ttgcaatgca | agtctaaagg | atgttggggt | tgccatccat | tctacaggaa | tggttctaac | 1680 |
| gttttgtcat | ggattggttc | tgaggctctt | actacagctt | acgctattgc | tgctcttcaa | 1740 |
| cctattgata | tttga | | | | | 1755 |

<210> SEQ ID NO 9
<211> LENGTH: 1755
<212> TYPE: DNA
<213> ORGANISM: Artificial Sequence
<220> FEATURE:
<223> OTHER INFORMATION: Synthesized, Codon-optimized sequence of DfHAD-8(K532R) by Genscript genetic codon frequency of E. coli

<400> SEQUENCE: 9

```
atggagttca gcgcgagcgc tccgccgccg cgtctggcga cgtgatcat tctggaaccg      60
ctgggttttc tgctgacccc gcactacagc agccagctgc cgaagaaact gctgcgtcgt    120
ctgctgtgca cccgtatctg gcaccgttat cagcgtggcc gtctgcgtct gcgtgacgcg    180
gcgatgctgc tggcgcaact gccgttcctg gcggttagcg accacccgtg ggcgctggat    240
aacctggcga gcctgctgcg tccgaccgcg gttcgtgcgg tgccgtggat gctgctgctg    300
ctggactttc tgcgtgatga gctgcacctg aaagtggttt gcgcgaccaa cagcagcccg    360
gaggaactgc aggaactgcg tcaccaattc ccggcgctgt tgcgaaggt tgacgcgacc     420
gtgagcagcg gcgaggaagg tgttggcaaa ccgagcgtgc gtttcctgca gcggcgctg    480
gataaggcgg gcgtgcacgc gcagcaaacc ctgtacctgg acagctttga tagcctggag    540
accatcatgg cggcgcgtag cctgggtatg cacgcgctga gcgttgagcc gtgccacatt    600
gacgaactga ccgcgcgtgc gagcagcggt cagctgcgtg atgcgcaact gatccgtcgt    660
attgtttgcg cgatgcacgg tccggctgtg agcgcggtgg ttagcggtag catcaccagc    720
agcggtccgc agaccgcgaa aattgaggaa ctgccgaccg cggcggacag ccacctgcgt    780
agcgcggcgc tgaccagcgc gcagcaattc tttctgaaag tgattgcgcc gcaccgtccg    840
gagaagccgt tcgttcaact gccgagcctg accagcgaag gtatccgtat ttatgacacc    900
ttcgcgcagt ttgtgatcgc ggatctgctg gacgatacc gtttcctgcc gatgcaaagc     960
ccgccgccga acggcctgat taccttgtt aacccgagcg cgtacctggc ggacgatatc    1020
aaaaacggta acagccacat tgttccgggc gtgcagttct atgcgagcga cgcgtgcacc    1080
ctgatcgata ttccgcacga cctggatacc accagcgttg gtctgagcgt gctgcacaag    1140
tttggcaaag ttgacaagga tacctgaac aaggtgctgg atcgtatgct ggagcaagtt    1200
agcgaagacg atggtatcct gcaagtttac tttgacgtgg agcgtccgcg tattgatccg    1260
gtggttgtgg cgaacaccgt gttcctgttt cacctgggta acgtggcca cgaagttgcg    1320
cgtagcgaga agttcgttga aagcgtgctg ctgcagcgtg cgtacgagga aggcacccctg    1380
tactataacc tgggcgaagc gttttctggtt agcgtggcgc gtctggtgca cgagttcaaa    1440
gaacacttta cccgtagcgg tatgcgtcgt gcgctggagg aacgtctgcg tgagcgtgcg    1500
cgtgcgggta tgcaagaacg tgacgatgcg ctggcgctgg cgatgcgtat ccgtgcgtgc    1560
gcgctgtgcg gtctggcggg cgagggtctg acccgggcgg cggagcagga actgctgcgt    1620
ctgcaatgca gagcaaagg ttgctggggc tgccacccgt tctaccgtaa cggtagcaac    1680
gttctgagct ggatcggcag cgaagcgctg accaccgcgt atgcgattgc ggcgctgcag    1740
ccgatcgaca tttaa                                                    1755
```

<210> SEQ ID NO 10
<211> LENGTH: 1755
<212> TYPE: DNA
<213> ORGANISM: Artificial Sequence
<220> FEATURE:
<223> OTHER INFORMATION: Synthesized, Codon-optimized sequence of DfHAD-9(V274A) by Genscript genetic codon frequency of E. coli

<400> SEQUENCE: 10

```
atggagttca gcgcgagcgc tccgccgccg cgtctggcga cgtgatcat tctggaaccg      60
ctgggttttc tgctgacccc gcactacagc agccagctgc cgaagaaact gctgcgtcgt    120
ctgctgtgca cccgtatctg gcaccgttat cagcgtggcc gtctgcgtct gcgtgacgcg    180
```

```
gcgatgctgc tggcgcaact gccgttcctg gcggttagcg accacccgtg ggcgctggat    240
aacctggcga gcctgctgcg tccgaccgcg gttcgtgcgg tgccgtggat gctgctgctg    300
ctggactttc tgcgtgatga gctgcacctg aaagtggttt gcgcgaccaa cagcagcccg    360
gaggaactgc aggaactgcg tcaccaattc ccggcgctgt tgcgaaggt tgacgcgacc     420 gtgagcagcg gcgaggaagg tgttggcaaa ccgagcgtgc gtttcctgca gcggcgctg    480 gataaggcgg gcgtgcacgc gcagcaaacc ctgtacctgg acagctttga tagcctggag    540
accatcatgg cggcgcgtag cctgggtatg cacgcgctga gcgttgagcc gtgccacatt    600
gacgaactga ccgcgcgtgc gagcagcggt cagctgcgtg atgcgcaact gatccgtcgt    660
attgtttgcg cgatgcacgg tccggctgtg agcgcggtgg ttagcggtag catcaccagc    720
agcggtccgc agaccgcgaa aattgaggaa ctgccgaccg cggcggacag ccacctgcgt    780
agcgcggcgc tgaccagcgc gcagcaattc tttctgaaag cgattgcgcc gcaccgtccg    840
gagaagccgt tcgttcaact gccgagcctg accagcgaag gtatccgtat ttatgacacc    900
ttcgcgcagt ttgtgatcgc ggatctgctg gacgataccc gtttcctgcc gatgcaaagc    960
ccgccgccga acggcctgat tacctttgtt aacccgagcg cgtacctggc ggacgatatc   1020
aaaaacggta acagccacat tgttccgggc gtgcagttct atgcgagcga cgcgtgcacc   1080
ctgatcgata ttccgcacga cctggatacc accagcgttg gtctgagcgt gctgcacaag   1140
tttggcaaag ttgacaagga taccctgaac aaggtgctgg atcgtatgct ggagcaagtt   1200
agcgaagacg atggtatcct gcaagtttac tttgacgtgg agcgtccgcg tattgatccg   1260
gtggttgtgg cgaacaccgt gttcctgttt cacctgggta acgtggcca cgaagttgcg    1320 cgtagcgaga agttcgttga aagcgtgctg ctgcagcgtg cgtacgagga aggcaccctg   1380
tactataacc tgggcgaagc gtttctggtt agcgtggcgc gtctggtgca cgagttcaaa   1440
gaacacttta cccgtagcgg tatgcgtcgt gcgctgagg aacgtctgcg tgagcgtgcg   1500
cgtgcgggta tgcaagaacg tgacgatgcg ctggcgctgg cgatgcgtat ccgtgcgtgc   1560
gcgctgtgcg gtctggcggg cgagggtctg accaaggcgg cggagcagga actgctgcgt   1620
ctgcaatgca agagcaaagg ttgctggggc tgccacccgt tctaccgtaa cggtagcaac   1680
gttctgagct ggatcggcag cgaagcgctg accaccgcgt atgcgattgc ggcgctgcag   1740
ccgatcgaca tttaa                                                    1755
```

<210> SEQ ID NO 11
<211> LENGTH: 7
<212> TYPE: PRT
<213> ORGANISM: Artificial Sequence
<220> FEATURE:
<223> OTHER INFORMATION: Synthesized, Modified class I motif:
      DSFDxx(D/E)
<220> FEATURE:
<221> NAME/KEY: MISC_FEATURE
<222> LOCATION: (5)..(6)
<223> OTHER INFORMATION: Xaa can be any naturally occurring amino acid
<220> FEATURE:
<221> NAME/KEY: MISC_FEATURE
<222> LOCATION: (7)..(7)
<223> OTHER INFORMATION: Xaa can be D or E

<400> SEQUENCE: 11

Asp Ser Phe Asp Xaa Xaa Xaa
1               5

<210> SEQ ID NO 12

```
<211> LENGTH: 6
<212> TYPE: PRT
<213> ORGANISM: Artificial Sequence
<220> FEATURE:
<223> OTHER INFORMATION: Synthesized, Modified class II motif:
      HDxD(T/S)T
<220> FEATURE:
<221> NAME/KEY: MISC_FEATURE
<222> LOCATION: (3)..(3)
<223> OTHER INFORMATION: Xaa can be any naturally occuring amino acid
<220> FEATURE:
<221> NAME/KEY: MISC_FEATURE
<222> LOCATION: (5)..(5)
<223> OTHER INFORMATION: Xaa can be T or S

<400> SEQUENCE: 12

His Asp Xaa Asp Xaa Thr
1               5

<210> SEQ ID NO 13
<211> LENGTH: 7
<212> TYPE: PRT
<213> ORGANISM: Artificial Sequence
<220> FEATURE:
<223> OTHER INFORMATION: Synthesized, Modified class I motif: DSFDSLE

<400> SEQUENCE: 13

Asp Ser Phe Asp Ser Leu Glu
1               5

<210> SEQ ID NO 14
<211> LENGTH: 5
<212> TYPE: PRT
<213> ORGANISM: Artificial Sequence
<220> FEATURE:
<223> OTHER INFORMATION: Synthesized, Modified class II motif: HDLDT

<400> SEQUENCE: 14

His Asp Leu Asp Thr
1               5

<210> SEQ ID NO 15
<211> LENGTH: 19
<212> TYPE: DNA
<213> ORGANISM: Artificial Sequence
<220> FEATURE:
<223> OTHER INFORMATION: Synthesized, forward primer 5' - 3'

<400> SEQUENCE: 15
atggagttct ctgcctctg                                                19

<210> SEQ ID NO 16
<211> LENGTH: 19
<212> TYPE: DNA
<213> ORGANISM: Artificial Sequence
<220> FEATURE:
<223> OTHER INFORMATION: Synthesized, reverse primer 5' - 3'

<400> SEQUENCE: 16
ggtttggctt atggaaggt                                                19

<210> SEQ ID NO 17
<211> LENGTH: 2496
<212> TYPE: DNA
<213> ORGANISM: Artificial Sequence
<220> FEATURE:
<223> OTHER INFORMATION: Synthesized, Codon-optimized sequence of DfHAD-
      6His-GST by Genscript genetic codon frequency of E. coli
<220> FEATURE:
```

```
<221> NAME/KEY: CDS
<222> LOCATION: (1)..(2496)

<400> SEQUENCE: 17 atg tct ggt tct cat cat cat cat cat cat agc agc ggt atg tcc cct        48
Met Ser Gly Ser His His His His His His Ser Ser Gly Met Ser Pro
1               5                   10                  15 ata cta ggt tat tgg aaa att aag ggc ctt gtg caa ccc act cga ctt        96
Ile Leu Gly Tyr Trp Lys Ile Lys Gly Leu Val Gln Pro Thr Arg Leu
            20                  25                  30 ctt ttg gaa tat ctt gaa gaa aaa tat gaa gag cat ttg tat gag cgc       144
Leu Leu Glu Tyr Leu Glu Glu Lys Tyr Glu Glu His Leu Tyr Glu Arg
        35                  40                  45 gat gaa ggt gat aaa tgg cga aac aaa aag ttt gaa ttg ggt ttg gag       192
Asp Glu Gly Asp Lys Trp Arg Asn Lys Lys Phe Glu Leu Gly Leu Glu
    50                  55                  60 ttt ccc aat ctt cct tat tat att gat ggt gat gtt aaa tta aca cag       240
Phe Pro Asn Leu Pro Tyr Tyr Ile Asp Gly Asp Val Lys Leu Thr Gln
65                  70                  75                  80 tct atg gcc atc ata cgt tat ata gct gac aag cac aac atg ttg ggt       288
Ser Met Ala Ile Ile Arg Tyr Ile Ala Asp Lys His Asn Met Leu Gly
                85                  90                  95 ggt tgt cca aaa gag cgt gca gag att tca atg ctt gaa gga gcg gtt       336
Gly Cys Pro Lys Glu Arg Ala Glu Ile Ser Met Leu Glu Gly Ala Val
            100                 105                 110 ttg gat att aga tac ggt gtt tcg aga att gca tat agt aaa gac ttt       384
Leu Asp Ile Arg Tyr Gly Val Ser Arg Ile Ala Tyr Ser Lys Asp Phe
        115                 120                 125 gaa act ctc aaa gtt gat ttt ctt agc aag cta cct gaa atg ctg aaa       432
Glu Thr Leu Lys Val Asp Phe Leu Ser Lys Leu Pro Glu Met Leu Lys
    130                 135                 140 atg ttc gaa gat cgt tta tgt cat aaa aca tat tta aat ggt gat cat       480
Met Phe Glu Asp Arg Leu Cys His Lys Thr Tyr Leu Asn Gly Asp His
145                 150                 155                 160 gta acc cat cct gac ttc atg ttg tat gac gct ctt gat gtt gtt tta       528
Val Thr His Pro Asp Phe Met Leu Tyr Asp Ala Leu Asp Val Val Leu
                165                 170                 175 tac atg gac cca atg tgc ctg gat gcg ttc cca aaa tta gtt tgt ttt       576
Tyr Met Asp Pro Met Cys Leu Asp Ala Phe Pro Lys Leu Val Cys Phe
            180                 185                 190 aaa aaa cgt att gaa gct atc cca caa att gat aag tac ttg aaa tcc       624
Lys Lys Arg Ile Glu Ala Ile Pro Gln Ile Asp Lys Tyr Leu Lys Ser
        195                 200                 205 agc aag tat ata gca tgg cct ttg cag ggc tgg caa gcc acg ttt ggt       672
Ser Lys Tyr Ile Ala Trp Pro Leu Gln Gly Trp Gln Ala Thr Phe Gly
    210                 215                 220 ggt ggc gac cat cct cca aaa tcg gat ctg ggc cac aca ggc cat aga       720
Gly Gly Asp His Pro Pro Lys Ser Asp Leu Gly His Thr Gly His Arg
225                 230                 235                 240 tct gac gac gac gac aag cat atg gag ttc agc gcg agc gct ccg ccg       768
Ser Asp Asp Asp Asp Lys His Met Glu Phe Ser Ala Ser Ala Pro Pro
                245                 250                 255 ccg cgt ctg gcg agc gtg atc att ctg gaa ccg ctg ggt ttt ctg ctg       816
Pro Arg Leu Ala Ser Val Ile Ile Leu Glu Pro Leu Gly Phe Leu Leu
            260                 265                 270 acc ccg cac tac agc agc cag ctg ccg aag aaa ctg ctg cgt cgt ctg       864
Thr Pro His Tyr Ser Ser Gln Leu Pro Lys Lys Leu Leu Arg Arg Leu
        275                 280                 285 ctg tgc acc cgt atc tgg cac cgt tat cag cgt ggc ctg cgt ctg           912
Leu Cys Thr Arg Ile Trp His Arg Tyr Gln Arg Gly Arg Leu Arg Leu
```

-continued

```
                 290                 295                 300
cgt gac gcg gcg atg ctg ctg gcg caa ctg ccg ttc ctg gcg gtt agc          960
Arg Asp Ala Ala Met Leu Leu Ala Gln Leu Pro Phe Leu Ala Val Ser
305                 310                 315                 320 gac cac ccg tgg gcg ctg gat aac ctg gcg agc ctg ctg cgt ccg acc         1008
Asp His Pro Trp Ala Leu Asp Asn Leu Ala Ser Leu Leu Arg Pro Thr
                325                 330                 335 gcg gtt cgt gcg gtg ccg tgg atg ctg ctg ctg gac ttt ctg cgt             1056
Ala Val Arg Ala Val Pro Trp Met Leu Leu Leu Asp Phe Leu Arg
        340                 345                 350 gat gag ctg cac ctg aaa gtg gtt tgc gcg acc aac agc agc ccg gag         1104
Asp Glu Leu His Leu Lys Val Val Cys Ala Thr Asn Ser Ser Pro Glu
    355                 360                 365 gaa ctg cag gaa ctg cgt cac caa ttc ccg gcg ctg ttt gcg aag gtt         1152
Glu Leu Gln Glu Leu Arg His Gln Phe Pro Ala Leu Phe Ala Lys Val
370                 375                 380 gac gcg acc gtg agc agc ggc gag gaa ggt gtt ggc aaa ccg agc gtg         1200
Asp Ala Thr Val Ser Ser Gly Glu Glu Gly Val Gly Lys Pro Ser Val
385                 390                 395                 400 cgt ttc ctg caa gcg gcg ctg gat aag gcg ggc gtg cac gcg cag caa         1248
Arg Phe Leu Gln Ala Ala Leu Asp Lys Ala Gly Val His Ala Gln Gln
                405                 410                 415 acc ctg tac ctg gac agc ttt gat agc ctg gag acc atc atg gcg gcg         1296
Thr Leu Tyr Leu Asp Ser Phe Asp Ser Leu Glu Thr Ile Met Ala Ala
        420                 425                 430 cgt agc ctg ggt atg cac gcg ctg agc gtt gag ccg tgc cac att gac         1344
Arg Ser Leu Gly Met His Ala Leu Ser Val Glu Pro Cys His Ile Asp
    435                 440                 445 gaa ctg acc gcg cgt gcg agc agc ggt cag ctg cgt gat gcg caa ctg         1392
Glu Leu Thr Ala Arg Ala Ser Ser Gly Gln Leu Arg Asp Ala Gln Leu
450                 455                 460 atc cgt cgt att gtt tgc gcg atg cac ggt ccg gct gtg agc gcg gtg         1440
Ile Arg Arg Ile Val Cys Ala Met His Gly Pro Ala Val Ser Ala Val
465                 470                 475                 480 gtt agc ggt agc atc acc agc agc ggt ccg cag acc gcg aaa att gag         1488
Val Ser Gly Ser Ile Thr Ser Ser Gly Pro Gln Thr Ala Lys Ile Glu
                485                 490                 495 gaa ctg ccg acc gcg gcg gac agc cac ctg cgt agc gcg gcg ctg acc         1536
Glu Leu Pro Thr Ala Ala Asp Ser His Leu Arg Ser Ala Ala Leu Thr
        500                 505                 510 agc gcg cag caa ttc ttt ctg aaa gtg att gcg ccg cac cgt ccg gag         1584
Ser Ala Gln Gln Phe Phe Leu Lys Val Ile Ala Pro His Arg Pro Glu
    515                 520                 525 aag ccg ttc gtt caa ctg ccg agc ctg acc agc gaa ggt atc cgt att         1632
Lys Pro Phe Val Gln Leu Pro Ser Leu Thr Ser Glu Gly Ile Arg Ile
530                 535                 540 tat gac acc ttc gcg cag ttt gtg atc gcg gat ctg ctg gac gat acc         1680
Tyr Asp Thr Phe Ala Gln Phe Val Ile Ala Asp Leu Leu Asp Asp Thr
545                 550                 555                 560 cgt ttc ctg ccg atg caa agc ccg ccg ccg aac ggc ctg att acc ttt         1728
Arg Phe Leu Pro Met Gln Ser Pro Pro Pro Asn Gly Leu Ile Thr Phe
                565                 570                 575 gtt aac ccg agc gcg tac ctg gcg gac gat atc aaa aac ggt aac agc         1776
Val Asn Pro Ser Ala Tyr Leu Ala Asp Asp Ile Lys Asn Gly Asn Ser
        580                 585                 590 cac att gtt ccg ggc gtg cag ttc tat gcg agc gac gcg tgc acc ctg         1824
His Ile Val Pro Gly Val Gln Phe Tyr Ala Ser Asp Ala Cys Thr Leu
    595                 600                 605 atc gat att ccg cac gac ctg gat acc acc agc gtt ggt ctg agc gtg         1872
```

```
Ile Asp Ile Pro His Asp Leu Asp Thr Thr Ser Val Gly Leu Ser Val
        610             615                 620 ctg cac aag ttt ggc aaa gtt gac aag gat acc ctg aac aag gtg ctg      1920
Leu His Lys Phe Gly Lys Val Asp Lys Asp Thr Leu Asn Lys Val Leu
625                 630                 635                 640 gat cgt atg ctg gag caa gtt agc gaa gac gat ggt atc ctg caa gtt      1968
Asp Arg Met Leu Glu Gln Val Ser Glu Asp Asp Gly Ile Leu Gln Val
                645                 650                 655 tac ttt gac gtg gag cgt ccg cgt att gat ccg gtg gtt gtg gcg aac      2016
Tyr Phe Asp Val Glu Arg Pro Arg Ile Asp Pro Val Val Val Ala Asn
            660                 665                 670 acc gtg ttc ctg ttt cac ctg ggt aaa cgt ggc cac gaa gtt gcg cgt      2064
Thr Val Phe Leu Phe His Leu Gly Lys Arg Gly His Glu Val Ala Arg
        675                 680                 685 agc gag aag ttc gtt gaa agc gtg ctg ctg cag cgt gcg tac gag gaa      2112
Ser Glu Lys Phe Val Glu Ser Val Leu Leu Gln Arg Ala Tyr Glu Glu
    690                 695                 700 ggc acc ctg tac tat aac ctg ggc gaa gcg ttt ctg gtt agc gtg gcg      2160
Gly Thr Leu Tyr Tyr Asn Leu Gly Glu Ala Phe Leu Val Ser Val Ala
705                 710                 715                 720 cgt ctg gtg cac gag ttc aaa gaa cac ttt acc cgt agc ggt atg cgt      2208
Arg Leu Val His Glu Phe Lys Glu His Phe Thr Arg Ser Gly Met Arg
                725                 730                 735 cgt gcg ctg gag gaa cgt ctg cgt gag cgt gcg cgt gcg ggt atg caa      2256
Arg Ala Leu Glu Glu Arg Leu Arg Glu Arg Ala Arg Ala Gly Met Gln
            740                 745                 750 gaa cgt gac gat gcg ctg gcg ctg gcg atg cgt atc cgt gcg tgc gcg      2304
Glu Arg Asp Asp Ala Leu Ala Leu Ala Met Arg Ile Arg Ala Cys Ala
        755                 760                 765 ctg tgc ggt ctg gcg ggc gag ggt ctg acc aag gcg gcg gag cag gaa      2352
Leu Cys Gly Leu Ala Gly Glu Gly Leu Thr Lys Ala Ala Glu Gln Glu
    770                 775                 780 ctg ctg cgt ctg caa tgc aag agc aaa ggt tgc tgg ggc tgc cac ccg      2400
Leu Leu Arg Leu Gln Cys Lys Ser Lys Gly Cys Trp Gly Cys His Pro
785                 790                 795                 800 ttc tac cgt aac ggt agc aac gtt ctg agc tgg atc ggc agc gaa gcg      2448
Phe Tyr Arg Asn Gly Ser Asn Val Leu Ser Trp Ile Gly Ser Glu Ala
                805                 810                 815 ctg acc acc gcg tat gcg att gcg gcg ctg cag ccg atc gac att taa      2496
Leu Thr Thr Ala Tyr Ala Ile Ala Ala Leu Gln Pro Ile Asp Ile
            820                 825                 830

<210> SEQ ID NO 18
<211> LENGTH: 831
<212> TYPE: PRT
<213> ORGANISM: Artificial Sequence
<220> FEATURE:
<223> OTHER INFORMATION: Synthesized, Codon-optimized sequence of DfHAD-
      6His-GST by Genscript genetic codon frequency of E. coli

<400> SEQUENCE: 18

Met Ser Gly Ser His His His His His Ser Ser Gly Met Ser Pro
1               5                   10                  15

Ile Leu Gly Tyr Trp Lys Ile Lys Gly Leu Val Gln Pro Thr Arg Leu
            20                  25                  30

Leu Leu Glu Tyr Leu Glu Glu Lys Tyr Glu Glu His Leu Tyr Glu Arg
        35                  40                  45

Asp Glu Gly Asp Lys Trp Arg Asn Lys Lys Phe Glu Leu Gly Leu Glu
    50                  55                  60

Phe Pro Asn Leu Pro Tyr Tyr Ile Asp Gly Asp Val Lys Leu Thr Gln
```

```
            65                  70                  75                  80
Ser Met Ala Ile Ile Arg Tyr Ile Ala Asp Lys His Asn Met Leu Gly
                85                  90                  95

Gly Cys Pro Lys Glu Arg Ala Glu Ile Ser Met Leu Glu Gly Ala Val
               100                 105                 110

Leu Asp Ile Arg Tyr Gly Val Ser Arg Ile Ala Tyr Ser Lys Asp Phe
               115                 120                 125

Glu Thr Leu Lys Val Asp Phe Leu Ser Lys Leu Pro Glu Met Leu Lys
           130                 135                 140

Met Phe Glu Asp Arg Leu Cys His Lys Thr Tyr Leu Asn Gly Asp His
145                 150                 155                 160

Val Thr His Pro Asp Phe Met Leu Tyr Asp Ala Leu Asp Val Val Leu
               165                 170                 175

Tyr Met Asp Pro Met Cys Leu Asp Ala Phe Pro Lys Leu Val Cys Phe
               180                 185                 190

Lys Lys Arg Ile Glu Ala Ile Pro Gln Ile Asp Lys Tyr Leu Lys Ser
               195                 200                 205

Ser Lys Tyr Ile Ala Trp Pro Leu Gln Gly Trp Gln Ala Thr Phe Gly
           210                 215                 220

Gly Gly Asp His Pro Pro Lys Ser Asp Leu Gly His Thr Gly His Arg
225                 230                 235                 240

Ser Asp Asp Asp Lys His Met Glu Phe Ser Ala Ser Ala Pro Pro
               245                 250                 255

Pro Arg Leu Ala Ser Val Ile Ile Leu Glu Pro Leu Gly Phe Leu Leu
               260                 265                 270

Thr Pro His Tyr Ser Ser Gln Leu Pro Lys Lys Leu Leu Arg Arg Leu
           275                 280                 285

Leu Cys Thr Arg Ile Trp His Arg Tyr Gln Arg Gly Arg Leu Arg Leu
           290                 295                 300

Arg Asp Ala Ala Met Leu Leu Ala Gln Leu Pro Phe Leu Ala Val Ser
305                 310                 315                 320

Asp His Pro Trp Ala Leu Asp Asn Leu Ala Ser Leu Leu Arg Pro Thr
               325                 330                 335

Ala Val Arg Ala Val Pro Trp Met Leu Leu Leu Asp Phe Leu Arg
               340                 345                 350

Asp Glu Leu His Leu Lys Val Val Cys Ala Thr Asn Ser Ser Pro Glu
           355                 360                 365

Glu Leu Gln Glu Leu Arg His Gln Phe Pro Ala Leu Phe Ala Lys Val
           370                 375                 380

Asp Ala Thr Val Ser Ser Gly Glu Glu Gly Val Gly Lys Pro Ser Val
385                 390                 395                 400

Arg Phe Leu Gln Ala Ala Leu Asp Lys Ala Gly Val His Ala Gln Gln
               405                 410                 415

Thr Leu Tyr Leu Asp Ser Phe Asp Ser Leu Glu Thr Ile Met Ala Ala
           420                 425                 430

Arg Ser Leu Gly Met His Ala Leu Ser Val Glu Pro Cys His Ile Asp
           435                 440                 445

Glu Leu Thr Ala Arg Ala Ser Ser Gly Gln Leu Arg Asp Ala Gln Leu
           450                 455                 460

Ile Arg Arg Ile Val Cys Ala Met His Gly Pro Ala Val Ser Ala Val
465                 470                 475                 480

Val Ser Gly Ser Ile Thr Ser Ser Gly Pro Gln Thr Ala Lys Ile Glu
               485                 490                 495
```

Glu Leu Pro Thr Ala Ala Asp Ser His Leu Arg Ser Ala Ala Leu Thr
            500                 505                 510

Ser Ala Gln Gln Phe Phe Leu Lys Val Ile Ala Pro His Arg Pro Glu
        515                 520                 525

Lys Pro Phe Val Gln Leu Pro Ser Leu Thr Ser Glu Gly Ile Arg Ile
530                 535                 540

Tyr Asp Thr Phe Ala Gln Phe Val Ile Ala Asp Leu Leu Asp Asp Thr
545                 550                 555                 560

Arg Phe Leu Pro Met Gln Ser Pro Pro Asn Gly Leu Ile Thr Phe
                565                 570                 575

Val Asn Pro Ser Ala Tyr Leu Ala Asp Asp Ile Lys Asn Gly Asn Ser
            580                 585                 590

His Ile Val Pro Gly Val Gln Phe Tyr Ala Ser Asp Ala Cys Thr Leu
        595                 600                 605

Ile Asp Ile Pro His Asp Leu Asp Thr Thr Ser Val Gly Leu Ser Val
610                 615                 620

Leu His Lys Phe Gly Lys Val Asp Lys Asp Thr Leu Asn Lys Val Leu
625                 630                 635                 640

Asp Arg Met Leu Glu Gln Val Ser Glu Asp Asp Gly Ile Leu Gln Val
                645                 650                 655

Tyr Phe Asp Val Glu Arg Pro Arg Ile Asp Pro Val Val Val Ala Asn
            660                 665                 670

Thr Val Phe Leu Phe His Leu Gly Lys Arg Gly His Glu Val Ala Arg
        675                 680                 685

Ser Glu Lys Phe Val Glu Ser Val Leu Leu Gln Arg Ala Tyr Glu Glu
690                 695                 700

Gly Thr Leu Tyr Tyr Asn Leu Gly Glu Ala Phe Leu Val Ser Val Ala
705                 710                 715                 720

Arg Leu Val His Glu Phe Lys Glu His Phe Thr Arg Ser Gly Met Arg
                725                 730                 735

Arg Ala Leu Glu Glu Arg Leu Arg Glu Arg Ala Arg Ala Gly Met Gln
            740                 745                 750

Glu Arg Asp Asp Ala Leu Ala Leu Ala Met Arg Ile Arg Ala Cys Ala
        755                 760                 765

Leu Cys Gly Leu Ala Gly Glu Gly Leu Thr Lys Ala Ala Glu Gln Glu
770                 775                 780

Leu Leu Arg Leu Gln Cys Lys Ser Lys Gly Cys Trp Gly Cys His Pro
785                 790                 795                 800

Phe Tyr Arg Asn Gly Ser Asn Val Leu Ser Trp Ile Gly Ser Glu Ala
                805                 810                 815

Leu Thr Thr Ala Tyr Ala Ile Ala Ala Leu Gln Pro Ile Asp Ile
            820                 825                 830

<210> SEQ ID NO 19
<211> LENGTH: 583
<212> TYPE: PRT
<213> ORGANISM: Artificial Sequence
<220> FEATURE:
<223> OTHER INFORMATION: Synthesized, DfHAD-QW fungal

<400> SEQUENCE: 19

Met Glu Phe Ser Ala Ser Ala Pro Pro Arg Leu Ala Ser Val Ile
1               5                   10                  15

Ile Leu Glu Pro Leu Gly Phe Leu Leu Thr Pro His Tyr Ser Ser Gln
            20                  25                  30

```
Leu Pro Lys Lys Leu Leu Arg Arg Leu Leu Cys Thr Arg Ile Trp His
        35                  40                  45
Arg Tyr Gln Arg Gly Arg Leu Arg Leu Arg Asp Ala Ala Met Leu Leu
    50                  55                  60
Ala Gln Leu Pro Phe Leu Ala Val Ser Asp His Pro Trp Ala Leu Asp
65                  70                  75                  80
Asn Leu Ala Ser Leu Leu Arg Pro Thr Ala Val Arg Ala Val Pro Trp
                85                  90                  95
Met Leu Leu Leu Leu Asp Phe Leu Arg Asp Glu Leu His Leu Lys Val
            100                 105                 110
Val Cys Ala Thr Asn Ser Ser Pro Glu Glu Leu Gln Glu Leu Arg His
            115                 120                 125
Gln Phe Pro Ala Leu Phe Ala Lys Val Asp Ala Thr Val Ser Ser Gly
        130                 135                 140
Glu Glu Gly Val Gly Lys Pro Ser Val Arg Phe Leu Gln Ala Ala Leu
145                 150                 155                 160
Asp Lys Ala Gly Val His Ala Gln Gln Thr Leu Tyr Leu Asp Ser Phe
                165                 170                 175
Asp Ser Leu Glu Thr Ile Met Ala Ala Arg Ser Leu Gly Met His Ala
            180                 185                 190
Leu Ser Val Glu Pro Cys His Ile Asp Glu Leu Thr Ala Arg Ala Ser
        195                 200                 205
Ser Gly Gln Leu Arg Asp Ala Gln Leu Ile Arg Arg Ile Val Cys Ala
        210                 215                 220
Met His Gly Pro Ala Val Ser Ala Val Val Ser Gly Ser Ile Thr Ser
225                 230                 235                 240
Ser Gly Pro Gln Thr Ala Lys Ile Glu Glu Leu Pro Thr Ala Ala Asp
                245                 250                 255
Ser His Leu Arg Ser Ala Ala Leu Thr Ser Ala Gln Gln Phe Phe Leu
            260                 265                 270
Lys Val Ile Ala Pro His Arg Pro Glu Lys Pro Phe Val Gln Leu Pro
        275                 280                 285
Ser Leu Thr Ser Glu Gly Ile Arg Ile Tyr Asp Thr Phe Ala Gln Phe
        290                 295                 300
Val Ile Ala Asp Leu Leu Asp Asp Thr Arg Phe Leu Pro Met Gln Ser
305                 310                 315                 320
Pro Pro Pro Asn Gly Leu Ile Thr Phe Val Asn Pro Ser Ala Tyr Leu
                325                 330                 335
Ala Asp Asp Ile Lys Asn Gly Asn Ser His Ile Val Pro Gly Val Gln
            340                 345                 350
Phe Tyr Ala Ser Asp Ala Cys Thr Leu Ile Asp Ile Pro His Asp Leu
        355                 360                 365
Asp Thr Thr Ser Val Gly Leu Ser Val Leu His Lys Phe Gly Lys Val
        370                 375                 380
Asp Lys Asp Thr Leu Asn Lys Val Leu Asp Arg Met Leu Glu Gln Val
385                 390                 395                 400
Ser Glu Asp Asp Gly Ile Leu Gln Val Tyr Phe Asp Val Glu Arg Pro
                405                 410                 415
Arg Ile Asp Pro Val Val Val Ala Asn Thr Val Phe Leu Phe His Leu
            420                 425                 430
Gly Lys Arg Gly His Glu Val Ala Arg Ser Lys Phe Val Glu Ser
        435                 440                 445
```

Val Leu Leu Gln Arg Ala Tyr Glu Glu Gly Thr Leu Tyr Tyr Asn Leu
         450                 455                 460

Gly Glu Ala Phe Leu Val Ser Val Ala Arg Leu Val His Glu Phe Lys
465                 470                 475                 480

Glu His Phe Thr Arg Ser Gly Met Arg Ala Leu Glu Glu Arg Leu
                485                 490                 495

Arg Glu Arg Ala Arg Ala Gly Met Gln Glu Arg Asp Asp Ala Leu Ala
                500                 505                 510

Leu Ala Met Arg Ile Arg Ala Cys Ala Leu Cys Gly Leu Ala Gly Glu
                515                 520                 525

Gly Leu Thr Lys Ala Ala Glu Gln Glu Leu Leu Arg Leu Gln Cys Glu
530                 535                 540

Asp Gly Gly Trp Gly Cys His Pro Phe Tyr Arg Asn Gly Ser Asn Val
545                 550                 555                 560

Leu Ser Trp Ile Gly Ser Glu Ala Leu Thr Thr Ala Tyr Ala Ile Ala
                565                 570                 575

Ala Leu Gln Pro Ile Asp Ile
                580

<210> SEQ ID NO 20
<211> LENGTH: 584
<212> TYPE: PRT
<213> ORGANISM: Artificial Sequence
<220> FEATURE:
<223> OTHER INFORMATION: Synthesized, DfHAD-QW mut

<400> SEQUENCE: 20

Met Glu Phe Ser Ala Ser Ala Pro Pro Arg Leu Ala Ser Val Ile
1               5                   10                  15

Ile Leu Glu Pro Leu Gly Phe Leu Leu Thr Pro His Tyr Ser Ser Gln
                20                  25                  30

Leu Pro Lys Lys Leu Leu Arg Arg Leu Cys Thr Arg Ile Trp His
            35                  40                  45

Arg Tyr Gln Arg Gly Arg Leu Arg Leu Arg Asp Ala Ala Met Leu Leu
    50                  55                  60

Ala Gln Leu Pro Phe Leu Ala Val Ser Asp His Pro Trp Ala Leu Asp
65                  70                  75                  80

Asn Leu Ala Ser Leu Leu Arg Pro Thr Ala Val Arg Ala Val Pro Trp
                85                  90                  95

Met Leu Leu Leu Leu Asp Phe Leu Arg Asp Glu Leu His Leu Lys Val
                100                 105                 110

Val Cys Ala Thr Asn Ser Ser Pro Glu Glu Leu Gln Glu Leu Arg His
            115                 120                 125

Gln Phe Pro Ala Leu Phe Ala Lys Val Asp Ala Thr Val Ser Ser Gly
    130                 135                 140

Glu Glu Gly Val Gly Lys Pro Ser Val Arg Phe Leu Gln Ala Ala Leu
145                 150                 155                 160

Asp Lys Ala Gly Val His Ala Gln Gln Thr Leu Tyr Leu Asp Ser Phe
                165                 170                 175

Asp Ser Leu Glu Thr Ile Met Ala Ala Arg Ser Leu Gly Met His Ala
            180                 185                 190

Leu Ser Val Glu Pro Cys His Ile Asp Glu Leu Thr Ala Arg Ala Ser
        195                 200                 205

Ser Gly Gln Leu Arg Asp Ala Gln Leu Ile Arg Arg Ile Val Cys Ala
    210                 215                 220

Met His Gly Pro Ala Val Ser Ala Val Val Ser Gly Ser Ile Thr Ser
225                 230                 235                 240

Ser Gly Pro Gln Thr Ala Lys Ile Glu Glu Leu Pro Thr Ala Ala Asp
            245                 250                 255

Ser His Leu Arg Ser Ala Ala Leu Thr Ser Ala Gln Gln Phe Phe Leu
            260                 265                 270

Lys Val Ile Ala Pro His Arg Pro Glu Lys Pro Phe Val Gln Leu Pro
            275                 280                 285

Ser Leu Thr Ser Glu Gly Ile Arg Ile Tyr Asp Thr Phe Ala Gln Phe
            290                 295                 300

Val Ile Ala Asp Leu Leu Asp Asp Thr Arg Phe Leu Pro Met Gln Ser
305                 310                 315                 320

Pro Pro Pro Asn Gly Leu Ile Thr Phe Val Asn Pro Ser Ala Tyr Leu
            325                 330                 335

Ala Asp Asp Ile Lys Asn Gly Asn Ser His Ile Val Pro Gly Val Gln
            340                 345                 350

Phe Tyr Ala Ser Asp Ala Cys Thr Leu Ile Asp Ile Pro His Asp Leu
            355                 360                 365

Asp Thr Thr Ser Val Gly Leu Ser Val Leu His Lys Phe Gly Lys Val
            370                 375                 380

Asp Lys Asp Thr Leu Asn Lys Val Leu Asp Arg Met Leu Glu Gln Val
385                 390                 395                 400

Ser Glu Asp Asp Gly Ile Leu Gln Val Tyr Phe Asp Val Glu Arg Pro
            405                 410                 415

Arg Ile Asp Pro Val Val Val Ala Asn Thr Val Phe Leu Phe His Leu
            420                 425                 430

Gly Lys Arg Gly His Glu Val Ala Arg Ser Glu Lys Phe Val Glu Ser
            435                 440                 445

Val Leu Leu Gln Arg Ala Tyr Glu Glu Gly Thr Leu Tyr Tyr Asn Leu
450                 455                 460

Gly Glu Ala Phe Leu Val Ser Val Ala Arg Leu Val His Glu Phe Lys
465                 470                 475                 480

Glu His Phe Thr Arg Ser Gly Met Arg Arg Ala Leu Glu Glu Arg Leu
            485                 490                 495

Arg Glu Arg Ala Arg Ala Gly Met Gln Glu Arg Asp Asp Ala Leu Ala
            500                 505                 510

Leu Ala Met Arg Ile Arg Ala Cys Ala Leu Cys Gly Leu Ala Gly Glu
            515                 520                 525

Gly Leu Thr Lys Ala Ala Glu Gln Glu Leu Leu Arg Leu Gln Cys Ala
530                 535                 540

Ala Ala Gly Cys Trp Gly Cys His Pro Phe Tyr Arg Asn Gly Ser Asn
545                 550                 555                 560

Val Leu Ser Trp Ile Gly Ser Glu Ala Leu Thr Thr Ala Tyr Ala Ile
            565                 570                 575

Ala Ala Leu Gln Pro Ile Asp Ile
            580

<210> SEQ ID NO 21
<211> LENGTH: 584
<212> TYPE: PRT
<213> ORGANISM: Artificial Sequence
<220> FEATURE:
<223> OTHER INFORMATION: Synthesized, DfHAD-SEQ64motif

<400> SEQUENCE: 21

```
Met Glu Phe Ser Ala Ser Ala Pro Pro Arg Leu Ala Ser Val Ile
1               5                   10                  15

Ile Leu Glu Pro Leu Gly Phe Leu Leu Thr Pro His Tyr Ser Ser Gln
                20                  25                  30

Leu Pro Lys Lys Leu Leu Arg Arg Leu Leu Cys Thr Arg Ile Trp His
            35                  40                  45

Arg Tyr Gln Arg Gly Arg Leu Arg Leu Arg Asp Ala Ala Met Leu Leu
        50                  55                  60

Ala Gln Leu Pro Phe Leu Ala Val Ser Asp His Pro Trp Ala Leu Asp
65                  70                  75                  80

Asn Leu Ala Ser Leu Leu Arg Pro Thr Ala Val Arg Ala Val Pro Trp
                85                  90                  95

Met Leu Leu Leu Leu Asp Phe Leu Arg Asp Glu Leu His Leu Lys Val
                100                 105                 110

Val Cys Ala Thr Asn Ser Ser Pro Glu Glu Leu Gln Glu Leu Arg His
            115                 120                 125

Gln Phe Pro Ala Leu Phe Ala Lys Val Asp Ala Thr Val Ser Ser Gly
        130                 135                 140

Glu Glu Gly Val Gly Lys Pro Ser Val Arg Phe Leu Gln Ala Ala Leu
145                 150                 155                 160

Asp Lys Ala Gly Val His Ala Gln Gln Thr Leu Tyr Leu Asp Ser Phe
                165                 170                 175

Asp Pro Leu Glu Thr Ile Met Ala Ala Arg Ser Leu Gly Met His Ala
                180                 185                 190

Leu Ser Val Glu Pro Cys His Ile Asp Glu Leu Thr Ala Arg Ala Ser
            195                 200                 205

Ser Gly Gln Leu Arg Asp Ala Gln Leu Ile Arg Arg Ile Val Cys Ala
        210                 215                 220

Met His Gly Pro Ala Val Ser Ala Val Val Ser Gly Ser Ile Thr Ser
225                 230                 235                 240

Ser Gly Pro Gln Thr Ala Lys Ile Glu Glu Leu Pro Thr Ala Ala Asp
                245                 250                 255

Ser His Leu Arg Ser Ala Ala Leu Thr Ser Ala Gln Gln Phe Phe Leu
                260                 265                 270

Lys Val Ile Ala Pro His Arg Pro Glu Lys Pro Phe Val Gln Leu Pro
            275                 280                 285

Ser Leu Thr Ser Glu Gly Ile Arg Ile Tyr Asp Thr Phe Ala Gln Phe
        290                 295                 300

Val Ile Ala Asp Leu Leu Asp Asp Thr Arg Phe Leu Pro Met Gln Ser
305                 310                 315                 320

Pro Pro Pro Asn Gly Leu Ile Thr Phe Val Asn Pro Ser Ala Tyr Leu
                325                 330                 335

Ala Asp Asp Ile Lys Asn Gly Asn Ser His Ile Val Pro Gly Val Gln
                340                 345                 350

Phe Tyr Ala Ser Asp Ala Cys Thr Leu Ile Asp Ile Pro His Asp Leu
            355                 360                 365

Asp Thr Thr Ser Val Gly Leu Ser Val Leu His Lys Phe Gly Lys Val
        370                 375                 380

Asp Lys Asp Thr Leu Asn Lys Val Leu Asp Arg Met Leu Glu Gln Val
385                 390                 395                 400

Ser Glu Asp Asp Gly Ile Leu Gln Val Tyr Phe Asp Val Glu Arg Pro
                405                 410                 415

Arg Ile Asp Pro Val Val Val Ala Asn Thr Val Phe Leu Phe His Leu
```

```
                     420                 425                 430
Gly Lys Arg Gly His Glu Val Ala Arg Ser Glu Lys Phe Val Glu Ser
            435                 440                 445

Val Leu Leu Gln Arg Ala Tyr Glu Glu Gly Thr Leu Tyr Tyr Asn Leu
    450                 455                 460

Gly Glu Ala Phe Leu Val Ser Val Ala Arg Leu Val His Glu Phe Lys
465                 470                 475                 480

Glu His Phe Thr Arg Ser Gly Met Arg Arg Ala Leu Glu Glu Arg Leu
                485                 490                 495

Arg Glu Arg Ala Arg Ala Gly Met Gln Glu Arg Asp Asp Ala Leu Ala
            500                 505                 510

Leu Ala Met Arg Ile Arg Ala Cys Ala Leu Cys Gly Leu Ala Gly Glu
        515                 520                 525

Gly Leu Thr Lys Ala Ala Glu Gln Glu Leu Leu Arg Leu Gln Cys Lys
    530                 535                 540

Ser Lys Gly Cys Trp Gly Cys His Pro Phe Tyr Arg Asn Gly Ser Asn
545                 550                 555                 560

Val Leu Ser Trp Ile Gly Ser Glu Ala Leu Thr Thr Ala Tyr Ala Ile
                565                 570                 575

Ala Ala Leu Gln Pro Ile Asp Ile
            580

<210> SEQ ID NO 22
<211> LENGTH: 584
<212> TYPE: PRT
<213> ORGANISM: Artificial Sequence
<220> FEATURE:
<223> OTHER INFORMATION: Synthesized, DfHAD-MOSmotif

<400> SEQUENCE: 22

Met Glu Phe Ser Ala Ser Ala Pro Pro Arg Leu Ala Ser Val Ile
1               5                   10                  15

Ile Leu Glu Pro Leu Gly Phe Leu Leu Thr Pro His Tyr Ser Ser Gln
                20                  25                  30

Leu Pro Lys Lys Leu Leu Arg Arg Leu Leu Cys Thr Arg Ile Trp His
            35                  40                  45

Arg Tyr Gln Arg Gly Arg Leu Arg Leu Arg Asp Ala Ala Met Leu Leu
    50                  55                  60

Ala Gln Leu Pro Phe Leu Ala Val Ser Asp His Pro Trp Ala Leu Asp
65                  70                  75                  80

Asn Leu Ala Ser Leu Leu Arg Pro Thr Ala Val Arg Ala Val Pro Trp
                85                  90                  95

Met Leu Leu Leu Leu Asp Phe Leu Arg Asp Glu Leu His Leu Lys Val
            100                 105                 110

Val Cys Ala Thr Asn Ser Ser Pro Glu Glu Leu Gln Glu Leu Arg His
        115                 120                 125

Gln Phe Pro Ala Leu Phe Ala Lys Val Asp Ala Thr Val Ser Ser Gly
    130                 135                 140

Glu Glu Gly Val Gly Lys Pro Ser Val Arg Phe Leu Gln Ala Ala Leu
145                 150                 155                 160

Asp Lys Ala Gly Val His Ala Gln Gln Thr Leu Tyr Leu Asp Ser Phe
                165                 170                 175

Asp Ser Leu Glu Thr Ile Met Ala Ala Arg Ser Leu Gly Met His Ala
            180                 185                 190

Leu Ser Val Glu Pro Cys His Ile Asp Glu Leu Thr Ala Arg Ala Ser
```

```
                195                 200                 205
Ser Gly Gln Leu Arg Asp Ala Gln Leu Ile Arg Ile Val Cys Ala
210                 215                 220

Met His Gly Pro Ala Val Ser Ala Val Val Ser Gly Ser Ile Thr Ser
225                 230                 235                 240

Ser Gly Pro Gln Thr Ala Lys Ile Glu Glu Leu Pro Thr Ala Ala Asp
                245                 250                 255

Ser His Leu Arg Ser Ala Ala Leu Thr Ser Ala Gln Gln Phe Phe Leu
                260                 265                 270

Lys Val Ile Ala Pro His Arg Pro Glu Lys Pro Phe Val Gln Leu Pro
                275                 280                 285

Ser Leu Thr Ser Glu Gly Ile Arg Ile Tyr Asp Thr Phe Ala Gln Phe
                290                 295                 300

Val Ile Ala Asp Leu Leu Asp Asp Thr Arg Phe Leu Pro Met Gln Ser
305                 310                 315                 320

Pro Pro Pro Asn Gly Leu Ile Thr Phe Val Asn Pro Ser Ala Tyr Leu
                325                 330                 335

Ala Asp Asp Ile Lys Asn Gly Asn Ser His Ile Val Pro Gly Val Gln
                340                 345                 350

Phe Tyr Ala Ser Asp Ala Cys Thr Leu Ile Asp Ile Pro His Asp Leu
                355                 360                 365

Asp Thr Thr Ser Val Gly Leu Ser Val Leu His Lys Phe Gly Lys Val
370                 375                 380

Asp Lys Asp Thr Leu Asn Lys Val Leu Asp Arg Met Leu Glu Gln Val
385                 390                 395                 400

Ser Glu Asp Asp Gly Ile Leu Gln Val Ala Ala Val Glu Arg Pro
                405                 410                 415

Arg Ile Asp Pro Val Val Ala Asn Thr Val Phe Leu Phe His Leu
                420                 425                 430

Gly Lys Arg Gly His Glu Val Ala Arg Ser Glu Lys Phe Val Glu Ser
                435                 440                 445

Val Leu Leu Gln Arg Ala Tyr Glu Glu Gly Thr Leu Tyr Tyr Asn Leu
450                 455                 460

Gly Glu Ala Phe Leu Val Ser Val Ala Arg Leu Val His Glu Phe Lys
465                 470                 475                 480

Glu His Phe Thr Arg Ser Gly Met Arg Arg Ala Leu Glu Glu Arg Leu
                485                 490                 495

Arg Glu Arg Ala Arg Ala Gly Met Gln Glu Arg Asp Asp Ala Leu Ala
                500                 505                 510

Leu Ala Met Arg Ile Arg Ala Cys Ala Leu Cys Gly Leu Ala Gly Glu
                515                 520                 525

Gly Leu Thr Lys Ala Ala Glu Gln Glu Leu Leu Arg Leu Gln Cys Lys
                530                 535                 540

Ser Lys Gly Cys Trp Gly Cys His Pro Phe Tyr Arg Asn Gly Ser Asn
545                 550                 555                 560

Val Leu Ser Trp Ile Gly Ser Glu Ala Leu Thr Thr Ala Tyr Ala Ile
                565                 570                 575

Ala Ala Leu Gln Pro Ile Asp Ile
                580

<210> SEQ ID NO 23
<211> LENGTH: 6
<212> TYPE: PRT
<213> ORGANISM: Artificial Sequence
```

```
<220> FEATURE:
<223> OTHER INFORMATION: Synthesized, Alternative class II motif: DLDTTS

<400> SEQUENCE: 23

Asp Leu Asp Thr Thr Ser
1               5

<210> SEQ ID NO 24
<211> LENGTH: 8
<212> TYPE: PRT
<213> ORGANISM: Artificial Sequence
<220> FEATURE:
<223> OTHER INFORMATION: Synthesized, Motif III: QCKSKGCW

<400> SEQUENCE: 24

Gln Cys Lys Ser Lys Gly Cys Trp
1               5

<210> SEQ ID NO 25
<211> LENGTH: 22
<212> TYPE: PRT
<213> ORGANISM: Artificial Sequence
<220> FEATURE:
<223> OTHER INFORMATION: Synthesized, Motif IV: DGILQVYFDVERPRIDPVVVAN

<400> SEQUENCE: 25

Asp Gly Ile Leu Gln Val Tyr Phe Asp Val Glu Arg Pro Arg Ile Asp
1               5                   10                  15

Pro Val Val Val Ala Asn
            20

<210> SEQ ID NO 26
<211> LENGTH: 8
<212> TYPE: PRT
<213> ORGANISM: Artificial Sequence
<220> FEATURE:
<223> OTHER INFORMATION: Synthesized, Modified motif III

<400> SEQUENCE: 26

Gln Cys Ala Ala Ala Gly Cys Trp
1               5

<210> SEQ ID NO 27
<211> LENGTH: 7
<212> TYPE: PRT
<213> ORGANISM: Artificial Sequence
<220> FEATURE:
<223> OTHER INFORMATION: Synthesized, Modified motif III

<400> SEQUENCE: 27

Gln Cys Glu Asp Gly Gly Trp
1               5

<210> SEQ ID NO 28
<211> LENGTH: 22
<212> TYPE: PRT
<213> ORGANISM: Artificial Sequence
<220> FEATURE:
<223> OTHER INFORMATION: Synthesized, Modified motif IV

<400> SEQUENCE: 28

Asp Gly Ile Leu Gln Val Ala Ala Ala Val Glu Arg Pro Arg Ile Asp
1               5                   10                  15

Pro Val Val Val Ala Asn
            20
```

```
<210> SEQ ID NO 29
<211> LENGTH: 7
<212> TYPE: PRT
<213> ORGANISM: Artificial Sequence
<220> FEATURE:
<223> OTHER INFORMATION: Synthesized, Modified class I motif - mutated

<400> SEQUENCE: 29

Asp Ser Phe Asp Pro Leu Glu
1               5
```

METHOD FOR PRODUCING ALBICANOL COMPOUNDS

CROSS-REFERENCE TO RELATED APPLICATIONS

This application is a U.S. National Phase Application of International Patent Application No. PCT/EP2019/063824, filed May 28, 2019, which claims the benefit of priority to International Patent Application No. PCT/CN2018/088902 filed May 29, 2018, and which claims the benefit of priority to European Patent Application No. 18188427.1, filed Aug. 10, 2018, the entire contents of which are hereby incorporated by reference herein.

REFERENCE TO AN ELECTRONIC SEQUENCE LISTING

The contents of the electronic sequence listing (2021-05-03_RevisedSequenceListing_36803-265.txt; Size: 94,387 bytes; and Date of Creation: May 3, 2021) is herein incorporated by reference in its entirety.

TECHNICAL FIELD

Provided herein are biochemical methods of producing albicanol and related compounds, like phosphorylated albicanol compounds and derivatives, which method comprises the use of novel polypeptides with albicanyl diphosphate synthase activity.

BACKGROUND

Terpenes are found in most organisms (microorganisms, animals and plants). These compounds are made up of five carbon units called isoprene units and are classified by the number of these units present in their structure, which may comprise cyclic structural elements. Thus monoterpenes, sesquiterpenes and diterpenes are terpenes containing 10, 15 and 20 carbon atoms, respectively. Sesquiterpenes, for example, are widely found in the plant kingdom. Many sesquiterpene molecules are known for their flavor and fragrance properties and their cosmetic, medicinal and antimicrobial effects. Numerous sesquiterpene hydrocarbons and sesquiterpenoids have been identified. Chemical synthesis approaches have been developed but are still complex and not always cost-effective.

Biosynthetic production of terpenes involves enzymes called terpene synthases. There are numerous sesquiterpene synthases present in the plant kingdom, all using the same substrate (farnesyl diphosphate, FPP), but having different product profiles. Genes and cDNAs encoding sesquiterpene synthases have been cloned and the corresponding recombinant enzymes characterized.

Many of the main sources for sesquiterpenes, for example compounds with a drimane structure, like albicanol compounds or drimenol compounds, are plants naturally containing the sesquiterpene; however, the content of sesquiterpenes in these natural sources can be low. There still remains a need for the discovery of new terpene synthases and more cost-effective methods of producing sesquiterpenes such as albicanol compounds, a potential building block for the preparation of highly valuable perfumery ingredients, such as Ambrox.

SUMMARY

The above-mentioned problem could be solved by providing a new class of enzymes which show albicanyl diphosphate synthase activity and produce albicanyl diphosphate with surprisingly high selectivity from FPP. In particular a novel albicanyl diphosphate synthase gene and two natural variants thereof were identified from the fern *Dryopteris fragrans*.

Said novel synthase (DfHAD) and its variants have only ≤23% homology with the fungal synthases CvTPS1 and LoTPS1 or other bifunctional terpene synthases as identified previously by the present applicant and described in EP application No. 17174399.0. (see also alignment of FIGS. 9A-9L). But, more importantly, the synthases of the present invention also contain a class I motif and a class II motif. Said motifs are characteristics of terpene synthases, and one of the essential features of the albicanol synthases described in EP application No. 17174399.0. Class I is mainly found in mono- or sesquiterpene synthases, while class II is mainly found in diterpene synthases.

As the fern DfHAD of the present invention contain a slightly modified class I motif and a slightly modified class II motif, they can be further distinguished form the earlier described fungal albicanol synthases.

The albicanyl diphosphate synthase of the present invention and its variants may also be considered as "haloacid-dehalogenase-like hydrolase" ("HAD-like hydrolase") for the following reason:

In Pfam search, a haloacid dehalogenase-like hydrolase domain (HAD_2, PF13419.5) in position 86 to 195 (of SEQ ID NO:2) ("Domain 1") and a haloacid dehalogenase-like hydrolase domain (PF00702.25) in position 40 to 187 (of SEQ ID NO:2) ("Domain 3"), with domain E-values less than 0.005 could be identified. These HAD-like hydrolase domains are found in a superfamily of enzyme comprising enzymes with phosphatase activities. These domains could be found in the N-terminal half of DfHAD.

The highest identity found in NCBI by using blastp is 29% (99% coverage) with proteins belonging to fungi containing a putative HAD-like domain, as analysed by Pfam search.

DESCRIPTION OF THE DRAWINGS

FIG. 1: Structure of drimane, (+)-albicanol and (−)-drimenol.

Figure 9D:
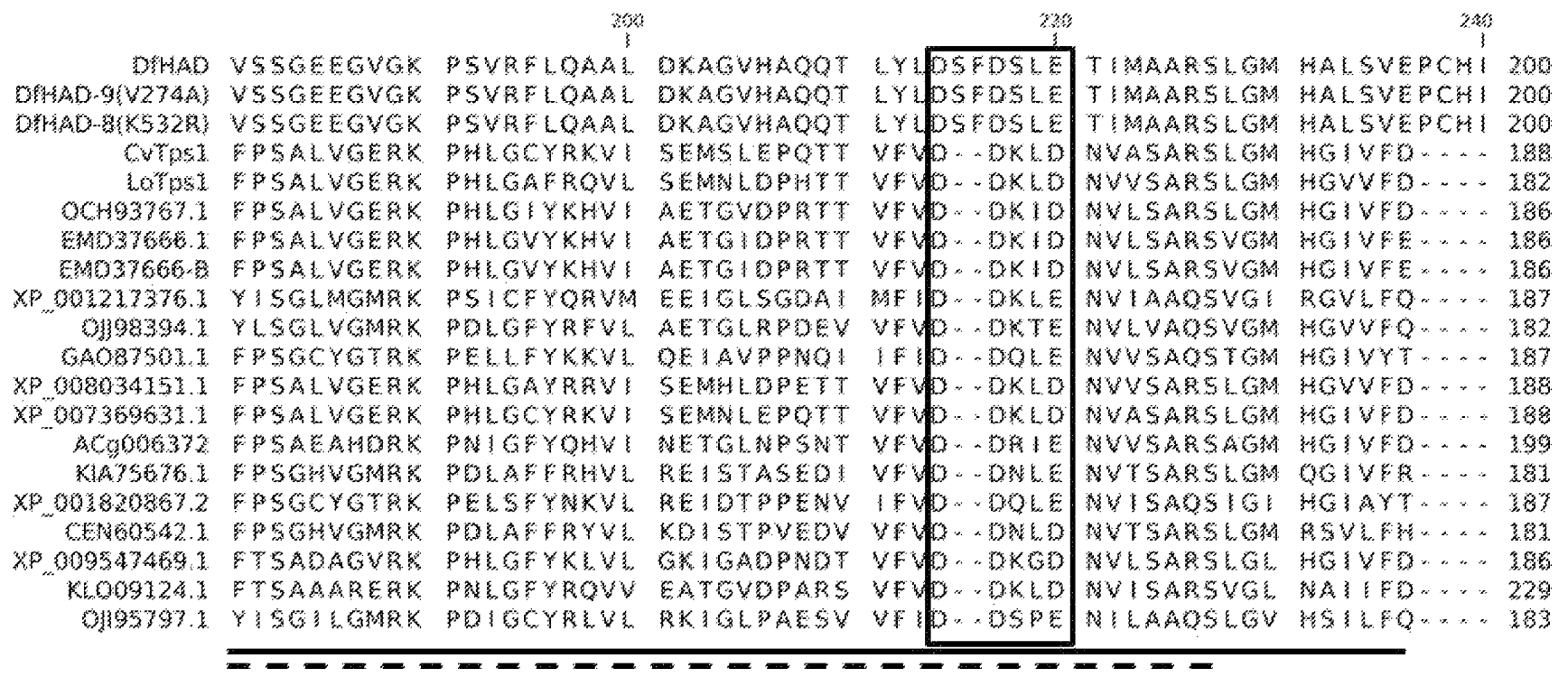
Figure 9G:
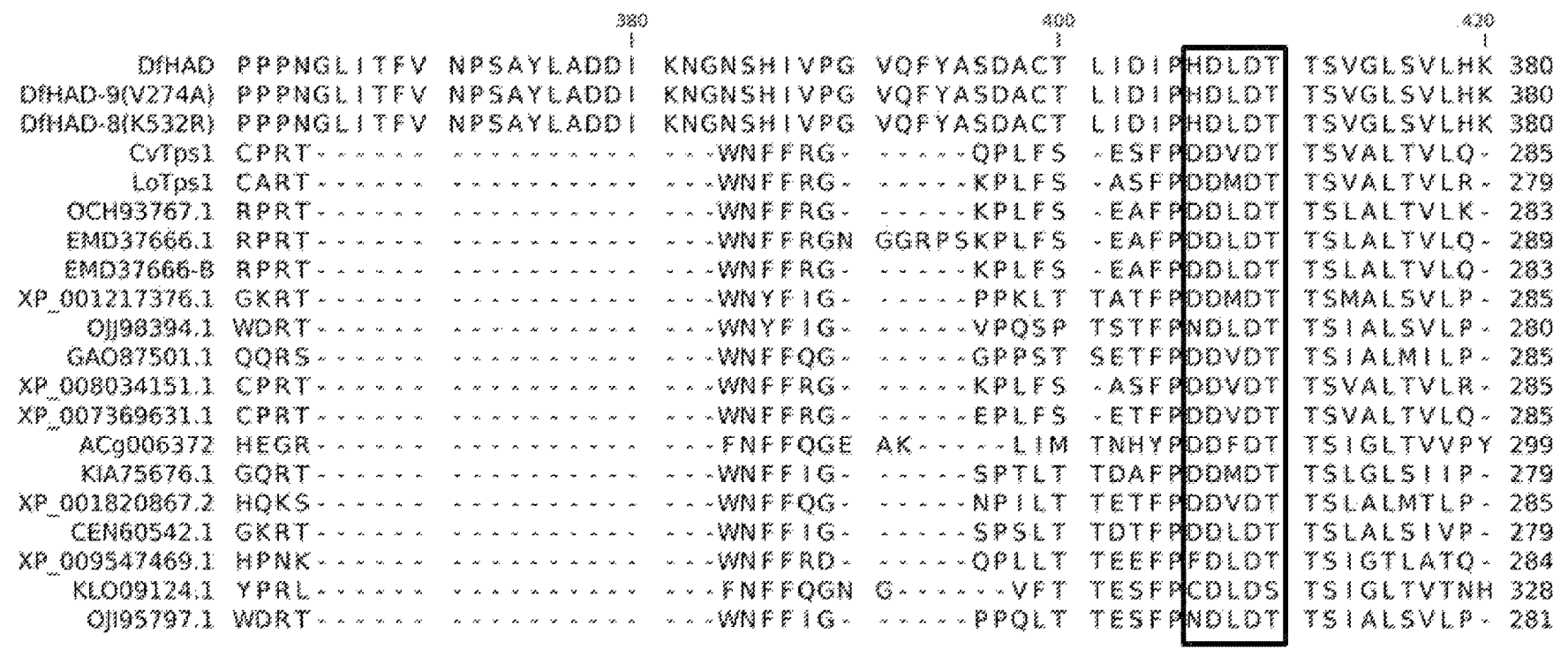

FIGS. 9A-9L: Amino acid sequences alignment of putative terpene synthases containing class I and class II motifs: DfHAD (SEQ ID NO:2) DfHAD-9 (V274A) (SEQ ID NO:6) DfHAD-8 (K532R) (SEQ ID NO:4) of the present invention; CvTps1, LoTps1, OCH93767.1, EMD37666.1, EMD37666-B, XP_001217376.1, OJJ98394.1, GAO87501.1, XP_008034151.1, XP_007369631.1, ACg006372, KIA75676.1, XP_001820867.2, CEN60542.1, XP_009547469.1, KLO09124.1 and OJI95797.1 as previously described. Continuous line is Pfam domain 1 and discontinuous line is Pfam domain 3. The modified Class I and II motifs as well as additional motifs III and IV are boxed.

FIG. 10: List of engineered mutations in class I and class II motifs of DfHAD.

Figure 2:
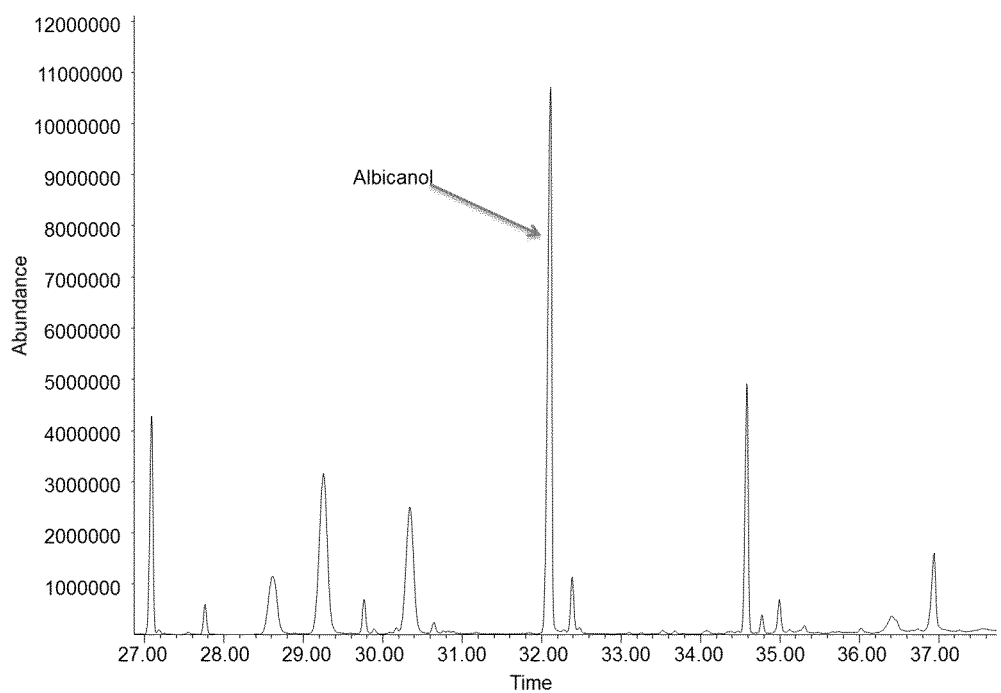
FIG. 2: GC/MS chromatogram of a dichloromethane extract obtained from *Dryopteris fragrans* leaves (only the zone for sesquiterpenes is displayed). The arrow denotes the albicanol peak.

ABBREVIATIONS USED bp base pair
BAP bacterial alkaline phosphatase
kb kilo base
DNA deoxyribonucleic acid
cDNA complementary DNA
DTT dithiothreitol
FPP farnesyl diphosphate
GC gas chromatograph
HAD Haloacid dehalogenase
MS mass spectrometer/mass spectrometry
MVA mevalonic acid
PCR polymerase chain reaction
RNA ribonucleic acid
mRNA messenger ribonucleic acid
miRNA micro RNA
siRNA small interfering RNA
rRNA ribosomal RNA
tRNA transfer RNA

Definitions

"Albicanol" for the purpose of this application relates to (+)-albicanol (CAS: 54632-04-1).

"Drimenol" for purposes of this application relates to (−)-drimenol (CAS: 468-68-8).

"Ambrox" for purposes of this application relates to IUPAC Name: (−)-(3aR,5aS,9aS,9bR)-3a,6,6,9a-tetramethyldodecahydronaphto[2,1-b]furan (CAS: 6790-58-5).

The terms "bifunctional terpene synthase" or "polypeptide having bifunctional terpene synthase activity" relate to a polypeptide that comprises class I and class II synthase motifs and has bifunctional terpene activity of protonation-initiated cyclization and ionization-initiated cyclization catalytic activities. (J. Schrader & J. Bohlman. Biotechnology of isoprenoids. *Adv. Biochem. Eng. Biot.*, 148, 1-475. (DOI: 10.1007/978-3-319-20107-8)) A bifunctional terpene synthase belongs to the Haloacid dehalogenase-like (HAD-like) hydrolase superfamily which comprises domains corresponding to Pfam domains PF13419.5 (Domain 1) and PF00702.25 (Domain 3).

The term "drimane sesquiterpene" relates to a terpene having a drimane-like carbon skeleton structure as depicted in FIG. 1.

The term "class I synthase" relates to a terpene synthase that catalyses ionization-initiated reactions, for example, monoterpene and sesquiterpene synthases.

The term "class I synthase motif" relates to an active site of a terpene synthase that comprises the conserved DDxx(D/E) motif. The aspartic acid residues of this class I motif bind, for example, a divalent metal ion (most often $Mg^{2+}$) involved in the binding of the diphosphate group and catalyze the ionization and cleavage of the allylic diphosphate bond of the substrate.

The term "modified class I synthase motif" relates to an active site of a terpene synthase that comprises the conserved DSFDxx(D/E) (SEQ ID NO:11), in particular DSFDSLE (SEQ ID NO:13), motif.

The term "class II synthase" relates to a terpene synthase that catalyses protonation-initiated cyclization reactions, for example, typically involved in the biosynthesis of triterpenes and labdane diterpenes. In class II terpene synthases, the protonation-initiated reaction may involve, for example, acidic amino acids donating a proton to the terminal double-bond.

The term "class II synthase motif" relates to an active site of a terpene synthase that comprises the conserved DxDD or DxD(T/S)T motif.

The term "modified class II synthase motif" relates to an active site of a terpene synthase that comprises the conserved HDxD(T/S) (SEQ ID NO:12), in particular HDLDT (SEQ ID NO:14), motif, or alternatively the motif DLDTTS (SEQ ID NO:23)

The terms "albicanyl diphosphate synthase" or "polypeptide having albicanyl diphosphate synthase activity" or "albicanyl diphosphate synthase protein" or "having the ability to produce albicanyl diphosphate" relate to a polypeptide capable of catalyzing the synthesis of albicanyl diphosphate, in the form of any of its stereoisomers or a mixture thereof, starting from an acyclic terpene pyrophosphate, particularly farnesyl diphosphate (FPP). Albicanyl diphosphate may be the only product or may be part of a mixture of sesquiterpenes. Said mixture may comprise albicanyl monophosphate and/or albicanol in any proportion, particularly in a predominant proportion and more particularly in a substantial proportion as defined below.

"Albicanyl diphosphate synthase activity" is determined under "standard conditions" as described herein below: They can be determined using recombinant albicanyl diphosphate synthase expressing host cells, disrupted albicanyl diphosphate synthase expressing cells, fractions of these or enriched or purified albicanyl diphosphate synthase enzyme, in a culture medium or reaction medium, preferably buffered, having a pH in the range of 6 to 11, preferably 7 to 9, at a temperature in the range of about 20 to 45° C., like about 25 to 40° C., preferably 25 to 32° C. and in the presence of a reference substrate, here in particular FPP, either added at an initial concentration in the range of 1 to 100 µM, preferably 5 to 50 µM, in particular 30 to 40 µM, or endogenously produced by the host cell. The conversion reaction to form of albicanyl diphosphate is conducted form 10 min to 5 h, preferably about 1 to 2 h. If no endogenous alkaline phosphatase is present, one or more exogenous phosphatase is added to the reaction mixture to convert albicanyl diphosphate as formed by the synthase. Albicanol may then be determined in conventional matter, for example after extraction with an organic solvent, like ethyl acetate. Particular examples of suitable standard conditions are applied in the Experimental Part below, like in Example 5, which conditions also shall form part of the general disclosure of the invention.

The terms "biological function," "function," "biological activity" or "activity" refer to the ability of the terpene synthase as described herein to catalyze the formation of albicanyl diphosphate and/or albicanol or a mixture of compounds comprising albicanyl diphosphate, and/or albicanyl monophosphate and/or albicanol and/or and one or more other terpenes, in particular albicanyl diphosphate.

The term "phosphatase" or polypeptide "having phosphatase activity" relates to a polypeptide capable of catalyzing the cleavage of a phosphoric ester into phosphate and the corresponding alcohol. Depending on the respective pH optimum the enzyme may either be an alkaline phosphatase (E.C.3.1.3.1) or an acid phosphatase (E.C. 3.1.3.2). In particular, according to the present invention alkaline phosphatases of different origin, more particularly of bacterial origin may be applied. The applied phosphatase should be able to produce a drimane alcohol, like an albicanol and/or a drimenol from the respective mono- or diphosphate ester.

The terms "mixture of terpenes" or "mixture of sesquiterpenes" refer to a mixture of terpenes or of sesquiterpenes that comprises albicanyl diphosphate and/or albicanyl monophosphate and/or albicanol and may also comprise one or more additional terpenes or one or more additional sesquiterpenes.

The "mevalonate pathway" also known as the "isoprenoid pathway" or "HMG-CoA reductase pathway" is an essential metabolic pathway present in eukaryotes, archaea, and some bacteria. The mevalonate pathway begins with acetyl-CoA and produces two five-carbon building blocks called isopentenyl pyrophosphate (IPP) and dimethylallyl pyrophosphate (DMAPP). Key enzymes are acetoacetyl-CoA thiolase (atoB), HMG-CoA synthase (mvaS), HMG-CoA reductase (mvaA), mevalonate kinase (MvaK1), phosphomevalonate kinase (MvaK2), a mevalonate diphosphate decarboxylase (MvaD), and an isopentenyl diphosphate isomerase (idi). Combining the mevalonate pathway with enzyme activity to generate the terpene precursors GPP, FPP or GGPP, like in particular FPP synthase (ERG20), allows the recombinant cellular production of terpenes.

As used herein, the term "host cell" or "transformed cell" refers to a cell (or organism) altered to harbor at least one nucleic acid molecule, for instance, a recombinant gene encoding a desired protein or nucleic acid sequence which upon transcription yields a functional polypeptide of the present invention, i.p. an albicanyl diphosphate synthase protein useful to produce albicanyl diphosphate and/or albicanyl monophosphate and/or albicanol or corresponding mixtures of terpenes containing albicanyl diphosphate and/or albicanyl monophosphate and/or albicanol. The host cell is particularly a bacterial cell, a fungal cell or a plant cell or plants. The host cell may contain a recombinant gene which has been integrated into the nuclear or organelle genomes of the host cell. Alternatively, the host may contain the recombinant gene extra-chromosomally.

The term "organism" refers to any non-human multicellular or unicellular organisms such as a plant, or a microorganism. Particularly, a micro-organism is a bacterium, a yeast, an algae or a fungus.

The term "plant" is used interchangeably to include plant cells including plant protoplasts, plant tissues, plant cell tissue cultures giving rise to regenerated plants, or parts of plants, or plant organs such as roots, stems, leaves, flowers, pollen, ovules, embryos, fruits and the like. Any plant can be used to carry out the methods of an embodiment herein.

A particular organism or cell is meant to be "capable of producing FPP" when it produces FPP naturally or when it does not produce FPP naturally but is transformed to produce FPP with a nucleic acid as described herein. Organisms or cells transformed to produce a higher amount of FPP than the naturally occurring organism or cell are also encompassed by the "organisms or cells capable of producing FPP".

A particular organism or cell is meant to be "capable of producing albicanyl diphosphate" when it produces albicanyl diphosphate naturally or when it does not produce albicanyl diphosphate naturally but is transformed to produce albicanyl diphosphate with a nucleic acid as described herein. Organisms or cells transformed to produce a higher amount of albicanyl diphosphate than the naturally occurring organism or cell are also encompassed by the "organisms or cells capable of producing albicanyl diphosphate".

A particular organism or cell is meant to be "capable of producing albicanol" when it produces albicanol naturally or when it does not produce albicanol naturally but is transformed to produce albicanyl diphosphate with a nucleic acid as described herein, and optionally further transformed with a nucleic acid to produce enzyme activity converting albicanyl diphosphate to albicanol. Organisms or cells transformed to produce a higher amount of albicanol than the naturally occurring organism or cell are also encompassed by the "organisms or cells capable of producing albicanol".

For the descriptions herein and the appended claims, the use of "or" means "and/or" unless stated otherwise. Similarly, "comprise," "comprises," "comprising", "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of"

The terms "purified," "substantially purified," and "isolated" as used herein refer to the state of being free of other, dissimilar compounds with which a compound of the invention is normally associated in its natural state, so that the "purified," "substantially purified," and "isolated" subject comprises at least 0.5%, 1%, 5%, 10%, or 20%, or at least 50% or 75% of the mass, by weight, of a given sample. In one embodiment, these terms refer to the compound of the invention comprising at least 95, 96, 97, 98, 99 or 100%, of the mass, by weight, of a given sample. As used herein, the terms "purified," "substantially purified," and "isolated" when referring to a nucleic acid or protein, of nucleic acids or proteins, also refers to a state of purification or concentration different than that which occurs naturally, for example in an prokaryotic or eukaryotic environment, like, for example in a bacterial or fungal cell, or in the mammalian organism, especially human body. Any degree of purification or concentration greater than that which occurs naturally, including (1) the purification from other associated structures or compounds or (2) the association with structures or compounds to which it is not normally assoociated in said prokaryotic or eukaryotic environment, are within the meaning of "isolated". The nucleic acid or protein or classes of nucleic acids or proteins, described herein, may be isolated, or otherwise associated with structures or compounds to which they are not normally associated in nature, according to a variety of methods and processes known to those of skill in the art.

In the context of the descriptions provided herein and of the appended claims, the use of "or" means "and/or" unless stated otherwise.

Similarly, "comprise," "comprises," "comprising", "include," "includes," and "including" are interchangeable and not intended to be limiting.

The term "about" indicates a potential variation of ±25% of the stated value, in particular ±15%, ±10%, more particularly ±5%, ±2% or ±1%.

The term "substantially" describes a range of values of from about 80 to 100%, such as, for example, 85-99.9%, in particular 90 to 99.9%, more particularly 95 to 99.9%, or 98 to 99.9% and especially 99 to 99.9%.

"Predominantly" refers to a proportion in the range of above 50%, as for example in the range of 51 to 100%, particularly in the range of 75 to 99.9%; more particularly 85 to 98.5%, like 95 to 99%.

A "main product" in the context of the present invention designates a single compound or a group of at least 2 compounds, like 2, 3, 4, 5 or more, particularly 2 or 3 compounds, which single compound or group of compounds is "predominantly" prepared by a reaction as described herein, and is contained in said reaction in a predominant proportion based on the total amount of the constituents of the product formed by said reaction. Said proportion may be a molar proportion, a weight proportion or, preferably based on chromatographic analytics, an area proportion calculated from the corresponding chromatogram of the reaction products.

A "side product" in the context of the present invention designates a single compound or a group of at least 2 compounds, like 2, 3, 4, 5 or more, particularly 2 or 3 compounds, which single compound or group of compounds is not "predominantly" prepared by a reaction as described herein.

Because of the reversibility of enzymatic reactions, the present invention relates, unless otherwise stated, to the enzymatic or biocatalytic reactions described herein in both directions of reaction.

"Functional mutants" of herein described polypeptides include the "functional equivalents" of such polypeptides as defined below.

The term "stereoisomers" includes in particular conformational isomers.

Included in general are, according to the invention, all "stereoisomeric forms" of the compounds described herein, such as constitutional isomers and, in particular, stereoisomers and mixtures thereof, e.g. optical isomers, or geometric isomers, such as E- and Z-isomers, and combinations thereof. If several asymmetric centers are present in one molecule, the invention encompasses all combinations of different conformations of these asymmetry centers, e.g. enantiomeric pairs "Stereoselectivity" describes the ability to produce a particular stereoisomer of a compound in a stereoisomerically pure form or to specifically convert a particular stereoisomer in an enzyme catalyzed method as described herein out of a plurality of stereoisomers. More specifically, this means that a product of the invention is enriched with respect to a specific stereoisomer, or an educt may be depleted with respect to a particular stereoisomer. This may be quantified via the purity % ee-parameter calculated according to the formula:

% ee=[$X_A$-$X_B$]/[$X_A$+$X_B$]*100, wherein $X_A$ and $X_B$ represent the molar ratio (Molenbruch) of the stereoisomers A and B.

The terms "selectively converting" or "increasing the selectivity" in general means that a particular stereoisomeric form, as for example the E-form, of an unsaturated hydrocarbon, is converted in a higher proportion or amount (compared on a molar basis) than the corresponding other stereoisomeric form, as for example Z-form, either during the entire course of said reaction (i.e. between initiation and termination of the reaction), or during an "interval" of said reaction, at a certain point of time of said reaction, or during an "interval" of said reaction. In particular, said selectivity may be observed during an "interval" corresponding 1 to 99%, 2 to 95%, 3 to 90%, 5 to 85%, 10 to 80%, 15 to 75%, 20 to 70%, 25 to 65%, 30 to 60, or 40 to 50% conversion of the initial amount of the substrate. Said higher proportion or amount may, for example, be expressed in terms of:

a higher maximum yield of an isomer observed during the entire course of the reaction or said interval thereof;

a higher relative amount of an isomer at a defined % degree of conversion value of the substrate; and/or an identical relative amount of an isomer at a higher % degree of conversion value;

each of which preferably being observed relative to a reference method, said reference method being performed under otherwise identical condition with known chemical or biochemical means.

Generally also comprised in accordance with the invention are all "isomeric forms" of the compounds described herein, such as constitutional isomers and in particular stereoisomers and mixtures of these, such as, for example, optical isomers or geometric isomers, such as E- and Z-isomers, and combinations of these. If several centers of asymmetry are present in a molecule, then the invention comprises all combinations of different conformations of these centers of asymmetry, such as, for example, pairs of enantiomers, or any mixtures of stereoisomeric forms.

"Yield" and/or the "conversion rate" of a reaction according to the invention is determined over a defined period of, for example, 4, 6, 8, 10, 12, 16, 20, 24, 36 or 48 hours, in which the reaction takes place. In particular, the reaction is carried out under precisely defined conditions, for example at "standard conditions" as herein defined.

The different yield parameters ("Yield" or $Y_{P/S}$; "Specific Productivity Yield"; or Space-Time-Yield (STY)) are well known in the art and are determined as described in the literature.

"Yield" and "$Y_{P/S}$" (each expressed in mass of product produced/mass of material consumed) are herein used as synonyms.

The specific productivity-yield describes the amount of a product, that is produced per h and L fermentation broth per g of biomass. The amount of wet cell weight stated as WCW describes the quantity of biologically active microorganism in a biochemical reaction. The value is given as g product per g WCW per h (i.e. g/gWCW$^{-1}$ h$^{-1}$). Alternatively, the quantity of biomass can also be expressed as the amount of dry cell weight stated as DCW. Furthermore, the biomass concentration can be more easily determined by measuring the optical density at 600 nm ($OD_{600}$) and by using an experimentally determined correlation factor for estimating the corresponding wet cell or dry cell weight, respectively.

The term "fermentative production" or "fermentation" refers to the ability of a microorganism (assisted by enzyme activity contained in or generated by said microorganism) to produce a chemical compound in cell culture utilizing at least one carbon source added to the incubation.

The term "fermentation broth" is understood to mean a liquid, particularly aqueous or aqueous/organic solution which is based on a fermentative process and has not been worked up or has been worked up, for example, as described herein.

An "enzymatically catalyzed" or "biocatalytic" method means that said method is performed under the catalytic action of an enzyme, including enzyme mutants, as herein defined. Thus the method can either be performed in the presence of said enzyme in isolated (purified, enriched) or crude form or in the presence of a cellular system, in particular, natural or recombinant microbial cells containing said enzyme in active form, and having the ability to catalyze the conversion reaction as disclosed herein.

If the present disclosure refers to features, parameters and ranges thereof of different degree of preference (including general, not explicitly preferred features, parameters and ranges thereof) then, unless otherwise stated, any combination of two or more of such features, parameters and ranges thereof, irrespective of their respective degree of preference, is encompassed by the disclosure of the present description.

DETAILED DESCRIPTION a. Particular Embodiments of the Invention

The present invention particularly refers to the following embodiments:
1. An isolated polypeptide of the Haloacid dehalogenase-like (HAD-like) hydrolase superfamily or a variant or mutant thereof, comprising cyclic terpene synthase activity, wherein said polypeptide comprises
   a. a modified class I synthase motif as set forth in SEQ ID NO: 11 (DSFDxx(D/E)) corresponding to sequence positions 174 to 180 of SEQ ID NO: 2, wherein x may be any naturally occurring amino acid residue, and preferably is selected from S and L, in particular the motif of SEQ ID NO:13; and
   b. C-terminal to modified class I motif, a modified class II synthase motif as set forth in SEQ ID NO: 12 (HDxD(T/S) corresponding to sequence positions 366 to 370 of SEQ ID NO: 2, wherein x may be any naturally occurring amino acid residue, and preferably represents L, in particular the motif of SEQ ID NO:14; and
   c. optionally at least one further sequence motif selected from
      i. a partial sequence form position 86 to 195 of SEQ ID NO: 2; and
      ii. a partial sequence form position 40 to 187 of SEQ ID NO: 2.

In a particular embodiment there is provided an isolated polypeptide of the Haloacid dehalogenase-like (HAD-like) hydrolase superfamily or a variant or mutant thereof, comprising cyclic terpene synthase activity, wherein said polypeptide comprises
   a. a modified class I synthase motif as set forth in SEQ ID NO: 13 corresponding to sequence positions 174 to 180 of SEQ ID NO: 2, and
   b. C-terminal to modified class I motif, a modified class II synthase motif as set forth in SEQ ID NO: 14, corresponding to sequence positions 366 to 370 of SEQ ID NO: 2, and
   c. at least one further sequence motif selected from
      i. a partial sequence form position 86 to 195 of SEQ ID NO: 2; and
      ii. a partial sequence form position 40 to 187 of SEQ ID NO: 2.

In an alternative to the above embodiments said modified class II synthase motif may also be a motif of SEQ ID NO:23 (i.e. DLDTTS) corresponding to sequence positions 367 to 372 of SEQ ID NO: 2.

Alternatively or in addition to the above sequence motif or motifs the isolated polypeptide of the Haloacid dehalogenase-like (HAD-like) hydrolase superfamily or a variant or mutant thereof, comprising cyclic terpene synthase activity, may also comprise the sequence motif III: QCKSKGCW (SEQ ID NO: 24) corresponding to sequence positions 542 to 549 of SEQ ID NO: 2 and/or the sequence motif IV: DGILQVYFDVERPRIDPVV-VAN (SEQ ID NO: 25) corresponding to sequence positions 404 to 424 of SEQ ID NO: 2

The sequence motif III may be further modified to motif: QCEDGGW (SEQ ID NO: 27), Therein the N-terminal partial sequence motif QCE may be modified to: QCQ, QCK, QCA QCD, QCG, QQN, QDE, QED or QET, and independently thereof, the C-Terminal partial sequence motif "GGW" may be changed to GGF or GSW.

2. The polypeptide of embodiment 1, comprising the ability to produce a drimane sesquiterpene, and/or a phosphate derivative thereof, like a monophosphate and more particularly a diphosphate derivative thereof, in particular from farnesyl diphosphate (FPP) as substrate.

3. The polypeptide of embodiment 2, comprising the ability to produce an albicanyl phosphate derivative like a monophosphate and more particularly an albicanyl diphosphate from farnesyl diphosphate (FPP) as substrate.

4. An isolated polypeptide of the Haloacid dehalogenase-like (HAD-like) hydrolase superfamily, comprising cyclic terpene synthase activity, wherein said polypeptide is DfHAD comprising an amino acid sequence of SEQ ID NO: 2, or a mutant or a natural variant thereof, comprising an amino acid sequence having at least 40%, 45%, 50%, 55%, 60%, 65%, 70%, 75%, 80%, 85%, 90%, 95%, 96%, 97%, 98%, or 99% sequence identity to SEQ ID NO: 2, and retaining said terpene synthase activity.

5. The polypeptide of embodiment 4, comprising the ability to produce a drimane sesquiterpene, and/or a phosphate derivative thereof, like a monophosphate and more particularly a diphosphate derivative thereof, in particular from farnesyl diphosphate (FPP) as substrate.

6. The polypeptide of embodiment 5, comprising the ability to produce an albicanyl phosphate derivative like a monophosphate and more particularly an albicanyl diphosphate from farnesyl diphosphate (FPP) as substrate.

7. The polypeptide of one of the preceding embodiments, which is isolated from plants of the genus *Dryopteris*, in particular of the species *Dryopteris fragrans* or in other plant or fern species.

8. An isolated polypeptide which is a in particular natural variant of DfHAD of anyone of embodiments 1 to 4, selected from
   a. DfHAD-9 (V274A) comprising the amino acid substitution (V274A) in position 274 of SEQ ID NO:2 or in an amino acid sequence having at least 40%, 45%, 50%, 55%, 60%, 65%, 70%, 75%, 80%, 85%, 90%, 95%, 96%, 97%, 98%, or 99% sequence identity to SEQ ID NO: 2; and
   b. DfHAD-8 (K532R) comprising the amino acid substitution (K532R) in position 532 of SEQ ID NO:2 or in an amino acid sequence having at least 40%, 45%, 50%, 55%, 60%, 65%, 70%, 75%, 80%, 85%, 90%, 95%, 96%, 97%, 98%, or 99% sequence identity to SEQ ID NO: 2.

9. The polypeptides of anyone of the embodiments 4 to 8 further comprising
   a. a modified class I synthase motif as set forth in SEQ ID NO: 11 (DSFDxx(D/E)) corresponding to sequence positions 174 to 180 of SEQ ID NO: 2, wherein x may be any naturally occurring amino acid residue, and preferably is selected from S and L, in particular the motif of SEQ ID NO:13; and b. C-terminal to modified class I synthase motif I, a modified class II synthase motif as set forth in SEQ ID NO: 12 (HDxD(T/S)) corresponding to sequence positions 366 to 370 of SEQ ID NO: 2, wherein x may be any naturally occurring amino acid residue, and preferably represents L, in particular the motif of SEQ ID NO:14; and c. and optionally at least one further sequence motif selected from
   i. a partial sequence form position 86 to 195 of SEQ ID NO: 2; and
   ii. a partial sequence form position 40 to 187 of SEQ ID NO: 2.

In a particular embodiment there is provided an isolated polypeptide of the Haloacid dehalogenase-like (HAD-like) hydrolase superfamily or a variant or mutant thereof, comprising cyclic terpene synthase activity, wherein said polypeptide further comprises a. a modified class I synthase motif as set forth in SEQ ID NO: 13 corresponding to sequence positions 174 to 180 of SEQ ID NO: 2, and b. C-terminal to modified class I motif, a modified class II synthase motif as set forth in SEQ ID NO: 14, corresponding to sequence positions 366 to 370 of SEQ ID NO: 2, and c. at least one further sequence motif selected from
   i. a partial sequence form position 86 to 195 of SEQ ID NO: 2; and
   ii. a partial sequence form position 40 to 187 of SEQ ID NO: 2.

In an alternative to the above embodiments said modified class II synthase motif may also be a motif of SEQ ID NO:23 (i.e. DLDTTS) corresponding to sequence positions 367 to 372 of SEQ ID NO: 2.

Alternatively or in addition to the above sequence motif or motifs the isolated polypeptide of the Haloacid dehalogenase-like (HAD-like) hydrolase superfamily or a variant or mutant thereof, comprising cyclic terpene synthase activity, may also comprise the sequence motif III: QCKSKGCW (SEQ ID NO: 24) corresponding to sequence positions 542 to 549 of SEQ ID NO: 2 and/or the sequence motif IV: DGILQVYFDVERPRIDPVV-VAN (SEQ ID NO: 25) corresponding to sequence positions 404 to 424 of SEQ ID NO: 2

The sequence motif III may be further modified to motif: QCEDGGW (SEQ ID NO: 27), Therein the N-terminal partial sequence motif QCE may be modified to: QCQ, QCK, QCA QCD, QCG, QQN, QDE, QED or QET, and independently thereof, the C-Terminal partial sequence motif "GGW" may be changed to GGF or GSW 10. The polypeptide of one of the embodiments 8 and 9, selected from
   a. DfHAD-9 (V274A) comprising the amino acid sequence of SEQ ID NO:6;
   b. DfHAD-8 (K532R) comprising the amino acid sequence of SEQ ID NO:4; and
   c. DfHAD-QW fungal comprising the amino acid sequence of SEQ ID NO:19.

11. The polypeptide of anyone of the preceding embodiments, which catalyses the conversion of an (acyclic) farnesyl diphosphate (in particular of (2E,6E)-3,7,11-trimethyl-dodeca-2,6,10-triene-1-pyrophosphate; FPP) to an albicanyl phosphate derivative like a monophosphate and more particularly an albicanyl diphosphate, preferably with a selectivity of >50%.

12. The polypeptide of anyone of the preceding embodiments, which
   a. comprises an amino acid sequence selected from SEQ ID NO: 2, 4, and 6; or
   b. is encoded by a nucleic acid molecule comprising a coding nucleotide sequence selected from SEQ ID NO:1, 3, 5, 7, 8, 9, and 10.

13. An isolated nucleic acid molecule
   a. comprising a nucleotide sequence encoding the polypeptide of any one of the preceding embodiments; or
   b. comprising a nucleotide sequence selected from SEQ ID NO:1, 3, 5, 7, 8, 9, and 10 or having least 40%, 45%, 50%, 55%, 60%, 65%, 70%, 75%, 80%, 85%, 90%, 95%, 96%, 97%, 98%, or 99% sequence identity to the nucleotide sequence of SEQ ID NO:1, 3, 5, 7, 8, 9, or 10, and encoding a polypeptide of the Haloacid dehalogenase-like (HAD-like) hydrolase superfamily, comprising terpene synthase activity, in particular comprising the ability to produce a drimane sesquiterpene, and/or a phosphate derivative thereof, like a monophosphate and more particularly a diphosphate derivative thereof, and more particularly to produce an albicanyl phosphate derivative like a monophosphate and more particularly an albicanyl diphosphate from farnesyl diphosphate (FPP) as substrate, or
   c. comprising a nucleotide sequence comprising a sequence complementary to one of the sequences of b.; or
   d. comprising a nucleotide sequence hybridizing under stringent conditions to a nucleotide sequence of a, b. or c.

In one particular embodiment, the nucleic acid can be either present naturally in plants of the genus *Dryopteris*, like the species *Dryopteris fragrans* or in other plant or fern species, or be obtained by modifying SEQ ID NO:1, 3, 5, 7, 8, 9 or 10 or the reverse complement thereof.

In another embodiment, the nucleic acid is isolated or is derived from plants of the genus *Dryopteris*, like the species *Dryopteris fragrans*.

14. An expression construct comprising at least one nucleic acid molecule of embodiment 13.

15. A vector comprising at least one nucleic acid molecule of embodiment 13 or at least one expression construct of embodiment 14.

16. The vector of embodiment 15, wherein the vector is a prokaryotic, viral or eukaryotic vector.

17. The vector of embodiment 15 or 16, where the vector is an expression vector.

18. The vector of anyone of the embodiments 15 to 17, which is a plasmid vector.

19. A recombinant host cell or a recombinant non-human host organism comprising
   a. at least one isolated nucleic acid molecule of embodiment 13, optionally stably integrated into the genome; or
   b. at least one expression construct of embodiment 14, optionally stably integrated into the genome; or
   c. at least one vector of any one of embodiments 15 to 18.

20. The host cell or host organism of embodiment 19, selected from a prokaryotic or eukaryotic microorganism, or a cell derived therefrom.

21. The host cell or host organism of embodiment 20, selected from bacterial, fungal and plant cells or plants.

22. The host cell or host organism of embodiment 21, wherein said fungal cells are yeast cells.

23. The host cell or host organism of embodiment 21, wherein said bacterial cells are selected from the genus

*Escherichia*, in particular from the species *E. coli* and said yeast cells are selected from the genus *Saccharomyces* or *Pichia*, in particular from the species *Saccharomyces cerevisiae* or *Pichia pastoris*.

Some of these host cells or organisms do not produce FPP naturally. To be suitable to carry out the method of an embodiment as described herein, organisms or cells that do not produce an acyclic terpene pyrophosphate precursor, e.g. FPP, naturally are genetically modified to produce said precursor. They can be, for example, so transformed either before the modification with the nucleic acid described according to any of the above embodiments or simultaneously. Methods to transform organisms so that they produce an acyclic terpene pyrophosphate precursor, e.g. FPP, are already known in the art. For example, introducing enzyme activities of the mevalonate pathway, is a suitable strategy to make the organism produce FPP.

24. A method for producing at least one catalytically active polypeptide according to any one of embodiments 1 to 12 comprising:
   a. culturing a non-human host organism or host cell of embodiment 19 to express or over-express at least one polypeptide according to anyone of embodiments 1 to 12; and
   b. optionally isolating the polypeptide from the non-human host cell or organism cultured in step a.

25. The method of embodiment 24, further comprising, prior to step a), transforming a non-human host organism or cell with at least one nucleic acid according to embodiment 13, at least one construct of embodiment 14 or at least one vector of anyone of the embodiments 15 to 18 so that it expresses or over-expresses the polypeptide according to any one of embodiments 1 to 12.

26. A method for preparing a mutant polypeptide comprising terpene synthase activity, in particular comprising the ability to produce a drimane sesquiterpene, and/or a phosphate derivative thereof, like a monophosphate and more particularly a diphosphate derivative thereof, and more particularly to produce an albicanyl phosphate derivative like a monophosphate and more particularly an albicanyl diphosphate from farnesyl diphosphate (FPP) as substrate which method comprises the steps of:
   a. selecting a nucleic acid molecule according to embodiment 13;
   b. modifying the selected nucleic acid molecule to obtain at least one mutant nucleic acid molecule;
   c. transforming host cells or unicellular host organisms with the mutant nucleic acid sequence to express a polypeptide encoded by the mutant nucleic acid sequence;
   d. screening the expression product for at least one mutant comprising terpene synthase activity, in particular comprising the ability to produce a drimane sesquiterpene, and/or a phosphate derivative thereof, like a monophosphate and more particularly a diphosphate derivative thereof, and more particularly to produce an albicanyl phosphate derivative like a monophosphate and more particularly an albicanyl diphosphate from farnesyl diphosphate (FPP) as; and,
   e. optionally, if the polypeptide has no desired mutant activity, repeat the process steps a. to d. until a polypeptide with a desired mutant activity is obtained; and
   f. optionally, if a polypeptide having a desired mutant activity was identified in step d., isolating the corresponding mutant nucleic acid obtained in step c.

27. A method for producing a drimane sesquiterpene, in particular albicanol, comprising:
   a. contacting farnesyl diphosphate (FPP) with a polypeptide as defined in anyone of the embodiments 1 to 12, with a polypeptide prepared according to embodiment 24 or 25, or with a mutant polypeptide prepared according to embodiment 26, thereby obtaining at least one phosphate, in particular diphosphate of drimane sesquiterpene, in particular an albicanyl phosphate, more particularly albicanyl diphosphate;
   b. chemically or enzymatically cleaving of the phosphate moiety, in particular diphosphate moiety of said product; and
   c. optionally isolating the drimane sesquiterpene, in particular albicanol.

In a particular embodiment, the phosphate moiety may be cleaved enzymatically, by applying a phosphatase enzyme, more particularly an acid or alkaline phosphatase. Alkaline phosphatases of different origin, like bacterial enzymes, are preferred. Suitable phosphatases are commercially available enzymes.

28. The method of embodiment 27, wherein the drimane sesquiterpene comprises albicanol, preferably as the main product.

29. The method of any one of embodiments 27 and 28, which comprises providing, in particular transforming a non-human host organism or host cell with at least one nucleic acid according to embodiment 13, at least one construct of embodiment 14 or at least one vector of anyone of the embodiments 15 to 16 so that it expresses or over-expresses a polypeptide according to any one of embodiments 1 to 12.

30. The method of any one of embodiments 27 to 29, wherein FPP is contacted with a non-human host organism or host cell, with a cell lysate thereof, or a culture medium containing said non-human host organism host cell and/or with the polypeptide as defined in anyone of the embodiments 1 to 12, isolated from the a non-human host organism or host cell, cell lysate or culture medium.

31. The method of embodiment 30, wherein said drimane sesquiterpene is fermentatively produced by said non-human host organism or host cell.

32. The method of embodiment 30, wherein said drimane sesquiterpene is produced by an enzymatic process, comprising the conversion of FPP with an isolated polypeptide of anyone of the embodiments 1 to 12, optionally in the presence of further adjuvants.

33. The use of a polypeptide as defined in anyone of the embodiments 1 to 12 for preparing odorants, flavours or fragrance ingredients, in particular Ambrox.

34. The use of a drimane sesquiterpene as prepared according to anyone of the embodiments 27 to 32 for preparing odorants, flavours or fragrance ingredients, in particular Ambrox.

35. A method of producing Ambrox, which method comprises
   a. providing albicanol by a method of anyone of the embodiments as recited in any one of embodiments 27 to 32,
   b. optionally isolating albicanol as produced in step a.; and
   c. converting albicanol in a manner know per se to Ambrox, for example as reported in Tetrahedron: Asymmetry 11 (2000) 1375-1388.

36. A composition comprising the substance prepared according to embodiment 34 or 35.

37. The composition according to embodiment 36 selected from the group consisting of
   a. body care compositions
   b. home care compositions
   c. fragrance compositions If not stated otherwise within the above degree ranges of "at least 40%, 45%, 50%, 55%, 60%, 65%, 70%, 75%, 80%, 85%, 90%, 95%, 96%, 97%, 98%, or 99% sequence identity", particular values are those of at least 60%, 65%, 70%, 75%, 80%, 85%, 90%, 95%, 96%, 97%, 98%, or 99% sequence identity and values of at least 80%, 85%, 90%, 95%, 96%, 97%, 98%, or 99% sequence identity are even more particular.

b. Polypeptides Applicable According to the Invention

In this context the following definitions apply:

The generic terms "polypeptide" or "peptide", which may be used interchangeably, refer to a natural or synthetic linear chain or sequence of consecutive, peptidically linked amino acid residues, comprising about 10 up to more than 1.000 residues. Short chain polypeptides with up to 30 residues are also designated as "oligopeptides".

The term "protein" refers to a macromolecular structure consisting of one or more polypeptides. The amino acid sequence of its polypeptide(s) represents the "primary structure" of the protein. The amino acid sequence also predetermines the "secondary structure" of the protein by the formation of special structural elements, such as alpha-helical and beta-sheet structures formed within a polypeptide chain. The arrangement of a plurality of such secondary structural elements defines the "tertiary structure" or spatial arrangement of the protein. If a protein comprises more than one polypeptide chains said chains are spatially arranged forming the "quaternary structure" of the protein. A correct spacial arrangement or "folding" of the protein is prerequisite of protein function. Denaturation or unfolding destroys protein function. If such destruction is reversible, protein function may be restored by refolding.

A typical protein function referred to herein is an "enzyme function", i.e. the protein acts as biocatalyst on a substrate, for example a chemical compound, and catalyzes the conversion of said substrate to a product. An enzyme may show a high or low degree of substrate and/or product specificity.

A "polypeptide" referred to herein as having a particular "activity" thus implicitly refers to a correctly folded protein showing the indicated activity, as for example a specific enzyme activity.

Thus, unless otherwise indicated the term "polypeptide" also encompasses the terms "protein" and "enzyme".

Similarly, the term "polypeptide fragment" encompasses the terms "protein fragment" and "enzyme fragment".

The term "isolated polypeptide" refers to an amino acid sequence that is removed from its natural environment by any method or combination of methods known in the art and includes recombinant, biochemical and synthetic methods.

"Target peptide" refers to an amino acid sequence which targets a protein, or polypeptide to intracellular organelles, i.e., mitochondria, or plastids, or to the extracellular space (secretion signal peptide). A nucleic acid sequence encoding a target peptide may be fused to the nucleic acid sequence encoding the amino terminal end, e.g., N-terminal end, of the protein or polypeptide, or may be used to replace a native targeting polypeptide.

The present invention also relates to "functional equivalents" (also designated as "analogs" or "functional mutations") of the polypeptides specifically described herein.

For example, "functional equivalents" refer to polypeptides which, in a test used for determining enzymatic albicanyl diphosphate synthase activity, display at least a 1 to 10%, or at least 20%, or at least 50%, or at least 75%, or at least 90% higher or lower albicanyl diphosphate synthase activity, as that of the polypeptides specifically described herein.

"Functional equivalents", according to the invention, also cover particular mutants, which, in at least one sequence position of an amino acid sequences stated herein, have an amino acid that is different from that concretely stated one, but nevertheless possess one of the aforementioned biological activities, as for example enzyme activity. "Functional equivalents" thus comprise mutants obtainable by one or more, like 1 to 20, in particular 1 to 15 or 5 to 10 amino acid additions, substitutions, in particular conservative substitutions, deletions and/or inversions, where the stated changes can occur in any sequence position, provided they lead to a mutant with the profile of properties according to the invention. Functional equivalence is in particular also provided if the activity patterns coincide qualitatively between the mutant and the unchanged polypeptide, i.e. if, for example, interaction with the same agonist or antagonist or substrate, however at a different rate, (i.e. expressed by a $EC_{50}$ or $IC_{50}$ value or any other parameter suitable in the present technical field) is observed. Examples of suitable (conservative) amino acid substitutions are shown in the following table:

| Original residue | Examples of substitution |
| --- | --- |
| Ala | Ser |
| Arg | Lys |
| Asn | Gln; His |
| Asp | Glu |
| Cys | Ser |
| Gln | Asn |
| Glu | Asp |
| Gly | Pro |
| His | Asn; Gln |
| Ile | Leu; Val |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

"Functional equivalents" in the above sense are also "precursors" of the polypeptides described herein, as well as "functional derivatives" and "salts" of the polypeptides.

"Precursors" are in that case natural or synthetic precursors of the polypeptides with or without the desired biological activity.

The expression "salts" means salts of carboxyl groups as well as salts of acid addition of amino groups of the protein molecules according to the invention. Salts of carboxyl groups can be produced in a known way and comprise inorganic salts, for example sodium, calcium, ammonium, iron and zinc salts, and salts with organic bases, for example amines, such as triethanolamine, arginine, lysine, piperidine and the like. Salts of acid addition, for example salts with inorganic acids, such as hydrochloric acid or sulfuric acid and salts with organic acids, such as acetic acid and oxalic acid, are also covered by the invention.

"Functional derivatives" of polypeptides according to the invention can also be produced on functional amino acid side groups or at their N-terminal or C-terminal end using known techniques. Such derivatives comprise for example aliphatic esters of carboxylic acid groups, amides of carboxylic acid groups, obtainable by reaction with ammonia or with a primary or secondary amine; N-acyl derivatives of free amino groups, produced by reaction with acyl groups; or O-acyl derivatives of free hydroxyl groups, produced by reaction with acyl groups.

"Functional equivalents" naturally also comprise polypeptides that can be obtained from other organisms, as well as naturally occurring variants. For example, areas of homologous sequence regions can be established by sequence comparison, and equivalent polypeptides can be determined on the basis of the concrete parameters of the invention.

"Functional equivalents" also comprise "fragments", like individual domains or sequence motifs, of the polypeptides according to the invention, or N- and or C-terminally truncated forms, which may or may not display the desired biological function. Preferably such "fragments" retain the desired biological function at least qualitatively.

"Functional equivalents" are, moreover, fusion proteins, which have one of the polypeptide sequences stated herein or functional equivalents derived there from and at least one further, functionally different, heterologous sequence in functional N-terminal or C-terminal association (i.e. without substantial mutual functional impairment of the fusion protein parts). Non-limiting examples of these heterologous sequences are e.g. signal peptides, histidine anchors or enzymes.

"Functional equivalents" which are also comprised in accordance with the invention are homologs to the specifically disclosed polypeptides. These have at least 60%, preferably at least 75%, in particular at least 80 or 85%, such as, for example, 90, 91, 92, 93, 94, 95, 96, 97, 98 or 99%, homology (or identity) to one of the specifically disclosed amino acid sequences, calculated by the algorithm of Pearson and Lipman, Proc. Natl. Acad, Sci. (USA) 85(8), 1988, 2444-2448. A homology or identity, expressed as a percentage, of a homologous polypeptide according to the invention means in particular an identity, expressed as a percentage, of the amino acid residues based on the total length of one of the amino acid sequences described specifically herein.

The identity data, expressed as a percentage, may also be determined with the aid of BLAST alignments, algorithm blastp (protein-protein BLAST), or by applying the Clustal settings specified herein below.

In the case of a possible protein glycosylation, "functional equivalents" according to the invention comprise polypeptides as described herein in deglycosylated or glycosylated form as well as modified forms that can be obtained by altering the glycosylation pattern.

Functional equivalents or homologues of the polypeptides according to the invention can be produced by mutagenesis, e.g. by point mutation, lengthening or shortening of the protein or as described in more detail below.

Functional equivalents or homologs of the polypeptides according to the invention can be identified by screening combinatorial databases of mutants, for example shortening mutants. For example, a variegated database of protein variants can be produced by combinatorial mutagenesis at the nucleic acid level, e.g. by enzymatic ligation of a mixture of synthetic oligonucleotides. There are a great many methods that can be used for the production of databases of potential homologues from a degenerated oligonucleotide sequence. Chemical synthesis of a degenerated gene sequence can be carried out in an automatic DNA synthesizer, and the synthetic gene can then be ligated in a suitable expression vector. The use of a degenerated genome makes it possible to supply all sequences in a mixture, which code for the desired set of potential protein sequences. Methods of synthesis of degenerated oligonucleotides are known to a person skilled in the art.

In the prior art, several techniques are known for the screening of gene products of combinatorial databases, which were produced by point mutations or shortening, and for the screening of cDNA libraries for gene products with a selected property. These techniques can be adapted for the rapid screening of the gene banks that were produced by combinatorial mutagenesis of homologues according to the invention. The techniques most frequently used for the screening of large gene banks, which are based on a high-throughput analysis, comprise cloning of the gene bank in expression vectors that can be replicated, transformation of the suitable cells with the resultant vector database and expression of the combinatorial genes in conditions in which detection of the desired activity facilitates isolation of the vector that codes for the gene whose product was detected. Recursive Ensemble Mutagenesis (REM), a technique that increases the frequency of functional mutants in the databases, can be used in combination with the screening tests, in order to identify homologues.

An embodiment provided herein provides orthologs and paralogs of polypeptides disclosed herein as well as methods for identifying and isolating such orthologs and paralogs. A definition of the terms "ortholog" and "paralog" is given below and applies to amino acid and nucleic acid sequences.

c. Coding Nucleic Acid Sequences Applicable According to the Invention

In this context the following definitions apply:

The terms "nucleic acid sequence," "nucleic acid," "nucleic acid molecule" and "polynucleotide" are used interchangeably meaning a sequence of nucleotides. A nucleic acid sequence may be a single-stranded or double-stranded deoxyribonucleotide, or ribonucleotide of any length, and include coding and non-coding sequences of a gene, exons, introns, sense and anti-sense complimentary sequences, genomic DNA, cDNA, miRNA, siRNA, mRNA, rRNA, tRNA, recombinant nucleic acid sequences, isolated and purified naturally occurring DNA and/or RNA sequences, synthetic DNA and RNA sequences, fragments, primers and nucleic acid probes. The skilled artisan is aware that the nucleic acid sequences of RNA are identical to the DNA sequences with the difference of thymine (T) being replaced by uracil (U). The term "nucleotide sequence" should also be understood as comprising a polynucleotide molecule or an oligonucleotide molecule in the form of a separate fragment or as a component of a larger nucleic acid.

An "isolated nucleic acid" or "isolated nucleic acid sequence" relates to a nucleic acid or nucleic acid sequence that is in an environment different from that in which the nucleic acid or nucleic acid sequence naturally occurs and can include those that are substantially free from contaminating endogenous material.

The term "naturally-occurring" as used herein as applied to a nucleic acid refers to a nucleic acid that is found in a cell of an organism in nature and which has not been intentionally modified by a human in the laboratory.

A "fragment" of a polynucleotide or nucleic acid sequence refers to contiguous nucleotides that is particularly at least 15 bp, at least 30 bp, at least 40 bp, at least 50 bp and/or at least 60 bp in length of the polynucleotide of an embodiment herein. Particularly the fragment of a polynucleotide comprises at least 25, more particularly at least 50, more particularly at least 75, more particularly at least 100, more particularly at least 150, more particularly at least 200, more particularly at least 300, more particularly at least 400, more particularly at least 500, more particularly at least 600, more particularly at least 700, more particularly at least 800, more particularly at least 900, more particularly at least 1000 contiguous nucleotides of the polynucleotide of an embodiment herein. Without being limited, the fragment of the polynucleotides herein may be used as a PCR primer, and/or as a probe, or for anti-sense gene silencing or RNAi.

As used herein, the term "hybridization" or hybridizes under certain conditions is intended to describe conditions for hybridization and washes under which nucleotide sequences that are significantly identical or homologous to each other remain bound to each other. The conditions may be such that sequences, which are at least about 70%, such as at least about 80%, and such as at least about 85%, 90%, or 95% identical, remain bound to each other. Definitions of low stringency, moderate, and high stringency hybridization conditions are provided herein below. Appropriate hybridization conditions can also be selected by those skilled in the art with minimal experimentation as exemplified in Ausubel et al. (1995, *Current Protocols in Molecular Biology*, John Wiley & Sons, sections 2, 4, and 6). Additionally, stringency conditions are described in Sambrook et al. (1989, *Molecular Cloning: A Laboratory Manual*, 2nd ed., Cold Spring Harbor Press, chapters 7, 9, and 11).

"Recombinant nucleic acid sequences" are nucleic acid sequences that result from the use of laboratory methods (for example, molecular cloning) to bring together genetic material from more than on source, creating or modifying a nucleic acid sequence that does not occur naturally and would not be otherwise found in biological organisms.

"Recombinant DNA technology" refers to molecular biology procedures to prepare a recombinant nucleic acid sequence as described, for instance, in Laboratory Manuals edited by Weigel and Glazebrook, 2002, Cold Spring Harbor Lab Press; and Sambrook et al., 1989, Cold Spring Harbor, N.Y., Cold Spring Harbor Laboratory Press.

The term "gene" means a DNA sequence comprising a region, which is transcribed into a RNA molecule, e.g., an mRNA in a cell, operably linked to suitable regulatory regions, e.g., a promoter. A gene may thus comprise several operably linked sequences, such as a promoter, a 5' leader sequence comprising, e.g., sequences involved in translation initiation, a coding region of cDNA or genomic DNA, introns, exons, and/or a 3'non-translated sequence comprising, e.g., transcription termination sites.

"Polycistronic" refers to nucleic acid molecules, in particular mRNAs that can encode more than one polypeptide separately within the same nucleic acid molecule A "chimeric gene" refers to any gene which is not normally found in nature in a species, in particular, a gene in which one or more parts of the nucleic acid sequence are present that are not associated with each other in nature. For example the promoter is not associated in nature with part or all of the transcribed region or with another regulatory region. The term "chimeric gene" is understood to include expression constructs in which a promoter or transcription regulatory sequence is operably linked to one or more coding sequences or to an antisense, i.e., reverse complement of the sense strand, or inverted repeat sequence (sense and antisense, whereby the RNA transcript forms double stranded RNA upon transcription). The term "chimeric gene" also includes genes obtained through the combination of portions of one or more coding sequences to produce a new gene.

A "3' UTR" or "3' non-translated sequence" (also referred to as "3' untranslated region," or "3'end") refers to the nucleic acid sequence found downstream of the coding sequence of a gene, which comprises, for example, a transcription termination site and (in most, but not all eukaryotic mRNAs) a polyadenylation signal such as AAUAAA or variants thereof. After termination of transcription, the mRNA transcript may be cleaved downstream of the polyadenylation signal and a poly(A) tail may be added, which is involved in the transport of the mRNA to the site of translation, e.g., cytoplasm.

The term "primer" refers to a short nucleic acid sequence that is hybridized to a template nucleic acid sequence and is used for polymerization of a nucleic acid sequence complementary to the template.

The term "selectable marker" refers to any gene which upon expression may be used to select a cell or cells that include the selectable marker. Examples of selectable markers are described below. The skilled artisan will know that different antibiotic, fungicide, auxotrophic or herbicide selectable markers are applicable to different target species.

The invention also relates to nucleic acid sequences that code for polypeptides as defined herein.

In particular, the invention also relates to nucleic acid sequences (single-stranded and double-stranded DNA and RNA sequences, e.g. cDNA, genomic DNA and mRNA), coding for one of the above polypeptides and their functional equivalents, which can be obtained for example using artificial nucleotide analogs.

The invention relates both to isolated nucleic acid molecules, which code for polypeptides according to the invention or biologically active segments thereof, and to nucleic acid fragments, which can be used for example as hybridization probes or primers for identifying or amplifying coding nucleic acids according to the invention.

The present invention also relates to nucleic acids with a certain degree of "identity" to the sequences specifically disclosed herein. "Identity" between two nucleic acids means identity of the nucleotides, in each case over the entire length of the nucleic acid.

The "identity" between two nucleotide sequences (the same applies to peptide or amino acid sequences) is a function of the number of nucleotide residues (or amino acid residues) or that are identical in the two sequences when an alignment of these two sequences has been generated. Identical residues are defined as residues that are the same in the two sequences in a given position of the alignment. The percentage of sequence identity, as used herein, is calculated from the optimal alignment by taking the number of residues identical between two sequences dividing it by the total number of residues in the shortest sequence and multiplying by 100. The optimal alignment is the alignment in which the percentage of identity is the highest possible. Gaps may be introduced into one or both sequences in one or more positions of the alignment to obtain the optimal alignment. These gaps are then taken into account as non-identical residues for the calculation of the percentage of sequence identity. Alignment for the purpose of determining the percentage of amino acid or nucleic acid sequence identity can be achieved in various ways using computer programs and for instance publicly available computer programs available on the world wide web.

Particularly, the BLAST program (Tatiana et al, *FEMS Microbiol Lett.*, 1999, 174:247-250, 1999) set to the default parameters, available from the National Center for Biotechnology Information (NCBI) website at ncbi.nlm.nih.gov/BLAST/bl2seq/wblast2.cgi, can be used to obtain an optimal alignment of protein or nucleic acid sequences and to calculate the percentage of sequence identity.

In another example the identity may be calculated by means of the Vector NTI Suite 7.1 program of the company Informax (USA) employing the Clustal Method (Higgins D G, Sharp P M. ((1989))) with the following settings:

Multiple alignment parameters:

| | |
|---|---|
| Gap opening penalty | 10 |
| Gap extension penalty | 10 |
| Gap separation penalty range | 8 |
| Gap separation penalty | off |
| % identity for alignment delay | 40 |
| Residue specific gaps | off |
| Hydrophilic residue gap | off |
| Transition weighing | 0 |

Pairwise alignment parameter:

| | |
|---|---|
| FAST algorithm | on |
| K-tuple size | 1 |
| Gap penalty | 3 |
| Window size | 5 |
| Number of best diagonals | 5 |

Alternatively the identity may be determined according to Chenna, et al. (2003), the web page: http://www.ebi.ac.uk/Tools/clustalw/index.html# and the following settings

| | |
|---|---|
| DNA Gap Open Penalty | 15.0 |
| DNA Gap Extension Penalty | 6.66 |
| DNA Matrix | Identity |
| Protein Gap Open Penalty | 10.0 |
| Protein Gap Extension Penalty | 0.2 |
| Protein matrix | Gonnet |
| Protein/DNA ENDGAP | −1 |
| Protein/DNA GAPDIST | 4 |

All the nucleic acid sequences mentioned herein (single-stranded and double-stranded DNA and RNA sequences, for example cDNA and mRNA) can be produced in a known way by chemical synthesis from the nucleotide building blocks, e.g. by fragment condensation of individual overlapping, complementary nucleic acid building blocks of the double helix. Chemical synthesis of oligonucleotides can, for example, be performed in a known way, by the phosphoamidite method (Voet, Voet, 2nd edition, Wiley Press, New York, pages 896-897). The accumulation of synthetic oligonucleotides and filling of gaps by means of the Klenow fragment of DNA polymerase and ligation reactions as well as general cloning techniques are described in Sambrook et al. (1989), see below.

The nucleic acid molecules according to the invention can in addition contain non-translated sequences from the 3' and/or 5' end of the coding genetic region.

The invention further relates to the nucleic acid molecules that are complementary to the concretely described nucleotide sequences or a segment thereof.

The nucleotide sequences according to the invention make possible the production of probes and primers that can be used for the identification and/or cloning of homologous sequences in other cellular types and organisms. Such probes or primers generally comprise a nucleotide sequence region which hybridizes under "stringent" conditions (as defined herein elsewhere) on at least about 12, preferably at least about 25, for example about 40, 50 or 75 successive nucleotides of a sense strand of a nucleic acid sequence according to the invention or of a corresponding antisense strand.

"Homologous" sequences include orthologous or paralogous sequences. Methods of identifying orthologs or paralogs including phylogenetic methods, sequence similarity and hybridization methods are known in the art and are described herein.

"Paralogs" result from gene duplication that gives rise to two or more genes with similar sequences and similar functions. Paralogs typically cluster together and are formed by duplications of genes within related plant species. Paralogs are found in groups of similar genes using pair-wise Blast analysis or during phylogenetic analysis of gene families using programs such as CLUSTAL. In paralogs, consensus sequences can be identified characteristic to sequences within related genes and having similar functions of the genes.

"Orthologs", or orthologous sequences, are sequences similar to each other because they are found in species that descended from a common ancestor. For instance, plant species that have common ancestors are known to contain many enzymes that have similar sequences and functions. The skilled artisan can identify orthologous sequences and predict the functions of the orthologs, for example, by constructing a polygenic tree for a gene family of one species using CLUSTAL or BLAST programs. A method for identifying or confirming similar functions among homologous sequences is by comparing of the transcript profiles in host cells or organisms, such as plants or microorganisms, overexpressing or lacking (in knockouts/knockdowns) related polypeptides. The skilled person will understand that genes having similar transcript profiles, with greater than 50% regulated transcripts in common, or with greater than 70% regulated transcripts in common, or greater than 90% regulated transcripts in common will have similar functions. Homologs, paralogs, orthologs and any other variants of the sequences herein are expected to function in a similar manner by making the host cells, organism such as plants or microorganisms producing terpene synthase proteins.

The term "selectable marker" refers to any gene which upon expression may be used to select a cell or cells that include the selectable marker. Examples of selectable markers are described below. The skilled artisan will know that different antibiotic, fungicide, auxotrophic or herbicide selectable markers are applicable to different target species.

An "isolated" nucleic acid molecule is separated from other nucleic acid molecules that are present in the natural source of the nucleic acid and can moreover be substantially free from other cellular material or culture medium, if it is being produced by recombinant techniques, or can be free from chemical precursors or other chemicals, if it is being synthesized chemically.

A nucleic acid molecule according to the invention can be isolated by means of standard techniques of molecular biology and the sequence information supplied according to the invention. For example, cDNA can be isolated from a suitable cDNA library, using one of the concretely disclosed complete sequences or a segment thereof as hybridization probe and standard hybridization techniques (as described for example in Sambrook, (1989)).

In addition, a nucleic acid molecule comprising one of the disclosed sequences or a segment thereof, can be isolated by the polymerase chain reaction, using the oligonucleotide primers that were constructed on the basis of this sequence. The nucleic acid amplified in this way can be cloned in a suitable vector and can be characterized by DNA sequencing. The oligonucleotides according to the invention can also be produced by standard methods of synthesis, e.g. using an automatic DNA synthesizer.

Nucleic acid sequences according to the invention or derivatives thereof, homologues or parts of these sequences, can for example be isolated by usual hybridization techniques or the PCR technique from other bacteria, e.g. via genomic or cDNA libraries. These DNA sequences hybridize in standard conditions with the sequences ac-cording to the invention.

"Hybridize" means the ability of a polynucleotide or oligonucleotide to bind to an almost complementary sequence in standard conditions, whereas nonspecific binding does not occur between non-complementary partners in these conditions. For this, the sequences can be 90-100% complementary. The property of complementary sequences of being able to bind specifically to one another is utilized for example in Northern Blotting or Southern Blotting or in primer binding in PCR or RT-PCR.

Short oligonucleotides of the conserved regions are used advantageously for hybridization. However, it is also possible to use longer fragments of the nucleic acids according to the invention or the complete sequences for the hybridization. These "standard conditions" vary depending on the nucleic acid used (oligonucleotide, longer fragment or complete sequence) or depending on which type of nucleic acid—DNA or RNA—is used for hybridization. For example, the melting temperatures for DNA:DNA hybrids are approx. 10° C. lower than those of DNA:RNA hybrids of the same length.

For example, depending on the particular nucleic acid, standard conditions mean temperatures between 42 and 58° C. in an aqueous buffer solution with a concentration between 0.1 to 5×SSC (1×SSC=0.15 M NaCl, 15 mM sodium citrate, pH 7.2) or additionally in the presence of 50% formamide, for example 42° C. in 5×SSC, 50% formamide. Advantageously, the hybridization conditions for DNA:DNA hybrids are 0.1×SSC and temperatures between about 20° C. to 45° C., preferably between about 30° C. to 45° C. For DNA:RNA hybrids the hybridization conditions are advantageously 0.1×SSC and temperatures between about 30° C. to 55° C., preferably between about 45° C. to 55° C. These stated temperatures for hybridization are examples of calculated melting temperature values for a nucleic acid with a length of approx. 100 nucleotides and a G+C content of 50% in the absence of formamide. The experimental conditions for DNA hybridization are described in relevant genetics textbooks, for example Sambrook et al., 1989, and can be calculated using formulae that are known by a person skilled in the art, for example depending on the length of the nucleic acids, the type of hybrids or the G+C content. A person skilled in the art can obtain further information on hybridization from the following textbooks: Ausubel et al. (eds), (1985), Brown (ed) (1991).

"Hybridization" can in particular be carried out under stringent conditions. Such hybridization conditions are for example described in Sambrook (1989), or in Current Protocols in Molecular Biology, John Wiley & Sons, N.Y. (1989), 6.3.1-6.3.6.

As used herein, the term hybridization or hybridizes under certain conditions is intended to describe conditions for hybridization and washes under which nucleotide sequences that are significantly identical or homologous to each other remain bound to each other. The conditions may be such that sequences, which are at least about 70%, such as at least about 80%, and such as at least about 85%, 90%, or 95% identical, remain bound to each other. Definitions of low stringency, moderate, and high stringency hybridization conditions are provided herein.

Appropriate hybridization conditions can be selected by those skilled in the art with minimal experimentation as exemplified in Ausubel et al. (1995, *Current Protocols in Molecular Biology*, John Wiley & Sons, sections 2, 4, and 6). Additionally, stringency conditions are described in Sambrook et al. (1989, *Molecular Cloning: A Laboratory Manual*, 2nd ed., Cold Spring Harbor Press, chapters 7, 9, and 11).

As used herein, defined conditions of low stringency are as follows. Filters containing DNA are pretreated for 6 h at 40° C. in a solution containing 35% formamide, 5×SSC, 50 mM Tris-HCl (pH 7.5), 5 mM EDTA, 0.1% PVP, 0.1% Ficoll, 1% BSA, and 500 µg/ml denatured salmon sperm DNA. Hybridizations are carried out in the same solution with the following modifications: 0.02% PVP, 0.02% Ficoll, 0.2% BSA, 100 µg/ml salmon sperm DNA, 10% (wt/vol) dextran sulfate, and 5-20×106 32P-labeled probe is used. Filters are incubated in hybridization mixture for 18-20 h at 40° C., and then washed for 1.5 h at 55° C. In a solution containing 2×SSC, 25 mM Tris-HCl (pH 7.4), 5 mM EDTA, and 0.1% SDS. The wash solution is replaced with fresh solution and incubated an additional 1.5 h at 60° C. Filters are blotted dry and exposed for autoradiography.

As used herein, defined conditions of moderate stringency are as follows. Filters containing DNA are pretreated for 7 h at 50° C. in a solution containing 35% formamide, 5×SSC, 50 mM Tris-HCl (pH 7.5), 5 mM EDTA, 0.1% PVP, 0.1% Ficoll, 1% BSA, and 500 µg/ml denatured salmon sperm DNA. Hybridizations are carried out in the same solution with the following modifications: 0.02% PVP, 0.02% Ficoll, 0.2% BSA, 100 µg/ml salmon sperm DNA, 10% (wt/vol) dextran sulfate, and 5-20×106 32P-labeled probe is used. Filters are incubated in hybridization mixture for 30 h at 50° C., and then washed for 1.5 h at 55° C. In a solution containing 2×SSC, 25 mM Tris-HCl (pH 7.4), 5 mM EDTA, and 0.1% SDS. The wash solution is replaced with fresh solution and incubated an additional 1.5 h at 60° C. Filters are blotted dry and exposed for autoradiography.

As used herein, defined conditions of high stringency are as follows. Prehybridization of filters containing DNA is carried out for 8 h to overnight at 65° C. in buffer composed of 6×SSC, 50 mM Tris-HCl (pH 7.5), 1 mM EDTA, 0.02% PVP, 0.02% Ficoll, 0.02% BSA, and 500 µg/ml denatured salmon sperm DNA. Filters are hybridized for 48 h at 65° C. in the prehybridization mixture containing 100 µg/ml denatured salmon sperm DNA and 5-20×106 cpm of 32P-labeled probe. Washing of filters is done at 37° C. for 1 h in a solution containing 2×SSC, 0.01% PVP, 0.01% Ficoll, and 0.01% BSA. This is followed by a wash in 0.1×SSC at 50° C. for 45 minutes.

Other conditions of low, moderate, and high stringency well known in the art (e.g., as employed for cross-species hybridizations) may be used if the above conditions are inappropriate (e.g., as employed for cross-species hybridizations).

A detection kit for nucleic acid sequences encoding a polypeptide of the invention may include primers and/or probes specific for nucleic acid sequences encoding the polypeptide, and an associated protocol to use the primers and/or probes to detect nucleic acid sequences encoding the polypeptide in a sample. Such detection kits may be used to determine whether a plant, organism, microorganism or cell has been modified, i.e., transformed with a sequence encoding the polypeptide.

To test a function of variant DNA sequences according to an embodiment herein, the sequence of interest is operably linked to a selectable or screenable marker gene and expression of said reporter gene is tested in transient expression assays, for example, with microorganisms or with protoplasts or in stably transformed plants.

The invention also relates to derivatives of the concretely disclosed or derivable nucleic acid sequences.

Thus, further nucleic acid sequences according to the invention can be derived from the sequences specifically disclosed herein and can differ from it by one or more, like 1 to 20, in particular 1 to 15 or 5 to 10 additions, substitutions, insertions or deletions of one or several (like for example 1 to 10) nucleotides, and furthermore code for polypeptides with the desired profile of properties.

The invention also encompasses nucleic acid sequences that comprise so-called silent mutations or have been altered, in comparison with a concretely stated sequence, according to the codon usage of a special original or host organism.

According to a particular embodiment of the invention variant nucleic acids may be prepared in order to adapt its nucleotide sequence to a specific expression system. For example, bacterial expression systems are known to more efficiently express polypeptides if amino acids are encoded by particular codons. Due to the degeneracy of the genetic code, more than one codon may encode the same amino acid sequence, multiple nucleic acid sequences can code for the same protein or polypeptide, all these DNA sequences being encompassed by an embodiment herein. Where appropriate, the nucleic acid sequences encoding the polypeptides described herein may be optimized for increased expression in the host cell. For example, nucleic acids of an embodiment herein may be synthesized using codons particular to a host for improved expression.

The invention also encompasses naturally occurring variants, e.g. splicing variants or allelic variants, of the sequences described therein.

Allelic variants may have at least 60% homology at the level of the derived amino acid, preferably at least 80% homology, quite especially preferably at least 90% homology over the entire sequence range (regarding homology at the amino acid level, reference should be made to the details given above for the polypeptides). Advantageously, the homologies can be higher over partial regions of the sequences.

The invention also relates to sequences that can be obtained by conservative nucleotide substitutions (i.e. as a result thereof the amino acid in question is replaced by an amino acid of the same charge, size, polarity and/or solubility).

The invention also relates to the molecules derived from the concretely disclosed nucleic acids by sequence polymorphisms. Such genetic polymorphisms may exist in cells from different populations or within a population due to natural allelic variation. Allelic variants may also include functional equivalents. These natural variations usually produce a variance of 1 to 5% in the nucleotide sequence of a gene. Said polymorphisms may lead to changes in the amino acid sequence of the polypeptides disclosed herein. Allelic variants may also include functional equivalents.

Furthermore, derivatives are also to be understood to be homologs of the nucleic acid sequences according to the invention, for example animal, plant, fungal or bacterial homologs, shortened sequences, single-stranded DNA or RNA of the coding and noncoding DNA sequence. For example, homologs have, at the DNA level, a homology of at least 40%, preferably of at least 60%, especially preferably of at least 70%, quite especially preferably of at least 80% over the entire DNA region given in a sequence specifically disclosed herein.

Moreover, derivatives are to be understood to be, for example, fusions with promoters. The promoters that are added to the stated nucleotide sequences can be modified by at least one nucleotide exchange, at least one insertion, inversion and/or deletion, though without impairing the functionality or efficacy of the promoters. Moreover, the efficacy of the promoters can be increased by altering their sequence or can be exchanged completely with more effective promoters even of organisms of a different genus.

d. Generation of Functional Polypeptide Mutants

Moreover, a person skilled in the art is familiar with methods for generating functional mutants, that is to say nucleotide sequences which code for a polypeptide with at least 40%, 45%, 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98% or 99% sequence identity to anyone of amino acid related SEQ ID NOs as disclosed herein and/or encoded by a nucleic acid molecule comprising a nucleotide sequence having at least 70% sequence identity to anyone of the nucleotide related SEQ ID NOs as disclosed herein.

Depending on the technique used, a person skilled in the art can introduce entirely random or else more directed mutations into genes or else noncoding nucleic acid regions (which are for example important for regulating expression) and subsequently generate genetic libraries. The methods of molecular biology required for this purpose are known to the skilled worker and for example described in Sambrook and Russell, Molecular Cloning. 3rd Edition, Cold Spring Harbor Laboratory Press 2001.

Methods for modifying genes and thus for modifying the polypeptide encoded by them have been known to the skilled worker for a long time, such as, for example
 site-specific mutagenesis, where individual or several nucleotides of a gene are replaced in a directed fashion (Trower M K (Ed.) 1996; In vitro mutagenesis protocols. Humana Press, New Jersey),
 saturation mutagenesis, in which a codon for any amino acid can be exchanged or added at any point of a gene (Kegler-Ebo D M, Docktor C M, DiMaio D (1994) Nucleic Acids Res 22:1593; Barettino D, Feigenbutz M, Valcárel R, Stunnenberg H G (1994) Nucleic Acids Res 22:541; Bank S (1995) Mol Biotechnol 3:1),
 error-prone polymerase chain reaction, where nucleotide sequences are mutated by error-prone DNA polymerases (Eckert K A, Kunkel T A (1990) Nucleic Acids Res 18:3739);

the SeSaM method (sequence saturation method), in which preferred exchanges are prevented by the polymerase. Schenk et al., Biospektrum, Vol. 3, 2006, 277-279 the passaging of genes in mutator strains, in which, for example owing to defective DNA repair mechanisms, there is an increased mutation rate of nucleotide sequences (Greener A, Callahan M, Jerpseth B (1996) An efficient random mutagenesis technique using an *E. coli* mutator strain. In: Trower M K (Ed.) In vitro mutagenesis protocols. Humana Press, New Jersey), or DNA shuffling, in which a pool of closely related genes is formed and digested and the fragments are used as templates for a polymerase chain reaction in which, by repeated strand separation and reassociation, full-length mosaic genes are ultimately generated (Stemmer W P C (1994) Nature 370:389; Stemmer W P C (1994) Proc Natl Acad Sci USA 91:10747).

Using so-called directed evolution (described, inter alia, in Reetz M T and Jaeger K-E (1999), Topics Curr Chem 200:31; Zhao H, Moore J C, Volkov A A, Arnold F H (1999), Methods for optimizing industrial polypeptides by directed evolution, In: Demain A L, Davies J E (Ed.) Manual of industrial microbiology and biotechnology. American Society for Microbiology), a skilled worker can produce functional mutants in a directed manner and on a large scale. To this end, in a first step, gene libraries of the respective polypeptides are first produced, for example using the methods given above. The gene libraries are expressed in a suitable way, for example by bacteria or by phage display systems.

The relevant genes of host organisms which express functional mutants with properties that largely correspond to the desired properties can be submitted to another mutation cycle. The steps of the mutation and selection or screening can be repeated iteratively until the present functional mutants have the desired properties to a sufficient extent. Using this iterative procedure, a limited number of mutations, for example 1, 2, 3, 4 or 5 mutations, can be performed in stages and assessed and selected for their influence on the activity in question. The selected mutant can then be submitted to a further mutation step in the same way. In this way, the number of individual mutants to be investigated can be reduced significantly.

The results according to the invention also provide important information relating to structure and sequence of the relevant polypeptides, which is required for generating, in a targeted fashion, further polypeptides with desired modified properties. In particular, it is possible to define so-called "hot spots", i.e. sequence segments that are potentially suitable for modifying a property by introducing targeted mutations.

Information can also be deduced regarding amino acid sequence positions, in the region of which mutations can be effected that should probably have little effect on the activity, and can be designated as potential "silent mutations".

e. Constructs for Expressing Polypeptides of the Invention

In this context the following definitions apply:

"Expression of a gene" encompasses "heterologous expression" and "over-expression" and involves transcription of the gene and translation of the mRNA into a protein. Overexpression refers to the production of the gene product as measured by levels of mRNA, polypeptide and/or enzyme activity in transgenic cells or organisms that exceeds levels of production in non-transformed cells or organisms of a similar genetic background.

"Expression vector" as used herein means a nucleic acid molecule engineered using molecular biology methods and recombinant DNA technology for delivery of foreign or exogenous DNA into a host cell. The expression vector typically includes sequences required for proper transcription of the nucleotide sequence. The coding region usually codes for a protein of interest but may also code for an RNA, e.g., an antisense RNA, siRNA and the like.

An "expression vector" as used herein includes any linear or circular recombinant vector including but not limited to viral vectors, bacteriophages and plasmids. The skilled person is capable of selecting a suitable vector according to the expression system. In one embodiment, the expression vector includes the nucleic acid of an embodiment herein operably linked to at least one "regulatory sequence", which controls transcription, translation, initiation and termination, such as a transcriptional promoter, operator or enhancer, or an mRNA ribosomal binding site and, optionally, including at least one selection marker. Nucleotide sequences are "operably linked" when the regulatory sequence functionally relates to the nucleic acid of an embodiment herein.

An "expression system" as used herein encompasses any combination of nucleic acid molecules required for the expression of one, or the co-expression of two or more polypeptides either in vivo of a given expression host, or in vitro. The respective coding sequences may either be located on a single nucleic acid molecule or vector, as for example a vector containing multiple cloning sites, or on a polycistronic nucleic acid, or may be distributed over two or more physically distinct vectors.

As used herein, the terms "amplifying" and "amplification" refer to the use of any suitable amplification methodology for generating or detecting recombinant of naturally expressed nucleic acid, as described in detail, below. For example, the invention provides methods and reagents (e.g., specific degenerate oligonucleotide primer pairs, oligo dT primer) for amplifying (e.g., by polymerase chain reaction, PCR) naturally expressed (e.g., genomic DNA or mRNA) or recombinant (e.g., cDNA) nucleic acids of the invention in vivo, ex vivo or in vitro.

"Regulatory sequence" refers to a nucleic acid sequence that determines expression level of the nucleic acid sequences of an embodiment herein and is capable of regulating the rate of transcription of the nucleic acid sequence operably linked to the regulatory sequence. Regulatory sequences comprise promoters, enhancers, transcription factors, promoter elements and the like.

A "promoter", a "nucleic acid with promoter activity" or a "promoter sequence" is understood as meaning, in accordance with the invention, a nucleic acid which, when functionally linked to a nucleic acid to be transcribed, regulates the transcription of said nucleic acid. "Promoter" in particular refers to a nucleic acid sequence that controls the expression of a coding sequence by providing a binding site for RNA polymerase and other factors required for proper transcription including without limitation transcription factor binding sites, repressor and activator protein binding sites. The meaning of the term promoter also includes the term "promoter regulatory sequence". Promoter regulatory sequences may include upstream and downstream elements that may influences transcription, RNA processing or stability of the associated coding nucleic acid sequence. Promoters include naturally-derived and synthetic sequences. The coding nucleic acid sequences is usually located downstream of the promoter with respect to the direction of the transcription starting at the transcription initiation site.

In this context, a "functional" or "operative" linkage is understood as meaning for example the sequential arrangement of one of the nucleic acids with a regulatory sequence. For example the sequence with promoter activity and of a nucleic acid sequence to be transcribed and optionally further regulatory elements, for example nucleic acid sequences which ensure the transcription of nucleic acids, and for example a terminator, are linked in such a way that each of the regulatory elements can perform its function upon transcription of the nucleic acid sequence. This does not necessarily require a direct linkage in the chemical sense. Genetic control sequences, for example enhancer sequences, can even exert their function on the target sequence from more remote positions or even from other DNA molecules. Preferred arrangements are those in which the nucleic acid sequence to be transcribed is positioned behind (i.e. at the 3'-end of) the promoter sequence so that the two sequences are joined together covalently. The distance between the promoter sequence and the nucleic acid sequence to be expressed recombinantly can be smaller than 200 base pairs, or smaller than 100 base pairs or smaller than 50 base pairs.

In addition to promoters and terminator, the following may be mentioned as examples of other regulatory elements: targeting sequences, enhancers, polyadenylation signals, selectable markers, amplification signals, replication origins and the like. Suitable regulatory sequences are described, for example, in Goeddel, Gene Expression Technology: Methods in Enzymology 185, Academic Press, San Diego, Calif. (1990).

The term "constitutive promoter" refers to an unregulated promoter that allows for continual transcription of the nucleic acid sequence it is operably linked to.

As used herein, the term "operably linked" refers to a linkage of polynucleotide elements in a functional relationship. A nucleic acid is "operably linked" when it is placed into a functional relationship with another nucleic acid sequence. For instance, a promoter, or rather a transcription regulatory sequence, is operably linked to a coding sequence if it affects the transcription of the coding sequence. Operably linked means that the DNA sequences being linked are typically contiguous. The nucleotide sequence associated with the promoter sequence may be of homologous or heterologous origin with respect to the plant to be transformed. The sequence also may be entirely or partially synthetic. Regardless of the origin, the nucleic acid sequence associated with the promoter sequence will be expressed or silenced in accordance with promoter properties to which it is linked after binding to the polypeptide of an embodiment herein. The associated nucleic acid may code for a protein that is desired to be expressed or suppressed throughout the organism at all times or, alternatively, at a specific time or in specific tissues, cells, or cell compartment. Such nucleotide sequences particularly encode proteins conferring desirable phenotypic traits to the host cells or organism altered or transformed therewith. More particularly, the associated nucleotide sequence leads to the production of the product or products of interest as herein defined in the cell or organism. Particularly, the nucleotide sequence encodes a polypeptide having an enzyme activity as herein defined.

The nucleotide sequence as described herein above may be part of an "expression cassette". The terms "expression cassette" and "expression construct" are used synonymously. The (preferably recombinant) expression construct contains a nucleotide sequence which encodes a polypeptide according to the invention and which is under genetic control of regulatory nucleic acid sequences.

In a process applied according to the invention, the expression cassette may be part of an "expression vector", in particular of a recombinant expression vector.

An "expression unit" is understood as meaning, in accordance with the invention, a nucleic acid with expression activity which comprises a promoter as defined herein and, after functional linkage with a nucleic acid to be expressed or a gene, regulates the expression, i.e. the transcription and the translation of said nucleic acid or said gene. It is therefore in this connection also referred to as a "regulatory nucleic acid sequence". In addition to the promoter, other regulatory elements, for example enhancers, can also be present.

An "expression cassette" or "expression construct" is understood as meaning, in accordance with the invention, an expression unit which is functionally linked to the nucleic acid to be expressed or the gene to be expressed. In contrast to an expression unit, an expression cassette therefore comprises not only nucleic acid sequences which regulate transcription and translation, but also the nucleic acid sequences that are to be expressed as protein as a result of transcription and translation.

The terms "expression" or "overexpression" describe, in the context of the invention, the production or increase in intracellular activity of one or more polypeptides in a microorganism, which are encoded by the corresponding DNA. To this end, it is possible for example to introduce a gene into an organism, replace an existing gene with another gene, increase the copy number of the gene(s), use a strong promoter or use a gene which encodes for a corresponding polypeptide with a high activity; optionally, these measures can be combined.

Preferably such constructs according to the invention comprise a promoter 5'-upstream of the respective coding sequence and a terminator sequence 3'-downstream and optionally other usual regulatory elements, in each case in operative linkage with the coding sequence.

Nucleic acid constructs according to the invention comprise in particular a sequence coding for a polypeptide for example derived from the amino acid related SEQ ID NOs as described therein or the reverse complement thereof, or derivatives and homologs thereof and which have been linked operatively or functionally with one or more regulatory signals, advantageously for controlling, for example increasing, gene expression.

In addition to these regulatory sequences, the natural regulation of these sequences may still be present before the actual structural genes and optionally may have been genetically modified so that the natural regulation has been switched off and expression of the genes has been enhanced. The nucleic acid construct may, however, also be of simpler construction, i.e. no additional regulatory signals have been inserted before the coding sequence and the natural promoter, with its regulation, has not been removed. Instead, the natural regulatory sequence is mutated such that regulation no longer takes place and the gene expression is increased.

A preferred nucleic acid construct advantageously also comprises one or more of the already mentioned "enhancer" sequences in functional linkage with the promoter, which sequences make possible an enhanced expression of the nucleic acid sequence. Additional advantageous sequences may also be inserted at the 3'-end of the DNA sequences, such as further regulatory elements or terminators. One or more copies of the nucleic acids according to the invention may be present in a construct. In the construct, other markers, such as genes which complement auxotrophisms or antibiotic resistances, may also optionally be present so as to select for the construct.

Examples of suitable regulatory sequences are present in promoters such as cos, tac, trp, tet, trp-tet, lpp, lac, lpp-lac, lacI$^q$, T7, T5, T3, gal, trc, ara, rhaP (rhaP$_{BAD}$)SP6, lambda-P$_R$ or in the lambda-P$_L$ promoter, and these are advantageously employed in Gram-negative bacteria. Further advantageous regulatory sequences are present for example in the Gram-positive promoters amy and SPO2, in the yeast or fungal promoters ADC1, MFalpha, AC, P-60, CYC1, GAPDH, TEF, rp28, ADH. Artificial promoters may also be used for regulation.

For expression in a host organism, the nucleic acid construct is inserted advantageously into a vector such as, for example, a plasmid or a phage, which makes possible optimal expression of the genes in the host. Vectors are also understood as meaning, in addition to plasmids and phages, all the other vectors which are known to the skilled worker, that is to say for example viruses such as SV40, CMV, baculovirus and adenovirus, transposons, IS elements, phasmids, cosmids and linear or circular DNA or artificial chromosomes. These vectors are capable of replicating autonomously in the host organism or else chromosomally. These vectors are a further development of the invention. Binary or cpo-integration vectors are also applicable.

Suitable plasmids are, for example, in *E. coli* pLG338, pACYC184, pBR322, pUC18, pUC19, pKC30, pRep4, pHS1, pKK223-3, pDHE19.2, pHS2, pPLc236, pMBL24, pLG200, pUR290, pIN-III$^{113}$-B1, λgt11 or pBdCI, in *Streptomyces* pIJ101, pIJ364, pIJ702 or pIJ361, in *Bacillus* pUB110, pC194 or pBD214, in *Corynebacterium* pSA77 or pAJ667, in fungi pALS1, pIL2 or pBB116, in yeasts 2alphaM, pAG-1, YEp6, YEp13 or pEMBLYe23 or in plants pLGV23, pGHlac$^+$, pBIN19, pAK2004 or pDH51. The abovementioned plasmids are a small selection of the plasmids which are possible. Further plasmids are well known to the skilled worker and can be found for example in the book Cloning Vectors (Eds. Pouwels P. H. et al. Elsevier, Amsterdam-New York-Oxford, 1985, ISBN 0 444 904018).

In a further development of the vector, the vector which comprises the nucleic acid construct according to the invention or the nucleic acid according to the invention can advantageously also be introduced into the microorganisms in the form of a linear DNA and integrated into the host organism's genome via heterologous or homologous recombination. This linear DNA can consist of a linearized vector such as a plasmid or only of the nucleic acid construct or the nucleic acid according to the invention.

For optimal expression of heterologous genes in organisms, it is advantageous to modify the nucleic acid sequences to match the specific "codon usage" used in the organism. The "codon usage" can be determined readily by computer evaluations of other, known genes of the organism in question.

An expression cassette according to the invention is generated by fusing a suitable promoter to a suitable coding nucleotide sequence and a terminator or polyadenylation signal. Customary recombination and cloning techniques are used for this purpose, as are described, for example, in T. Maniatis, E. F. Fritsch and J. Sambrook, Molecular Cloning: A Laboratory Manual, Cold Spring Harbor Laboratory, Cold Spring Harbor, N.Y. (1989) and in T. J. Silhavy, M. L. Berman and L. W. Enquist, Experiments with Gene Fusions, Cold Spring Harbor Laboratory, Cold Spring Harbor, N.Y. (1984) and in Ausubel, F. M. et al., Current Protocols in Molecular Biology, Greene Publishing Assoc. and Wiley Interscience (1987).

For expression in a suitable host organism, the recombinant nucleic acid construct or gene construct is advantageously inserted into a host-specific vector which makes possible optimal expression of the genes in the host. Vectors are well known to the skilled worker and can be found for example in "cloning vectors" (Pouwels P. H. et al., Ed., Elsevier, Amsterdam-New York-Oxford, 1985).

An alternative embodiment of an embodiment herein provides a method to "alter gene expression" in a host cell. For instance, the polynucleotide of an embodiment herein may be enhanced or overexpressed or induced in certain contexts (e.g. upon exposure to certain temperatures or culture conditions) in a host cell or host organism.

Alteration of expression of a polynucleotide provided herein may also result in ectopic expression which is a different expression pattern in an altered and in a control or wild-type organism. Alteration of expression occurs from interactions of polypeptide of an embodiment herein with exogenous or endogenous modulators, or as a result of chemical modification of the polypeptide. The term also refers to an altered expression pattern of the polynucleotide of an embodiment herein which is altered below the detection level or completely suppressed activity.

In one embodiment, provided herein is also an isolated, recombinant or synthetic polynucleotide encoding a polypeptide or variant polypeptide provided herein.

In one embodiment, several polypeptide encoding nucleic acid sequences are co-expressed in a single host, particularly under control of different promoters. In another embodiment, several polypeptide encoding nucleic acid sequences can be present on a single transformation vector or be co-transformed at the same time using separate vectors and selecting transformants comprising both chimeric genes. Similarly, one or polypeptide encoding genes may be expressed in a single plant, cell, microorganism or organism together with other chimeric genes.

f. Hosts to be Applied for the Present Invention

Depending on the context, the term "host" can mean the wild-type host or a genetically altered, recombinant host or both.

In principle, all prokaryotic or eukaryotic organisms may be considered as host or recombinant host organisms for the nucleic acids or the nucleic acid constructs according to the invention.

Using the vectors according to the invention, recombinant hosts can be produced, which are for example transformed with at least one vector according to the invention and can be used for producing the polypeptides according to the invention. Advantageously, the recombinant constructs according to the invention, described above, are introduced into a suitable host system and expressed. Preferably common cloning and transfection methods, known by a person skilled in the art, are used, for example co-precipitation, protoplast fusion, electroporation, retroviral transfection and the like, for expressing the stated nucleic acids in the respective expression system. Suitable systems are described for example in Current Protocols in Molecular Biology, F. Ausubel et al., Ed., Wiley Interscience, New York 1997, or Sambrook et al. Molecular Cloning: A Laboratory Manual. 2nd edition, Cold Spring Harbor Laboratory, Cold Spring Harbor Laboratory Press, Cold Spring Harbor, N.Y., 1989.

Advantageously, microorganisms such as bacteria, fungi or yeasts are used as host organisms. Advantageously, gram-positive or gram-negative bacteria are used, preferably bacteria of the families Enterobacteriaceae, Pseudomonadaceae, Rhizobiaceae, Streptomycetaceae, Streptococcaceae or Nocardiaceae, especially preferably bacteria of the genera *Escherichia, Pseudomonas, Streptomyces, Lactococcus, Nocardia, Burkholderia, Salmonella, Agrobacterium, Clostridium* or *Rhodococcus*. The genus and species *Escherichia coli* is quite especially preferred. Furthermore, other advantageous bacteria are to be found in the group of alpha-Proteobacteria, beta-Proteobacteria or gamma-Proteobacteria. Advantageously also yeasts of families like *Saccharomyces* or *Pichia* are suitable hosts.

Alternatively, entire plants or plant cells may serve as natural or recombinant host. As non-limiting examples the following plants or cells derived therefrom may be mentioned the genera *Nicotiana*, in particular *Nicotiana benthamiana* and *Nicotiana tabacum* (tobacco); as well as *Arabidopsis*, in particular *Arabidopsis thaliana*.

Depending on the host organism, the organisms used in the method according to the invention are grown or cultured in a manner known by a person skilled in the art. Culture can be batchwise, semi-batchwise or continuous. Nutrients can be present at the beginning of fermentation or can be supplied later, semicontinuously or continuously. This is also described in more detail below.

g. Recombinant Production of Polypeptides According to the Invention

The invention further relates to methods for recombinant production of polypeptides according to the invention or functional, biologically active fragments thereof, wherein a polypeptide-producing microorganism is cultured, optionally the expression of the polypeptides is induced by applying at least one inducer inducing gene expression and the expressed polypeptides are isolated from the culture. The polypeptides can also be produced in this way on an industrial scale, if desired.

The microorganisms produced according to the invention can be cultured continuously or discontinuously in the batch method or in the fed-batch method or repeated fed-batch method. A summary of known cultivation methods can be found in the textbook by Chmiel (Bioprozesstechnik 1. Einführung in die Bioverfahrenstechnik [Bioprocess technology 1. Introduction to bioprocess technology] (Gustav Fischer Verlag, Stuttgart, 1991)) or in the textbook by Storhas (Bioreaktoren and periphere Einrichtungen [Bioreactors and peripheral equipment] (Vieweg Verlag, Braunschweig/Wiesbaden, 1994)).

The culture medium to be used must suitably meet the requirements of the respective strains. Descriptions of culture media for various microorganisms are given in the manual "Manual of Methods for General Bacteriology" of the American Society for Bacteriology (Washington D. C., USA, 1981).

These media usable according to the invention usually comprise one or more carbon sources, nitrogen sources, inorganic salts, vitamins and/or trace elements.

Preferred carbon sources are sugars, such as mono-, di- or polysaccharides. Very good carbon sources are for example glucose, fructose, mannose, galactose, ribose, sorbose, ribulose, lactose, maltose, sucrose, raffinose, starch or cellulose. Sugars can also be added to the media via complex compounds, such as molasses, or other by-products of sugar refining. It can also be advantageous to add mixtures of different carbon sources. Other possible carbon sources are oils and fats, for example soybean oil, sunflower oil, peanut oil and coconut oil, fatty acids, for example palmitic acid, stearic acid or linoleic acid, alcohols, for example glycerol, methanol or ethanol and organic acids, for example acetic acid or lactic acid.

Nitrogen sources are usually organic or inorganic nitrogen compounds or materials that contain these compounds. Examples of nitrogen sources comprise ammonia gas or ammonium salts, such as ammonium sulfate, ammonium chloride, ammonium phosphate, ammonium carbonate or ammonium nitrate, nitrates, urea, amino acids or complex nitrogen sources, such as corn-steep liquor, soya flour, soya protein, yeast extract, meat extract and others. The nitrogen sources can be used alone or as a mixture.

Inorganic salt compounds that can be present in the media comprise the chloride, phosphorus or sulfate salts of calcium, magnesium, sodium, cobalt, molybdenum, potassium, manganese, zinc, copper and iron.

Inorganic sulfur-containing compounds, for example sulfates, sulfites, dithionites, tetrathionates, thiosulfates, sulfides, as well as organic sulfur compounds, such as mercaptans and thiols, can be used as the sulfur source.

Phosphoric acid, potassium dihydrogen phosphate or dipotassium hydrogen phosphate or the corresponding sodium-containing salts can be used as the phosphorus source.

Chelating agents can be added to the medium, in order to keep the metal ions in solution. Especially suitable chelating agents comprise dihydroxyphenols, such as catechol or protocatechuate, or organic acids, such as citric acid.

The fermentation media used according to the invention usually also contain other growth factors, such as vitamins or growth promoters, which include for example biotin, riboflavin, thiamine, folic acid, nicotinic acid, pantothenate and pyridoxine. Growth factors and salts often originate from the components of complex media, such as yeast extract, molasses, corn-steep liquor and the like. Moreover, suitable precursors can be added to the culture medium. The exact composition of the compounds in the medium is strongly dependent on the respective experiment and is decided for each specific case individually. Information on media optimization can be found in the textbook "Applied Microbiol. Physiology, A Practical Approach" (Ed. P. M. Rhodes, P. F. Stanbury, IRL Press (1997) p. 53-73, ISBN 0 19 963577 3). Growth media can also be obtained from commercial suppliers, such as Standard 1 (Merck) or BHI (brain heart infusion, DIFCO) and the like.

All components of the medium are sterilized, either by heat (20 min at 1.5 bar and 121° C.) or by sterile filtration. The components can either be sterilized together, or separately if necessary. All components of the medium can be present at the start of culture or can be added either continuously or batchwise.

The culture temperature is normally between 15° C. and 45° C., preferably 25° C. to 40° C. and can be varied or kept constant during the experiment. The pH of the medium should be in the range from 5 to 8.5, preferably around 7.0. The pH for growing can be controlled during growing by adding basic compounds such as sodium hydroxide, potassium hydroxide, ammonia or ammonia water or acid compounds such as phosphoric acid or sulfuric acid. Antifoaming agents, for example fatty acid polyglycol esters, can be used for controlling foaming. To maintain the stability of plasmids, suitable selective substances, for example antibiotics, can be added to the medium. To maintain aerobic conditions, oxygen or oxygen-containing gas mixtures, for example ambient air, are fed into the culture. The temperature of the culture is normally in the range from 20° C. to 45° C. The culture is continued until a maximum of the desired product has formed. This target is normally reached within 10 hours to 160 hours.

The fermentation broth is then processed further. Depending on requirements, the biomass can be removed from the fermentation broth completely or partially by separation techniques, for example centrifugation, filtration, decanting or a combination of these methods or can be left in it completely.

If the polypeptides are not secreted in the culture medium, the cells can also be lysed and the product can be obtained from the lysate by known methods for isolation of proteins. The cells can optionally be disrupted with high-frequency ultrasound, high pressure, for example in a French press, by osmolysis, by the action of detergents, lytic enzymes or organic solvents, by means of homogenizers or by a combination of several of the aforementioned methods.

The polypeptides can be purified by known chromatographic techniques, such as molecular sieve chromatography (gel filtration), such as Q-sepharose chromatography, ion exchange chromatography and hydrophobic chromatography, and with other usual techniques such as ultrafiltration, crystallization, salting-out, dialysis and native gel electrophoresis. Suitable methods are described for example in Cooper, T. G., Biochemische Arbeitsmethoden [Biochemical processes], Verlag Walter de Gruyter, Berlin, N.Y. or in Scopes, R., Protein Purification, Springer Verlag, New York, Heidelberg, Berlin.

For isolating the recombinant protein, it can be advantageous to use vector systems or oligonucleotides, which lengthen the cDNA by defined nucleotide sequences and therefore code for altered polypeptides or fusion proteins, which for example serve for easier purification. Suitable modifications of this type are for example so-called "tags" functioning as anchors, for example the modification known as hexa-histidine anchor or epitopes that can be recognized as antigens of antibodies (described for example in Harlow, E. and Lane, D., 1988, Antibodies: A Laboratory Manual. Cold Spring Harbor (N.Y.) Press). These anchors can serve for attaching the proteins to a solid carrier, for example a polymer matrix, which can for example be used as packing in a chromatography column, or can be used on a microtiter plate or on some other carrier.

At the same time these anchors can also be used for recognition of the proteins. For recognition of the proteins, it is moreover also possible to use usual markers, such as fluorescent dyes, enzyme markers, which form a detectable reaction product after reaction with a substrate, or radioactive markers, alone or in combination with the anchors for derivatization of the proteins.

h. Polypeptide Immobilization

The enzymes or polypeptides according to the invention can be used free or immobilized in the method described herein. An immobilized enzyme is an enzyme that is fixed to an inert carrier. Suitable carrier materials and the enzymes immobilized thereon are known from EP-A-1149849, EP-A-1 069 183 and DE-OS 100193773 and from the references cited therein. Reference is made in this respect to the disclosure of these documents in their entirety. Suitable carrier materials include for example clays, clay minerals, such as kaolinite, diatomaceous earth, perlite, silica, aluminum oxide, sodium carbonate, calcium carbonate, cellulose powder, anion exchanger materials, synthetic polymers, such as polystyrene, acrylic resins, phenol formaldehyde resins, polyurethanes and polyolefins, such as polyethylene and polypropylene. For making the supported enzymes, the carrier materials are usually employed in a finely-divided, particulate form, porous forms being preferred. The particle size of the carrier material is usually not more than 5 mm, in particular not more than 2 mm (particle-size distribution curve). Similarly, when using dehydrogenase as whole-cell catalyst, a free or immobilized form can be selected. Carrier materials are e.g. Ca-alginate, and carrageenan. Enzymes as well as cells can also be crosslinked directly with glutaraldehyde (cross-linking to CLEAs). Corresponding and other immobilization techniques are described for example in J. Lalonde and A. Margolin "Immobilization of Enzymes" in K. Drauz and H. Waldmann, Enzyme Catalysis in Organic Synthesis 2002, Vol. III, 991-1032, Wiley-VCH, Weinheim. Further information on biotransformations and bioreactors for carrying out methods according to the invention are also given for example in Rehm et al. (Ed.) Biotechnology, 2nd Edn, Vol 3, Chapter 17, VCH, Weinheim.

i. Reaction Conditions for Biocatalytic Production Methods of the Invention

The reaction of the present invention may be performed under in vivo or in vitro conditions.

The at least one polypeptide/enzyme which is present during a method of the invention or an individual step of a multistep-method as defined herein above, can be present in living cells naturally or recombinantly producing the enzyme or enzymes, in harvested cells. i.e. under in vivo conditions, or, in dead cells, in permeabilized cells, in crude cell extracts, in purified extracts, or in essentially pure or completely pure form, i.e. under in vitro conditions. The at least one enzyme may be present in solution or as an enzyme immobilized on a carrier. One or several enzymes may simultaneously be present in soluble and/or immobilised form.

The methods according to the invention can be performed in common reactors, which are known to those skilled in the art, and in different ranges of scale, e.g. from a laboratory scale (few millilitres to dozens of litres of reaction volume) to an industrial scale (several litres to thousands of cubic meters of reaction volume). If the polypeptide is used in a form encapsulated by non-living, optionally permeabilized cells, in the form of a more or less purified cell extract or in purified form, a chemical reactor can be used. The chemical reactor usually allows controlling the amount of the at least one enzyme, the amount of the at least one substrate, the pH, the temperature and the circulation of the reaction medium. When the at least one polypeptide/enzyme is present in living cells, the process will be a fermentation. In this case the biocatalytic production will take place in a bioreactor (fermenter), where parameters necessary for suitable living conditions for the living cells (e.g. culture medium with nutrients, temperature, aeration, presence or absence of oxygen or other gases, antibiotics, and the like) can be controlled. Those skilled in the art are familiar with chemical reactors or bioreactors, e.g. with procedures for up-scaling chemical or biotechnological methods from laboratory scale to industrial scale, or for optimizing process parameters, which are also extensively described in the literature (for biotechnological methods see e.g. Crueger and Crueger, Biotechnologie—Lehrbuch der angewandten Mikrobiologie, 2. Ed., R. Oldenbourg Verlag, München, Wien, 1984).

Cells containing the at least one enzyme can be permeabilized by physical or mechanical means, such as ultrasound or radiofrequency pulses, French presses, or chemical means, such as hypotonic media, lytic enzymes and detergents present in the medium, or combination of such methods. Examples for detergents are digitonin, n-dodecylmaltoside, octylglycoside, Triton® X-100, Tween® 20, deoxycholate, CHAPS (3-[(3-Cholamidopropyl)dimethylammonio]-1-propansulfonate), Nonidet® P40 (Ethylphenolpoly(ethyleneglycolether), and the like.

Instead of living cells biomass of non-living cells containing the required biocatalyst(s) may be applied of the biotransformation reactions of the invention as well.

If the at least one enzyme is immobilised, it is attached to an inert carrier as described above.

The conversion reaction can be carried out batch wise, semi-batch wise or continuously. Reactants (and optionally nutrients) can be supplied at the start of reaction or can be supplied subsequently, either semi-continuously or continuously.

The reaction of the invention, depending on the particular reaction type, may be performed in an aqueous, aqueous-organic or non-aqueous reaction medium.

An aqueous or aqueous-organic medium may contain a suitable buffer in order to adjust the pH to a value in the range of 5 to 11, like 6 to 10.

In an aqueous-organic medium an organic solvent miscible, partly miscible or immiscible with water may be applied. Non-limiting examples of suitable organic solvents are listed below. Further examples are mono- or polyhydric, aromatic or aliphatic alcohols, in particular polyhydric aliphatic alcohols like glycerol.

The non-aqueous medium may contain is substantially free of water, i.e. will contain less that about 1 wt.-% or 0.5 wt.-% of water.

Biocatalytic methods may also be performed in an organic non-aqueous medium. As suitable organic solvents there may be mentioned aliphatic hydrocarbons having for example 5 to 8 carbon atoms, like pentane, cyclopentane, hexane, cyclohexane, heptane, octane or cyclooctane; aromatic carbohydrates, like benzene, toluene, xylenes, chlorobenzene or dichlorobenzene, aliphatic acyclic and ethers, like diethylether, methyl-tert.-butylether, ethyl-tert.-butyleether, dipropylether, diisopropylether, dibutylether; or mixtures thereof.

The concentration of the reactants/substrates may be adapted to the optimum reaction conditions, which may depend on the specific enzyme applied. For example, the initial substrate concentration may be in the 0.1 to 0.5 M, as for example 10 to 100 mM.

The reaction temperature may be adapted to the optimum reaction conditions, which may depend on the specific enzyme applied. For example, the reaction may be performed at a temperature in a range of from 0 to 70° C., as for example 20 to 50 or 25 to 40° C. Examples for reaction temperatures are about 30° C., about 35° C., about 37° C., about 40° C., about 45° C., about 50° C., about 55° C. and about 60° C.

The process may proceed until equilibrium between the substrate and then product(s) is achieved, but may be stopped earlier. Usual process times are in the range from 1 minute to 25 hours, in particular 10 min to 6 hours, as for example in the range from 1 hour to 4 hours, in particular 1.5 hours to 3.5 hours. These parameters are non-limiting examples of suitable process conditions.

If the host is a transgenic plant, optimal growth conditions can be provided, such as optimal light, water and nutrient conditions, for example.

k. Product Isolation

The methodology of the present invention can further include a step of recovering an end or intermediate product, optionally in stereoisomerically or enantiomerically substantially pure form. The term "recovering" includes extracting, harvesting, isolating or purifying the compound from culture or reaction media. Recovering the compound can be performed according to any conventional isolation or purification methodology known in the art including, but not limited to, treatment with a conventional resin (e.g., anion or cation exchange resin, non-ionic adsorption resin, etc.), treatment with a conventional adsorbent (e.g., activated charcoal, silicic acid, silica gel, cellulose, alumina, etc.), alteration of pH, solvent extraction (e.g., with a conventional solvent such as an alcohol, ethyl acetate, hexane and the like), distillation, dialysis, filtration, concentration, crystallization, recrystallization, pH adjustment, lyophilization and the like.

Identity and purity of the isolated product may be determined by known techniques, like High Performance Liquid Chromatography (HPLC), gas chromatography (GC), Spektroskopy (like IR, UV, NMR), Colouring methods, TLC, NIRS, enzymatic or microbial assays. (see for example: Patek et al. (1994) Appl. Environ. Microbiol. 60:133-140; Malakhova et al. (1996) Biotekhnologiya 11 27-32; und Schmidt et al. (1998) Bioprocess Engineer. 19:67-70. Ullmann's Encyclopedia of Industrial Chemistry (1996) Bd. A27, VCH: Weinheim, S. 89-90, S. 521-540, S. 540-547, S. 559-566, 575-581 und S. 581-587; Michal, G (1999) Biochemical Pathways: An Atlas of Biochemistry and Molecular Biology, John Wiley and Sons; Fallon, A. et al. (1987) Applications of HPLC in Biochemistry in: Laboratory Techniques in Biochemistry and Molecular Biology, Bd. 17.)

The cyclic terpene compound produced in any of the method described herein can be converted to derivatives such as, but not limited to hydrocarbons, esters, amides, glycosides, ethers, epoxides, aldehydes, ketons, alcohols, diols, acetals or ketals. The terpene compound derivatives can be obtained by a chemical method such as, but not limited to oxidation, reduction, alkylation, acylation and/or rearrangement. Alternatively, the terpene compound derivatives can be obtained using a biochemical method by contacting the terpene compound with an enzyme such as, but not limited to an oxidoreductase, a monooxygenase, a dioxygenase, a transferase. The biochemical conversion can be performed in-vitro using isolated enzymes, enzymes from lysed cells or in-vivo using whole cells or organisms.

l. Fermentative Production of Albicanyl Diphosphate and/or Albicanol

The invention also relates to methods for the fermentative production of albicanyl diphosphate and/or albicanol.

A fermentation as used according to the present invention can, for example, be performed in stirred fermenters, bubble columns and loop reactors. A comprehensive overview of the possible method types including stirrer types and geometric designs can be found in "Chmiel: Bioprozesstechnik: Einfuhrung in die Bioverfahrenstechnik, Band 1". In the process of the invention, typical variants available are the following variants known to those skilled in the art or explained, for example, in "Chmiel, Hammes and Bailey: Biochemical Engineering", such as batch, fed-batch, repeated fed-batch or else continuous fermentation with and without recycling of the biomass. Depending on the production strain, sparging with air, oxygen, carbon dioxide, hydrogen, nitrogen or appropriate gas mixtures may be effected in order to achieve good yield (YP/S).

The culture medium that is to be used must satisfy the requirements of the particular strains in an appropriate manner. Descriptions of culture media for various microorganisms are given in the handbook "Manual of Methods for General Bacteriology" of the American Society for Bacteriology (Washington D. C., USA, 1981).

These media that can be used according to the invention may comprise one or more sources of carbon, sources of nitrogen, inorganic salts, vitamins and/or trace elements.

Preferred sources of carbon are sugars, such as mono-, di- or polysaccharides. Very good sources of carbon are for example glucose, fructose, mannose, galactose, ribose, sorbose, ribulose, lactose, maltose, sucrose, raffinose, starch or cellulose. Sugars can also be added to the media via complex compounds, such as molasses, or other by-products from sugar refining. It may also be advantageous to add mixtures of various sources of carbon. Other possible sources of carbon are oils and fats such as soybean oil, sunflower oil, peanut oil and coconut oil, fatty acids such as palmitic acid, stearic acid or linoleic acid, alcohols such as glycerol, methanol or ethanol and organic acids such as acetic acid or lactic acid.

Sources of nitrogen are usually organic or inorganic nitrogen compounds or materials containing these compounds. Examples of sources of nitrogen include ammonia gas or ammonium salts, such as ammonium sulfate, ammonium chloride, ammonium phosphate, ammonium carbonate or ammonium nitrate, nitrates, urea, amino acids or complex sources of nitrogen, such as corn-steep liquor, soybean flour, soy-bean protein, yeast extract, meat extract and others. The sources of nitrogen can be used separately or as a mixture.

Inorganic salt compounds that may be present in the media comprise the chloride, phosphate or sulfate salts of calcium, magnesium, sodium, cobalt, molybdenum, potassium, manganese, zinc, copper and iron.

Inorganic sulfur-containing compounds, for example sulfates, sulfites, di-thionites, tetrathionates, thiosulfates, sulfides, but also organic sulfur compounds, such as mercaptans and thiols, can be used as sources of sulfur.

Phosphoric acid, potassium dihydrogenphosphate or dipotassium hydrogenphosphate or the corresponding sodium-containing salts can be used as sources of phosphorus.

Chelating agents can be added to the medium, in order to keep the metal ions in solution. Especially suitable chelating agents comprise dihydroxyphenols, such as catechol or protocatechuate, or organic acids, such as citric acid.

The fermentation media used according to the invention may also contain other growth factors, such as vitamins or growth promoters, which include for example biotin, riboflavin, thiamine, folic acid, nicotinic acid, pantothenate and pyridoxine. Growth factors and salts often come from complex components of the media, such as yeast extract, molasses, corn-steep liquor and the like. In addition, suitable precursors can be added to the culture medium. The precise composition of the compounds in the medium is strongly dependent on the particular experiment and must be decided individually for each specific case. Information on media optimization can be found in the textbook "Applied Microbiol. Physiology, A Practical Approach" (1997) Growing media can also be obtained from commercial suppliers, such as Standard 1 (Merck) or BHI (Brain heart infusion, DIFCO) etc.

All components of the medium are sterilized, either by heating (20 min at 1.5 bar and 121° C.) or by sterile filtration. The components can be sterilized either together, or if necessary separately. All the components of the medium can be present at the start of growing, or optionally can be added continuously or by batch feed.

The temperature of the culture is normally between 15° C. and 45° C., preferably 25° C. to 40° C. and can be kept constant or can be varied during the experiment. The pH value of the medium should be in the range from 5 to 8.5, preferably around 7.0. The pH value for growing can be controlled during growing by adding basic compounds such as sodium hydroxide, potassium hydroxide, ammonia or ammonia water or acid compounds such as phosphoric acid or sulfuric acid. Antifoaming agents, e.g. fatty acid polyglycol esters, can be used for controlling foaming. To maintain the stability of plasmids, suitable substances with selective action, e.g. antibiotics, can be added to the medium. Oxygen or oxygen-containing gas mixtures, e.g. the ambient air, are fed into the culture in order to maintain aerobic conditions. The temperature of the culture is normally from 20° C. to 45° C. Culture is continued until a maximum of the desired product has formed. This is normally achieved within 1 hour to 160 hours.

The methodology of the present invention can further include a step of recovering albicanyl diphosphate and/or albicanol The term "recovering" includes extracting, harvesting, isolating or purifying the compound from culture media. Recovering the compound can be performed according to any conventional isolation or purification methodology known in the art including, but not limited to, treatment with a conventional resin (e.g., anion or cation exchange resin, non-ionic adsorption resin, etc.), treatment with a conventional adsorbent (e.g., activated charcoal, silicic acid, silica gel, cellulose, alumina, etc.), alteration of pH, solvent extraction (e.g., with a conventional solvent such as an alcohol, ethyl acetate, hexane and the like), distillation, dialysis, filtration, concentration, crystallization, recrystallization, pH adjustment, lyophilization and the like.

Before the intended isolation the biomass of the broth can be removed. Processes for removing the biomass are known to those skilled in the art, for example filtration, sedimentation and flotation. Consequently, the biomass can be removed, for example, with centrifuges, separators, decanters, filters or in flotation apparatus. For maximum recovery of the product of value, washing of the biomass is often advisable, for example in the form of a diafiltration. The selection of the method is dependent upon the biomass content in the fermenter broth and the properties of the biomass, and also the interaction of the biomass with the product of value.

In one embodiment, the fermentation broth can be sterilized or pasteurized. In a further embodiment, the fermentation broth is concentrated. Depending on the requirement, this concentration can be done batch wise or continuously. The pressure and temperature range should be selected such that firstly no product damage occurs, and secondly minimal use of apparatus and energy is necessary. The skillful selection of pressure and temperature levels for a multistage evaporation in particular enables saving of energy.

The following examples are illustrative only and are not intended to limit the scope of the claims an embodiments described herein.

The numerous possible variations that will become immediately evident to a person skilled in the art after heaving considered the disclosure provided herein also fall within the scope of the invention.

EXPERIMENTAL PART

The invention will now be described in further detail by way of the following Examples.
Materials:
Unless otherwise stated, all chemical and biochemical materials and microorganisms or cells employed herein are commercially available products.

Unless otherwise specified, recombinant proteins are cloned and expressed by standard methods, such as, for example, as described by Sambrook, J., Fritsch, E. F. and Maniatis, T., Molecular cloning: A Laboratory Manual, $2^{nd}$ Edition, Cold Spring Harbor Laboratory, Cold Spring Harbor Laboratory Press, Cold Spring Harbor, N.Y., 1989.
Methods:
Standard Assay for Determining Albicanyl Diphosphate Synthase Activity (In Vitro)
Suitable methods are described in Example 5 and Example 7 below.
Gas Chromatography Mass Spectrometry (GC-MS)
Agilent 6890 series GC system equipped with a DB1-ms column 30 m×0.25 mm×0.25 µm film thickness (P/N 122-0132, J&W scientific Inc., Folsom, Calif.) and coupled with a 5975 series mass spectrometer was used. The carrier gas was helium at a constant flow of 0.7 mL/min. Injection was in split (1:25) mode with the injector temperature set at 250° C. The oven temperature was programmed from 50° C. (5 min hold) to 300° C. at 5° C./min, then to 340° C. at 50° C./min and held for 3 min.

Example 1

Sourcing of Plant Material and Leaf Transcriptome Sequencing.

Figure 3:
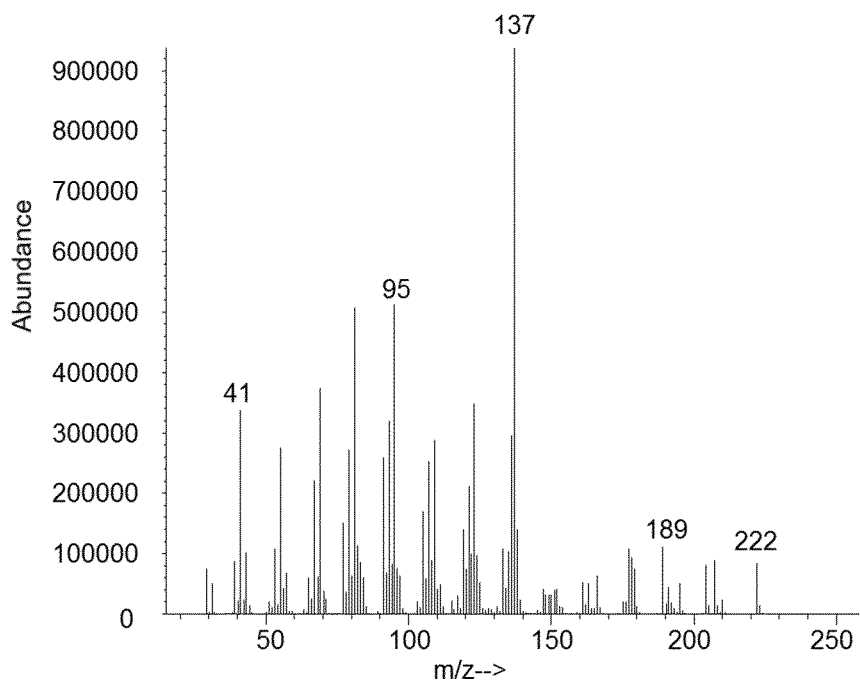
FIG. 3: Mass spectrum of the albicanol peak in FIG. 2.

Plant materials from *Dryopteris* were collected from Northern China. To establish whether *Dryopteris fragrans* contained albicanol, its fresh leaves were extracted with dichloromethane for chemical analysis. The extracts were analysed by GC/MS with the parameters as stated above. Identification of products was based on mass spectra and retention indices (FIGS. 2 and 3).

Fresh leaves of *Dryopteris fragrans* with sample IDs of PNLI20141074 and YGY-15-2706 were both used for transcriptome analysis. Total RNA of *Dryopteris fragrans* was extracted using the RNeasy Plant Mini Kit (50) 74904 from QIAGEN.

The total RNA sample PNLI20141074 was processed using the NEBNext® Ultra™ RNA Library Prep Kit for Illumina (NEB, USA) and TruSeq PE Cluster Kit (Illumina, USA) and then sequenced on Illumina Miseq sequencer. An amount of 20.88 million of paired-end reads of 2×350 bp was generated. The reads were assembled using the Trinity (http://trinityrnaseq.sfnet/) software and 85753 contigs with an N50 of 1373 were obtained. The contigs were analysed by EMBOSS software (http://emboss.sourceforge.net/) to get protein sequences. The sequence of AstC from prior art [Y. Shinohara, S. Takahashi, H. Osada & Y. Koyama (2016) Identification of a novel sesquiterpene biosynthetic machinery involved in astellolide biosynthesis. Sci. Rep. 6:32865 (DOI: 10.1038/srep32865).] was used for searching the potential albicanol synthase in the protein sequences data of *Dryopteris fragrans*. This approach provided DfHAD, a 5' sequence of a non-typical haloacid-dehalogenase-like hydrolase, highly expressed in the transcriptome as analysed by CLC genomics workbench.

In addition to PNLI20141074, the total RNA sample YGY-15-2706 was processed using the PacBio® SMRT-bell™Template Prep Kit (PacBio, USA) and PacBio®DNA/Polymerase Kit (PacBio, USA) and then sequenced on PacBio RS II sequencer. An amount of 0.96 million of a mean length of 2302 bp was generated. The reads were analysed by Smrtanalysis (v_2.3.0) (http://www.pacb.com) and 24848 contigs with an N50 of 1448 were obtained, which contains the 3' sequence of DfHAD. By combining these 2 approaches, the full putative length of DfHAD was assembled and used for gene cloning.

The total RNA samples of YGY-15-2706 were first reverse transcribed into cDNA using SMARTer™ RACE cDNA Amplification Kit (Clontech). The products were then used as the template for gene cloning. Both DfHAD and its variants, DfHAD-8(K532R) and DfHAD-9(V274A), were amplified from the cDNA by using forward primer (5'-ATGGAGTTCTCTGCCTCTG-3') (SEQ ID NO: 15) and reverse primer (5'-GGTTTGGCTTATGGAAGGT-3') (SEQ ID NO: 16). The enzymatic activity of the DfHAD and DfHAD-8(K532R) and DfHAD-9(V274A) were evaluated as described in example 2 and 3.

Example 2

Functional Expression and Characterization of DfHAD in an *E. coli* Expression System.

The sequences of DfHAD and its variants, DfHAD-8 (K532R) and DfHAD-9(V274A), were optimized by following the Genscript genetic codon frequency for *Escherichia coli*. They were then synthesized in vitro and subcloned into the pETDuet-1 plasmid (Novagen) or the pJ401 plasmid (DNA 2.0) for subsequent expression in *E. coli*.

BL21(DE3) *E. coli* cells (Tiangen) were co-transformed with the plasmid pACYC-29258-4506, containing the genes encoding for a heterologous mevalonate pathway, and the plasmid pETDuet-DfHAD or pETDuet-DfHAD-8(K532R) or pETDuet-DfHAD-9(V274A), respectively. To increase the productivity of the cells, a heterologous FPP synthase and the enzymes from a complete heterologous mevalonate (MVA) pathway were also expressed in the same cells. The construction of the expression plasmid containing an FPP synthase gene and the gene for a complete MVA pathway was described in WO2013064411 or in M. Schalk, L. Pastore, M. A. Mirata, S. Khim, M. Schouwey, F. Deguerry, V. Pineda, L. Rocci & L. Daviet (2012) Toward a biosynthetic route to sclareol and amber odorants. J. Am. Chem. Soc. 134, 18900-3 (DOI: 10.1021/ja307404u). Briefly, an expression plasmid was prepared containing two operons composed of the genes encoding the enzymes for a complete mevalonate pathway. A first synthetic operon consisting of an *E. coli* acetoacetyl-CoA thiolase (atoB), a *Staphylococcus aureus* HMG-CoA synthase (mvaS), a *Staphylococcus aureus* HMG-CoA reductase (mvaA) and a *Saccharomyces cerevisiae* FPP synthase (ERG20) genes was synthetized in vitro (DNA2.0, Menlo Park, Calif., USA) and ligated into the NcoI-BamHI digested pACYCDuet-1 vector (Invitrogen) yielding pACYC-29258. A second operon containing a mevalonate kinase (MvaK1), a phosphomevalonate kinase (MvaK2), a mevalonate diphosphate decarboxylase (MvaD), and an isopentenyl diphosphate isomerase (idi) was amplified from genomic DNA of *Streptococcus pneumoniae* (ATCC BAA-334) and ligated into the second multicloning site of pACYC-29258 providing the plasmid pACYC- 29258-4506. This plasmid thus contains the genes encoding all enzymes of the biosynthetic pathway leading from acetyl-coenzyme A to FPP.

BL21(DE3) *E. coli* cells (Tiangen) were co-transformed with the plasmid pACYC/ScMVA, containing the genes encoding for a heterologous mevalonate pathway, and the plasmid pETDuet-DfHAD or pETDuet-DfHAD-8(K532R) or pETDuet-DfHAD-9(V274A), respectively. To construct the pACYC/ScMVA plasmid, we divided the eight biosynthetic genes into 2 synthetic operons referred as the 'upper' and 'lower' mevalonate (MVA) pathway. As an upper MVA pathway, we created a synthetic operon consisting of an acetoacetyl-CoA thiolase from *E. coli* encoded by atoB, a HMG-CoA synthase and a truncated version of HMG-CoA reductase from *Saccharomyces cerevisiae* encoded by ERG13 and ERG19, respectively. This operon transforms the primary metabolite Acetyl-CoA into (R)-mevalonate. As a 'lower' mevalonate pathway, we created a second synthetic operon encoding a mevalonate kinase (ERG12, *S. cerevisiae*), a phosphomevalonate kinase (ERGS, *S. cerevisiae*), a phosphomevalonate decarboxylase (MVD1, *S. cerevisiae*), an isopentenyl diphosphate isomerase (idi, *E. coli*) and a farnesyl pyrophosphate (FPP) synthase (IspA, *E. coli*). Finally, a second FPP synthase from *S. cerevisiae* (ERG20) was introduced into the upper pathway operon to improve the conversion of the isoprenoid C5 units (IPP and DMAPP) into farnesyl pyrophosphate (FPP). Each operon was subcloned into one of the multiple-cloning sites of a low-copy expression plasmid under the control of a bacteriophage T7 promoter (pACYCDuet-1, Invitrogen) providing the plasmid pACYC/ScMVA. This plasmid thus contains the genes encoding all enzymes of the biosynthetic pathway leading from acetyl-coenzyme A to FPP.

Figure 4:
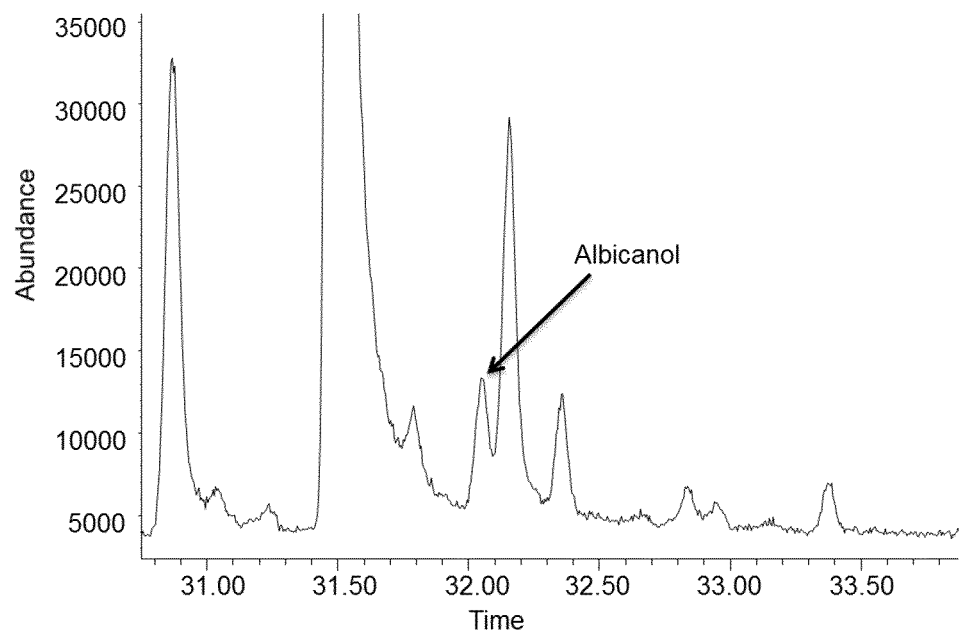
FIG. 4: GC/MS chromatogram of an extract of an *E. coli* (expressing DfHAD) broth (only the zone for sesquiterpenes is displayed). The arrow denotes the albicanol peak.
Figure 5:
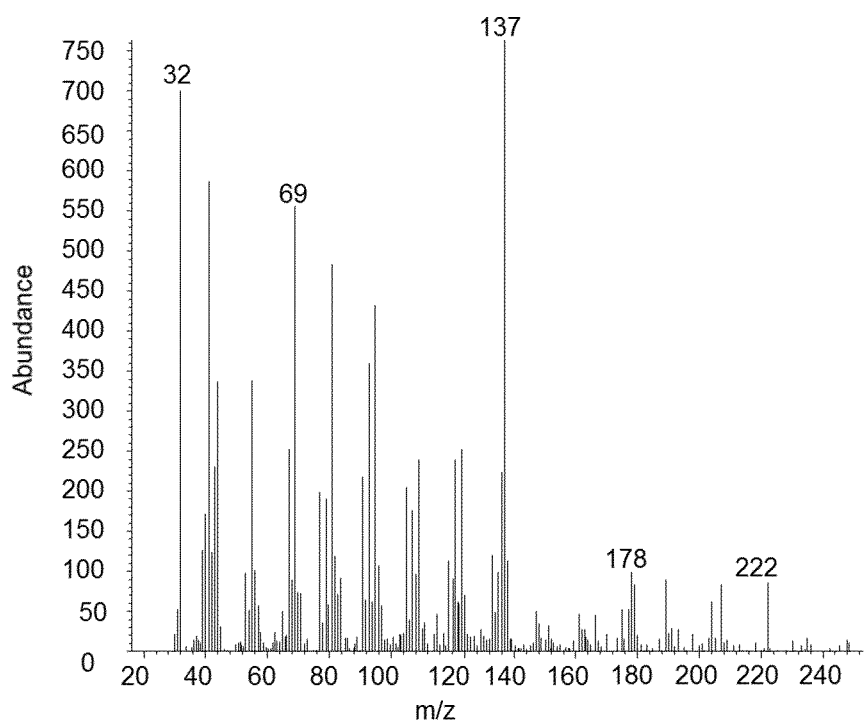
FIG. 5. Mass spectrum of the peak of albicanol in FIG. 4.

The co-transformed cells were selected on LB-agar plates containing kanamycin (50 µg/mL final) or Ampicillin (50 µg/mL final) as appropriate and chloramphenicol (34 µg/mL final). Single colonies were used to inoculate 5 mL liquid LB medium supplemented with the same antibiotics. Cultures were incubated overnight at 37° C. with shaking at 200 rpm. The next day, 2 mL of TB medium supplemented with the same antibiotics and glycerol (3% w/v final) were inoculated with 0.2 mL of the overnight culture. After 5 hours of incubation at 37° C. and shaking at 200 rpm, the culture was cooled down to 25° C., shaken a further 1 hour at 200 rpm, then IPTG (0.1 mM final) was added to each tube, overlayed with 200 µl of decane. The cultures were incubated for a further 48 hours at 25° C. at 200 rpm. The cultures were then extracted twice with 1 volume of ethyl acetate. 50 µl of isolongifolene at 2 mg/mL was added to the organic phase as internal standard before analysing the samples by GC/MS. GC/MS analysis used the same system as described in Example 1. The carrier gas was helium at a constant flow of 0.7 mL/min. Injection was in split (1:25) mode with the injector temperature set at 250° C. The oven temperature was programmed from 50° C. (5 min hold) to 300° C. at 5° C./min, then to 340° C. at 50° C./min and held for 3 min. Identification of products was based on mass spectra and retention indices. GC/MS analysis revealed that the recombinant cells expressing DfHAD, DfHAD-8(K532R) and DfHAD-9(V274A) produced albicanol as the main product with the titre ranging from 0.2 mg/L to 3 mg/L (FIGS. 4 and 5).

Example 3

Functional Expression and Characterization of DfHAD in a Transient Tobacco Expression System.

DfHAD was integrated into a modified binary vector pMTPS1 to form pMTPS1-DfHAD. pMTPS1 is an engineered vector based on the commercial plasmid pCAMBIA2300 (Cambia). The Cauliflower Mosaic Virus promoter (CaMV35S) was inserted between the EcoRI and KpnI restriction sites; the octopine synthase (OCS) terminator was inserted between the PstI and HindIII. The NPTII selection marker inside the left and the right borders of transfer DNA (T-Border) of pCAMBIA2300 was replaced by the codon-optimized *Gallus gallus* farnesyl diphosphate synthase (GgFPS) using the XhoI restriction enzyme followed by direction confirmation; a cassette of the RNA silencing suppressor P19 from Tomato bush stunt virus, controlled by Cauliflower Mosaic Virus 35S promoter and terminator, was assembled into the HindIII site to deliver pMTPS1. Finally, the codon-optimized DfHAD was inserted between SalI and PstI. The binary vector pMTPS1 was thus formed to produce the substrate farnesyl pyrophosphate (FPP) and then transform it to albicanol.

300 ng of plasmid pMTPS1-DfHAD was transformed into *Agrobacterium tumefaciens* EHA105. Transformed cells were selected on LB-agarose plates containing kanamycin (50 µg/mL) and rifampicin (25 µg/mL) that were incubated at 28° C. for 2 days. Single colonies were inoculated into 50 mL LB with the same antibiotics and incubated at 28° C. in a shaker (200 rpm speed) overnight. When the OD600 reached 1.0, the culture was centrifuged at 5000 rpm for 10 min at room temperature. The cell pellet was re-suspended with 20 mL MgSO$_4$ (10 mM). The suspension was centrifuged again and the cell pellet was re-suspended by an Acetosyringone (AS) solution (765 µM) to adjust the OD600 to 0.5. The resuspension was infiltrated into the intercellular space from the abaxial side of tobacco leaves (*Nicotiana benthamiana*). The tobacco plants had been previously grown for 4-weeks at 28° C. with 12 hour light/12 hour dark photoperiod. Three days post-infection, the infected leaves were fed with mevalonate (25 mM). After 8 hours the leaf samples were harvested and about 500-1000 mg of the leaves were weighed into 10 mL Eppendorf tubes and frozen in liquid nitrogen immediately. The samples were ground to powder and extracted overnight with 2 mL ethyl acetate containing 20 µg/ml dodecane as an internal standard. Each sample was filtered and the filtrate was dried over anhydrous Na$_2$SO$_4$ and then analysed by GC/MS. Tobacco samples were extracted with 4 ml of ethyl acetate (spiked with 3.4 ppm of dodecane). The extracts were analysed by GC/MS with the parameter as stated above. Here injection was in split (1:5) mode with the injector temperature set at 250° C.

Figure 6:
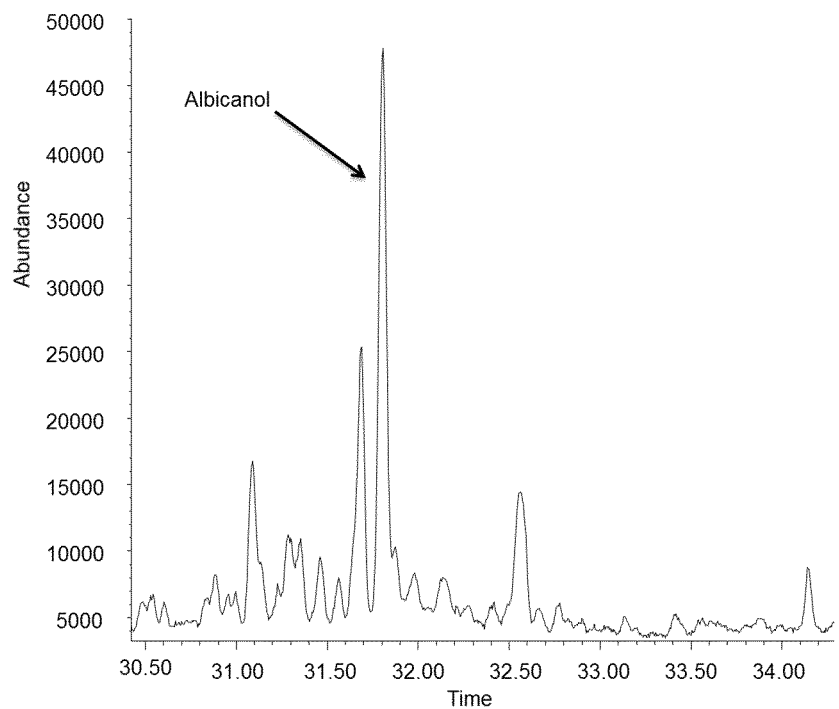
FIG. 6: GC/MS chromatogram of transfected tobacco leaves dichloromethane extract (only the zone for sesquiterpenes is displayed). The arrow denotes the peak of albicanol.
Figure 7:
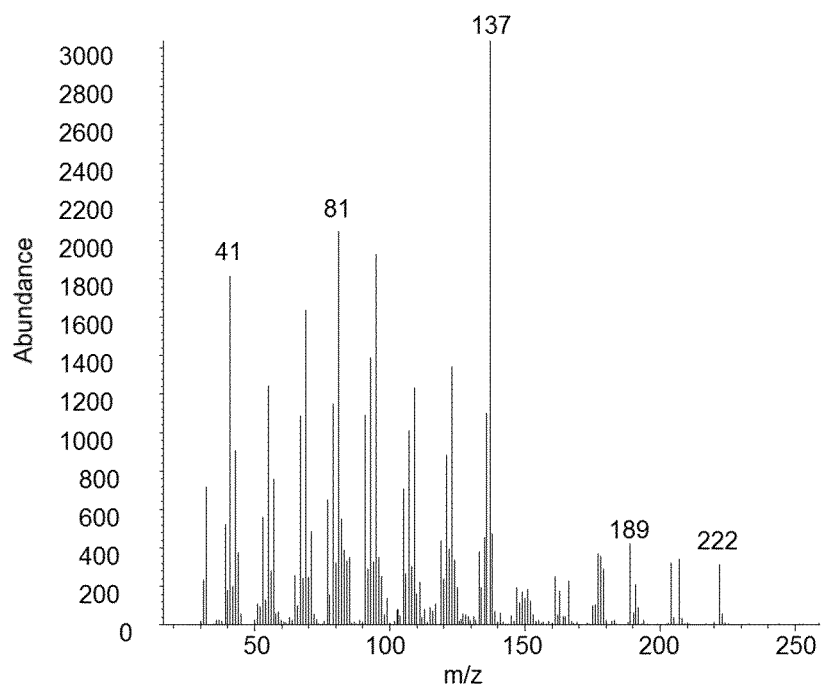
FIG. 7: Mass spectrum of the peak of albicanol in FIG. 6.

In this tobacco transient transformation experiment, infected plants expressing DfHAD produced albicanol as the main peak, based on mass spectrum and retention index in GC/MS analysis (FIGS. 6 and 7). The yield of albicanol in this experiment was calculated based on the internal standard as 3.75 µg albicanol per gram of fresh tobacco leaves.

Example 4

Functional Expression and Characterization of Mutants DfHAD in an *E. coli* Expression System.

A series of mutants of DfHAD were constructed to confirm the importance of the identified class I and class II motifs for its terpene synthase activity (see Table of FIG. 10). The corresponding genes were inserted in pJ401 and the activity assessed as described in Example 2.

The importance of the non-typical class I insertion SF and the non-typical class II motif H is highlighted in this experiment:

90% loss of activity when SF was deleted

47% loss of activity when the basic residue H was replaced with the acidic residue D 100% loss of activity when SF was deleted and H replaced by D Maybe more surprisingly, the replacement of the acidic residue E by the functional equivalent D resulted in 85% loss of activity. The double mutation D to E and E to D resulted in a 99% loss of activity.

Example 5

Characterisation of Purified DfHAD in an In Vitro System.

In order to purify DfHAD to assess its activity in vitro, its coding sequence (optimised for *E. coli* expression) was subcloned into a pGS-21a plasmid (Genscript). The expressed protein is fused with an N-terminus 6×His-GST-tag (SEQ ID NO: 18, encoded by SEQ ID NO:17) After transformation in BL21(DE3) *E. coli* cells and selection on LB-agar plates containing ampicillin (50 μg/mL final), a single colony was inoculated into 40 mL LB media supplemented with the same antibiotics and the cultures were incubated at 37° C., 180 rpm overnight. The next day, 5-10 mL of the culture was inoculated into 500 mL of 2× YT media containing ampicillin at 50 mg/L and incubated at 37° C., 150 rpm for ~3 hours (OD600=0.7–1.2). The culture was then cooled down to 25° C. for 1.5 hours and 0.25 mL of 1 M IPTG was added, then incubated at 25° C., 150 rpm for 18 hours. The culture was harvested by centrifugation at 4° C. for 15 min at 3500 g and the pellet was washed twice with chilled Buffer A (50 mM $Na_2HPO_4$, 10 mM imidazole, 500 mM NaCl, pH7.8). The pellet was resuspended in Buffer A containing proteases inhibitor (SigmaFast EDTA-free, Sigma) and the volume adjusted to 25 mL. 25 mg of Lysozyme, 25 μL DNase I, 125 μL $MgCl_2$, and 60 μL of 0.2 M PMSF were added to the suspension. After incubation on ice for 30 min followed by sonication (3 sec ON, 12 sec OFF, 3 min total, repeated once) the supernatant was harvested by centrifugation at 4° C. and 8000 g for 10 min. The protein was purified by the batch method on glutathione-agarose (Sigma G4510) according to the manufacturer protocol for GST-tagged protein. The molecular weight of the protein was estimated by SDS-PAGE and correspond to the molecular weight calculated from the amino-acid sequence of DfHAD (65 kDa) plus the GST-Tag (21 kDa), i.e. 91 kDa, by comparison with a molecular weight standard (PAGE-MASTER Plus, Genescript).

For the in vitro biochemical assay of DfHAD proteins, 1.5 μM of purified recombinant protein was added to a 2 ml reaction mixture containing 10 mM $MgCl_2$, 5 mM DTT, 29 μM FPP in a 50 mM Tris-HCl pH8.0 buffer. The samples were incubated at 30° C., 50 rpm for 2 h. The samples were then split in two and in one of them 20 μL of a bacterial alkaline phosphatase (BAP) (Sangon-B004081-100) was added and the reaction pursued for an extra 1 h at 25° C. The BAP enzyme E.C. 3.1.3.1 originates from *E. coli* and the sequence information is available under Genbank accession number M13345. A control with no protein added was also run in the same conditions. For GC/MS analysis, 10 μL of isolongifolene (internal standard) at 2 mg/mL was added into a 0.5 mL aliquot as internal standard. The reactions were then extracted with 0.25 mL ethyl acetate and GC/MS run as described previously.

Figure 8:
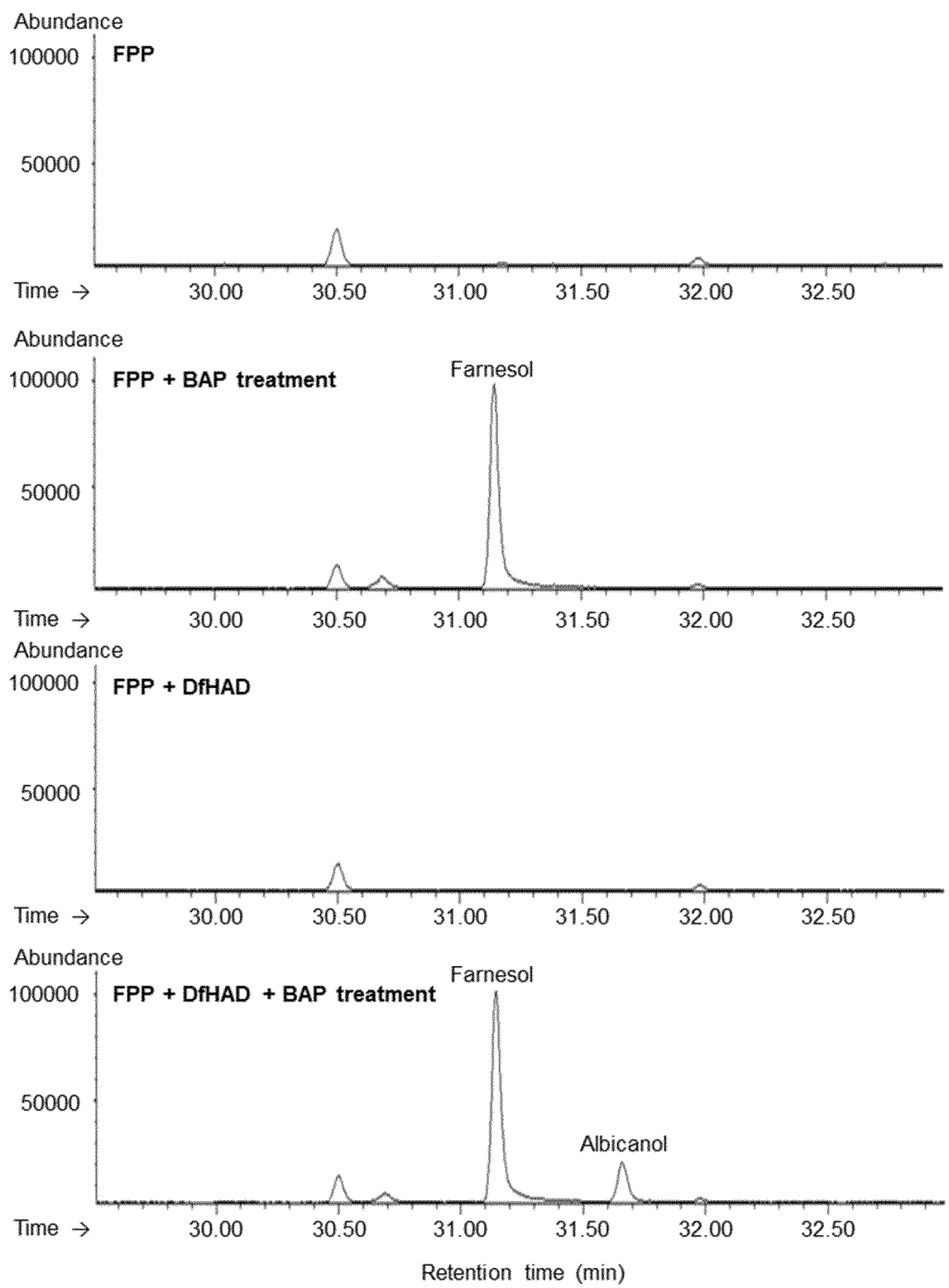
FIG. 8: GC chromatogram of samples from the in vitro biochemical assay of DfHAD
Figure 11:
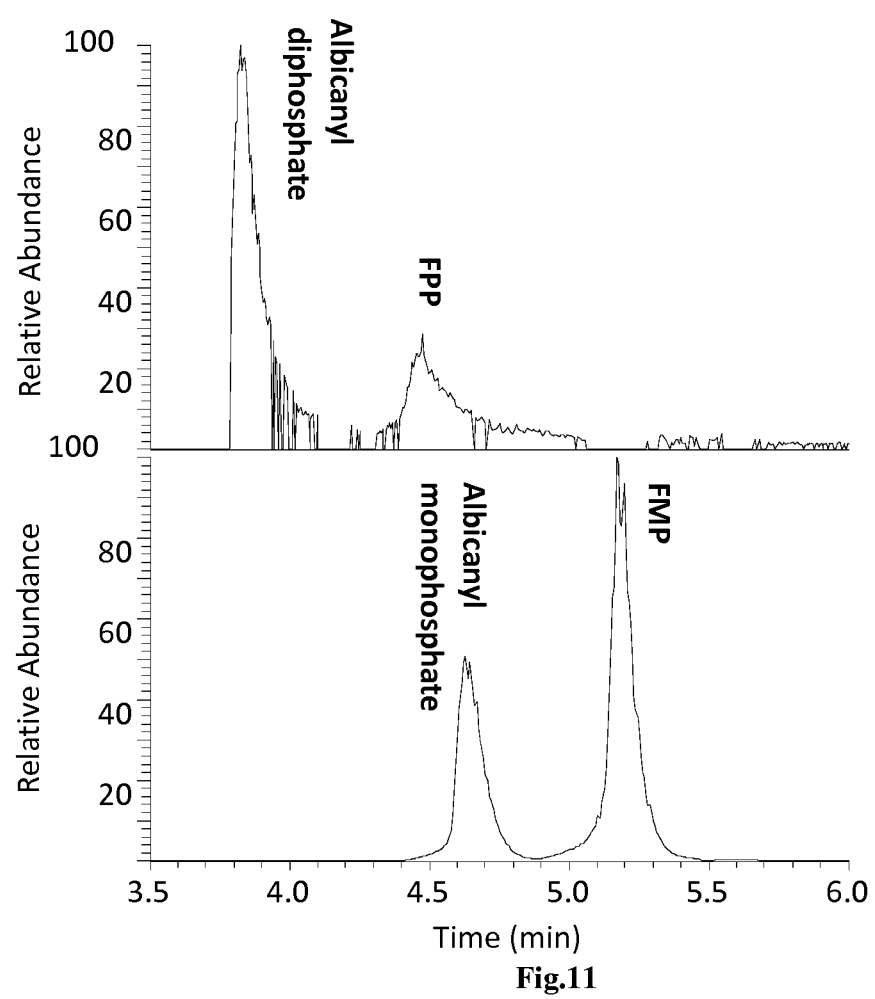
FIG. 11. Chromatogram of extracted ion 381.1237 for sesquiterpene diphosphate (upper) and monophosphate 301.1574 (lower) from the E. coli extract.

After analysis by GC-MS, as shown in FIG. 8, we could not detect any albicanol. As the previous in vivo assay was successful, and the bacterial extract contains phosphatase(s) from *E. coli*, we hypothesised that this could be due to the formation of albicanyl diphosphate by the enzyme and not albicanol, comparable to the catalytic property of AstC. We therefore conducted the same experiment in presence of a bacterial alkaline phosphatase (BAP) (FIG. 8). Indeed, the addition of such a commercial phosphatase allowed us to detect albicanol in our sample, as well as the formation of farnesol from FPP, suggesting the formation of albicanyl diphosphate through a protonation-initiated mechanism.

Example 6

Synthesis of Albicanyl Diphosphate and Monophosphate

These syntheses are based on two previous publications: Lira L M et al (2013), *Tetrahedron Lett*, 54, 1690-1692; Thulasiram H V et al (2006), *J Org Chem*, 71, 1739-1741.

Preparation of Albicanyl Diphosphate

To a solution of albicanol (64 mg, 0.288 mmol) in 2,2,2-trichloroacetonitrile (0.721 ml, 7.20 mmol) was added 0.70 mL of TEAP (bis-triethylammonium phosphate, see note 1) at room temperature. Two more additions of 0.720 mL of TEAP were carried out in 5 minutes intervals. The resulting mixture was stirred for 3 hours. It was then loaded onto a silica gel column and eluted with 150 mL of 100% ethyl acetate followed by 90 mL of Isopropanol:$NH_4OH$:$H_2O$ (6.0:2.5:0.5) mix to give fractions 1 (discarded) and 2, respectively. Fraction 2 was concentrated under reduced pressure and diluted with 10 mL of 10% MeOH/$H_2O$ mix. The resulting mixture was loaded onto a pre-conditioned (see note 2) Waters SPE: Oasis MCX 6cc (500 mg) LP Extraction cartridge, eluted with 20 mL of 10% MeOH/$H_2O$ to give fractions 1 & 2 and then with 20 mL of 50% MeOH/$H_2O$ to give fractions 3 & 4. Fractions 3 & 4 were combined and lyophilized to give albicanyl diphosphate as an off-white solid (35 mg, 0.092 mmol, 31%).

Notes:
1) TEAP was prepared by mixing 0.91 mL of solution of 2 mL of phosphoric acid in 7.82 mL acetonitrile and 1.5 mL of solution of 4.4 mL triethylamine in 4.0 mL acetonitrile (J. Org Chem, 71, 1739-1741).
2) The cartridge was first eluted with 5 mL of MeOH and then with 5 mL of $H_2O$.

Preparation of Albicanyl Monophosphate

Tetrabutylammonium phosphate monobasic (133 mg, 0.391 mmol) was added to a round bottom flask containing albicanol (87 mg, 0.391 mmol) and 2,2,2-trichloroacetonitrile (1 ml, 9.97 mmol). The resulting mixture was stirred for 48 hours. It was then loaded on a silica gel column and eluted with 150 mL of ethyl acetate followed by 90 mL of Isopropanol:$NH_4OH$:$H_2O$ (6.0:2.5:0.5) mixture to give fractions 1 (discarded) and 2, respectively. Fraction 2 was concentrated (until approximately 12 mL of liquid remained) under reduced pressure, loaded on a pre-conditioned (see note 1) DOWEX50WX8-2 column and washed down with 100 mL solution of 0.025 M $NH_4HCO_3$. The resulting filtrate was collected and lyophilized to give albicanyl monophosphate (see note 2) as a "sticky" white solid (9 mg, 0.025 mmol, 7%).

Notes:
1) A column (21 cm tall and 3.5 cm diameter) was filled to 5 cm of Dowex 50WX8 ion-exchange beads, washed down initially with $NH_4OH$/$H_2O$ 3:1 mixture (60 mL, warning: exothermic) followed by 0.025 M $NH_4HCO_3$ solution (120 mL or until filtrate's pH is between 8.5 to 9.5).
2) Contaminated with 14% albicanyl diphosphate.

Example 7

Detection of Albicanyl Diphosphate and Monophosphate as Products of DfHAD Enzyme with High Resolution Mass Spectrometry Preparation of E. coli Extract from Cultured Broth The sequence of DfHAD was optimized by genetic codon frequency for *Escherichia coli*. It was then synthesized in vitro and subcloned into the pETDuet-1 plasmid (Novagen) for subsequent expression in *E. coli*. BL21(DE3). *E. coli* cells (Tiangen) were also co-transformed with the plasmid pACYC/ScMVA, containing the genes encoding for a heterologous mevalonate pathway, and the plasmid pETDuet-DfHAD. The co-transformed cells were selected on LB-agar plates containing ampicillin (50 μg/mL final) and chloramphenicol (34 μg/mL final). Single colonies were used to inoculate 5 mL liquid LB medium supplemented with the same antibiotics. Cultures were incubated overnight at 37° C. with shaking at 200 rpm. The next day, 200 mL of AM+5Y medium supplemented with the same antibiotics and glycerol (3% w/v final) were inoculated with 2 mL of the overnight culture. After 5 hours of incubation at 37° C. and shaking at 200 rpm, the culture was cooled down to 25° C., shaken a further 1 hour at 200 rpm, then IPTG (0.1 mM final) was added to each flask. The cultures were incubated for a further 48 hours at 25° C. at 200 rpm.

The cultures were sonicated and centrifuged. The supernatants of cultures were adjusted to pH 8.0 by ammonia water before loading to SPE column. The Sep-Pak C18 cartridge (6 cc/500 mg, Waters, M A) was conditioned with 10 mL MeOH and 15 mL 10 mM $NH_4HCO_3$, and 40 mL culture samples were loaded onto the SPE column. The cartridge was then eluted with 3 mL MeOH/10 mM $NH_4HCO_3$ (90/10, v/v). The eluate was filtered by 0.22 μm hydrophilic PTFE syringe filters for UHPLC Q-Exactive MS analysis.

Analytical Method: UHPLC Q-Exactive MS Analysis

A Vanquish ultra-high performance liquid chromatography coupled to a Q Exactive plus hybrid quadrupole-orbitrap mass spectrometer (Thermo Fisher Scientific) was used in the analysis.

UHPLC was carried out on a Luna 3 μm C18 (100 mm×2 mm) column (Phenomenex, USA) operated at a flow rate of 0.3 mL/min. The mobile phase consisted of A: 5 mM $HCOONH_4$ adjusted to pH 8.0 by ammonia water and B acetonitrile. Elution was accomplished with a linear gradient: 0-0.5 min 15% B; 0.5-7 min, 15%-80% B; 7.01-10.5 min, 98% B, 10.6-13.0 min, 98%-15%. The column temperature was set at 35° C. and the volume of injection was 1 μL. The Q-Exactive MS system was operated with an HESI source in negative ionization mode (ESI−) and acquisition was performed in target SIM-ddMS$^2$ mode or target SIM mode. The parameters of HESI were as follow: sheath gas flow rate 48, aux gas flow rate 11, spray voltage 3.8 KV, capillary temperature 320° C., and aux heater temperature 300° C. The parameters of targeted SIM mode were as follow: resolution 35,000, AGC target 5e4, maximum IT 100 ms, loop count 5, isolation window 4.0 m/z. Inclusion mass was set as 381.1237 [M-H]$^-$ and 301.1574 [M-H]$^-$ for sesquiterpene diphosphate and monophosphate. In the setting of dd-MS$^2$, resolution was 17,500, and stepped nce was 20, 35, 50.

Sesquiterpene monophosphate and diphosphate were semi-quantified by calculation with EIC 381.1237 or 301.1574 area. FPP standard curve was plotted with EIC 381.1237 area and FPP standard concentrations. Because low concentrations of FPP are unstable, the FPP standard solutions were freshly prepared the same day of the samples analysis.

Analytical Result from E. coli Extract

Figure 12:
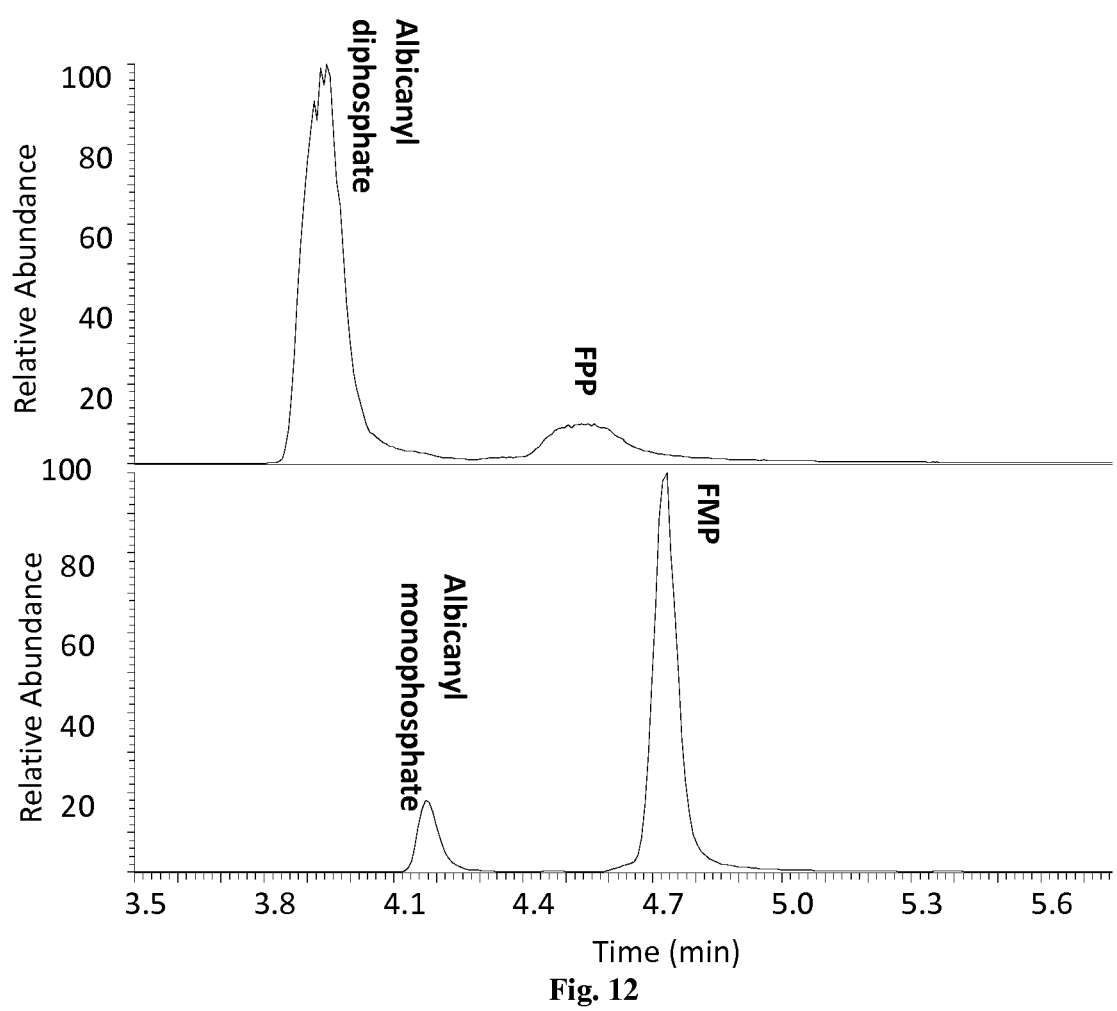
FIG. 12. Chromatogram of extracted ion 381.1237 for sesquiterpene diphosphate (upper) and monophosphate 301.1574 (lower) from purified DfHAD sample mixed with FPP.

In the fermentation of DfHAD expressing *E. coli* strain, albicanyl diphosphate, albicanyl monophosphate, FPP (farnesyl diphosphate) and FMP (farnesyl monophosphate) were identified by their accurate molecular weight, characteristic fragment ions and synthesized standards. Albicanyl diphosphate (52.7 ng/mL) and FPP (48.3 ng/mL) were at trace level, while albicanyl monophosphate (2.9 μg/mL) and FMP (4.8 μg/mL) dominated, which are similar to amounts of albicanol (2.1 μg/mL) and farnesol (10.5 μg/mL) (FIG. 12).

In Vitro Biochemical Assay for the Detection of Albicanyl Mono and Di-Phosphate

In order to purify DfHAD, its coding sequence (optimised for *E. coli* expression) was subcloned into a modified plasmid pGS-21a (Genscript). The plasmid was modified to allow for the insertion of the gene between a KpnI and an NdeI restriction site. The expressed protein is fused with an N-terminus 6×His-GST-tag. After transformation in BL21 (DE3) *E. coli* cells and selection on LB-agar plates containing ampicillin (50 μg/mL final), a single colony was inoculated into 40 mL LB media supplemented with the same antibiotics and the cultures were incubated at 37° C., 180 rpm overnight. The next day, 5-10 mL of the culture was inoculated into 500 mL of 2×YT media containing ampicillin at 50 mg/L and incubated at 37° C., 150 rpm for ~3 hours (OD600=0.7–1.2). The culture was then cooled down to 25° C. for 1.5 hours and 0.25 mL of 1 M IPTG was added, then incubated at 25° C., 150 rpm for 18 hours. The culture was harvested by centrifugation at 4° C. for 15 min at 3500 g and the pellet was washed twice with chilled Buffer A (50 mM $Na_2HPO_4$, 10 mM imidazole, 500 mM NaCl, pH7.8). The pellet was resuspended in Buffer A containing proteases inhibitor (SigmaFast EDTA-free, Sigma) and the volume adjusted to 25 mL. 25 mg of Lysozyme, 25 μL DNase I, 125 μL $MgCl_2$, and 60 μL of 0.2 M PMSF were added to the suspension. After incubation on ice for 30 min followed by sonication (3 sec ON, 12 sec OFF, 3 min total, repeated once) the supernatant was harvested by centrifugation at 4° C. and 8000 g for 10 min. The protein was purified by the batch method on glutathione-agarose (Sigma G4510) according to the manufacturer protocol for GST-tagged protein.

For the in vitro biochemical assay of DfHAD protein, 1.5 μM of purified recombinant protein was added to a 2 ml reaction mixture containing 10 mM $MgCl_2$, 5 mM DTT, 128 μM FPP in a 50 mM Tris-HCl pH 8.0 buffer. The samples were incubated at 30° C., 50 rpm for 2 h. The samples were then split in two and in one of them 20 μL of a bacterial alkaline phosphatase (Sangon-B004081-100) was added and the reaction pursued for an extra 1 h at 25° C. A control with no protein added was also run in the same conditions.

Analytical Results for the In Vitro Assay with DfHAD

Both albicanyl diphosphate and albicanyl monophosphate were identified in the in vitro assay (FIG. 13). A 20:1 ratio albicanyl diphosphate:albicanyl monophosphate was observed as well as FPP and farnesyl monophosphate (FMP), while albicanol was not detected (Table 1). Sesquiterpene diphosphates such as albicanyl diphosphate and FPP are unstable and easily degrade to their monophosphates. Albicanyl monophosphate and FMP from the in vitro biochemical assay can be the degradation products of their respective diphosphate precursors.

After addition of the phosphatase BAP, no more sesquiterpene phosphates were observed, while albicanol and farnesol were detected. Therefore, the major product of DfHAD is albicanyl diphosphate, and albicanol is produced from albicanyl diphosphate by one or two phosphatases.

TABLE 1

| Samples | Concentration of sesquiterpene phosphates and sesquiterpenes (μg/mL) | | | | | |
|---|---|---|---|---|---|---|
| | Albicanyl diphosphate | Albicanyl monophosphate | FPP | FMP | Albicanol | Farnesol |
| Purified DfHAD mixed with FPP | 20.6 | 1.0 | 3.7 | 6.3 | ND[a] | ND[a] |
| Purified DfHAD mixed with FPP and BAP | ND[a] | 0.2 | 0.1 | ND[a] | 4.6 | 7.2 |

[a]Not Detected

Example 8

The Preparation of Mutants of DfHAD Enzyme and Determination of their In Vitro Activity The amino acid sequence of native DfHAD (SEQ ID NO:2) was modified in particular conserved amino acid sequence motifs in order to determine criticality of these motifs for the enzyme activity.

For this purpose synthetic genes of 4 different mutants of the native DfHAD enzyme of SEQ ID NO: 2 were prepared by a commercial supplier. The genes were expressed in vitro and then the activity was determined as described in Example 2, above. In particular the concentration of albicanol (mg/L/OD) was determined by GC/MS. The results are summarised in subsequent Table 2.

TABLE 2

| | | DfHAD enzyme mutants and their and enzyme activity | | | |
|---|---|---|---|---|---|
| Mutants | SEQ ID NO: | Mutated Motif mutant positions underlined | Mean (mg/L/OD) | SD | Function (%) |
| DfHAD | 2 | | 0.39 | 0.06 | 100 |
| DfHAD-QW mut | 20 | QCAAAGCW (SEQ ID NO: 26) | 0.15 | 0.01 | 38 |
| DfHAD-QW fungal | 19 | QCEDGGW (SEQ ID NO: 27) | 0.77 | 0.08 | 196 |
| DfHAD-MOSmotif | 22 | DGILQVAAAVERPRIDPVVVAN (SEQ ID NO: 28) | 0 | 0 | 0 |
| DfHAD-SEQ64motif | 21 | DSFDPLE (SEQ ID NO: 29) | 0.02 | 0.003 | 4 |

Native Motifs:
DSFDSLE (SEQ ID NO: 13);
QCKSKGCW (SEQ ID NO: 24)
and
DGILQVYFDVERPRIDPVVVAN (SEQ ID NO: 25)

The experimental results clearly show that each of the above-mentioned sequence motifs is critical to that same activity. Changing the modified class I motif (SEQ ID NO:14) into SEQ ID NO: 29) may results in an almost complete activity loss. This changing native synthase motif III (SEQ ID NO:24) into SEQ ID NO:26 significantly reduces enzyme activity, while in exchange by the respective conserved fungal motive SEQ ID NO:27 results in a doubling of the enzyme activity. Mutating native synthase motif IV (SEQ ID NO:25) may result in a complete loss of activity.

The content of the documents cross-referenced herein is incorporated by reference.

TABLE 3

| | Sequences as herein referred to are: | | |
|---|---|---|---|
| SEQ ID NO | Name | Source | Type |
| 1 | DfHAD | *Dryopteris fragrans* | NA |
| 2 | DfHAD | *Dryopteris fragrans* | AA |
| 3 | DfHAD-8 (K532R) | *Dryopteris fragrans* | NA |
| 4 | DfHAD-8 (K532R) | *Dryopteris fragrans* | AA |
| 5 | DfHAD-9 (V274A) | *Dryopteris fragrans* | NA |
| 6 | DfHAD-9 (V274A) | *Dryopteris fragrans* | AA |
| 7 | DfHAD codon optimized for *E. coli* | Artificial | NA |
| 8 | DfHAD codon optimized for Tobacco | Artificial | NA |
| 9 | DfHAD-8 (K532R) codon optimized for *E. coli* | Artificial | NA |
| 10 | DfHAD-9 (V274A) codon optimized for *E. coli* | Artificial | NA |
| 11 | Modified class I synthase motif | Artificial | NA |
| 12 | Modified class II synthase motif | Artificial | NA |
| 13 | Modified class I synthase motif | Artificial | NA |
| 14 | Modified class II synthase motif | Artificial | NA |
| 15 | Forward primer | Artificial | NA |
| 16 | Reverse primer | Artificial | NA |
| 17 | DfHAD-His-GST | Artificial | NA |
| 18 | DfHAD-His-GST | Artificial | AA |
| 19 | DfHAD-QW fungal | Artificial | AA |
| 20 | DfHAD-QW mut | Artificial | AA |
| 21 | DfHAD-SEQ64-motif | Artificial | AA |

TABLE 3-continued

Sequences as herein referred to are:

| SEQ ID NO | Name | Source | Type |
|---|---|---|---|
| 22 | DfHAD-MOS-motif | Artificial | AA |
| 23 | Alternative class II synthase motif | Artificial | AA |
| 24 | Synthase motif III | Artificial | AA |
| 25 | Synthase motif IV | Artificial | AA |
| 26 | Modified synthase motif III | Artificial | AA |
| 27 | Modified synthase motif III | Artificial | AA |
| 28 | Modified synthase motif IV | Artificial | AA |
| 29 | Modified class I synthase motif | Artificial | AA |

NA = Nucleic Acid

AA = Amino Acid

Sequences
Coding sequence for DfHAD (SEQ ID NO: 1)

ATGGAGTTCTCTGCCTCTGCTCCTCCTCCTAGGCTAGCCAGTGTCATAATATTGGAGCCTCT

CGGCTTCCTCCTCACACCACACTACTCCTCTCAGCTTCCCAAAAAGCTGCTCCGTCGCCTGT

TGTGCACTAGAATCTGGCACAGGTATCAGCGAGGCCGCCTTCGCCTGCGTGACGCTGCTATG

CTGCTCGCCCAGCTCCCATTCCTAGCTGTGTCTGATCACCCCTGGGCTCTGGACAATCTCGC

AAGCCTGCTCCGCCCCACAGCTGTGCGTGCGGTGCCATGGATGCTGCTGCTGCTCGACTTCC

TACGAGACGAGCTCCATCTGAAGGTAGTCTGCGCGACCAACTCCTCCCCAGAAGAGCTGCAA

GAGCTGCGCCACCAGTTTCCGGCCCTCTTTGCCAAGGTCGATGCCACCGTTTCTTCAGGCGA

GGAGGGCGTGGGCAAGCCGTCCGTGCGCTTCCTGCAGGCTGCGTTGGACAAAGCCGGTGTCC

ACGCGCAGCAAACCTTGTATCTTGACTCTTTTGACAGCTTGGAGACCATCATGGCTGCACGC

TCTCTTGGCATGCATGCACTATCTGTAGAGCCATGCCACATTGATGAGCTCACCGCCAGGGC

CTCTTCCGGCCAGCTAAGAGATGCACAGCTTATAAGGCGTATTGTGTGCGCCATGCACGGGC

CAGCAGTATCTGCAGTTGTGTCGGGCAGTATCACATCGTCCGGCCCACAGACAGCAAAGATC

GAGGAATTGCCAACAGCTGCTGATAGTCATCTCCGCAGCGCAGCTCTCACTTCTGCTCAGCA

GTTTTTCCTCAAAGTTATTGCTCCACATCGTCCTGAGAAGCCATTCGTCCAGCTTCCATCTC

TCACCTCGGAGGGCATCCGAATATACGACACCTTTGCACAGTTTGTCATAGCCGACCTGCTC

GACGACACCCGCTTCCTACCCATGCAATCTCCTCCTCCCAATGGGCTCATCACCTTTGTTAA

CCCAAGCGCGTACCTTGCTGATGATATAAAGAATGGCAACAGCCATATTGTCCCGGGTGTGC

AATTTTACGCATCCGATGCGTGCACTCTCATCGACATCCCACATGACCTAGACACCACCTCC

GTTGGCTTGTCAGTACTGCACAAGTTTGGAAAGGTGGACAAGGACACACTCAACAAAGTGCT

AGACAGAATGCTCGAGCAAGTGAGTGAAGACGACGGCATTCTGCAGGTGTATTTTGATGTGG

AGCGTCCGCGCATCGATCCAGTTGTGGTGGCAAACACGGTGTTTCTGTTCCACTTGGGAAAG

AGAGGGCATGAGGTGGCGAGGAGTGAGAAGTTTGTGGAGAGTGTGCTGCTGCAGAGGGCATA

CGAAGAAGGGACGTTGTATTACAACCTGGGGGAAGCATTTTGGTGAGTGTGGCGAGGCTGG

TGCACGAGTTTAAGGAGCACTTTACAAGGAGCGGCATGAGGAGGGCACTGGAGGAGAGGCTA

AGAGAGCGGGCAAGGGCGGGCATGCAAGAGAGGGATGATGCGCTGGCGCTAGCCATGCGCAT

TCGTGCATGCGCTTTGTGTGGCCTGGCCGGAGAGGGCCTCACAAAAGCAGCAGAGCAGGAGC

TTTTGCGCCTGCAGTGCAAGTCCAAGGGCTGTTGGGGGTGCCACCCTTTCTATCGCAATGGC

AGTAATGTGCTCAGCTGGATCGGCAGTGAGGCCCTTACCACTGCTTACGCTATTGCTGCGCT

ACAGCCCATTGATATTTAA

-continued

Amino acid Sequence for DfHAD
(SEQ ID NO: 2)
MEFSASAPPPRLASVIILEPLGFLLTPHYSSQLPKKLLRRLLCTRIWHRYQRGRLRLRDAAM

LLAQLPFLAVSDHPWALDNLASLLRPTAVRAVPWMLLLLDFLRDELHLKVVCATNSSPEELQ

ELRHQFPALFAKVDATVSSGEEGVGKPSVRFLQAALDKAGVHAQQTLYLDSFDSLETIMAAR

SLGMHALSVEPCHIDELTARASSGQLRDAQLIRRIVCAMHGPAVSAVVSGSITSSGPQTAKI

EELPTAADSHLRSAALTSAQQFFLKVIAPHRPEKPFVQLPSLTSEGIRIYDTFAQFVIADLL

DDTRFLPMQSPPPNGLITFVNPSAYLADDIKNGNSHIVPGVQFYASDACTLIDIPHDLDTTS

VGLSVLHKFGKVDKDTLNKVLDRMLEQVSEDDGILQVYFDVERPRIDPVVVANTVFLFHLGK

RGHEVARSEKFVESVLLQRAYEEGTLYYNLGEAFLVSVARLVHEFKEHFTRSGMRRALEERL

RERARAGMQERDDALALAMRIRACALCGLAGEGLTKAAEQELLRLQCKSKGCWGCHPFYRNG

SNVLSWIGSEALTTAYAIAALQPIDI

Coding sequence for DfHAD-8(K532R)
(SEQ ID NO: 3)
ATGGAGTTCTCTGCCTCTGCTCCTCCTCCTAGGCTAGCCAGTGTCATAATATTGGAGCCTCT

CGGCTTCCTCCTCACACCACACTACTCCTCTCAGCTTCCCAAAAAGCTGCTCCGTCGCCTGT

TGTGCACTAGAATCTGGCACAGGTATCAGCGAGGCCGCCTTCGCCTGCGTGACGCTGCTATG

CTGCTCGCCCAGCTCCCATTCCTAGCTGTGTCTGATCACCCCTGGGCTCTGGACAATCTCGC

AAGCCTGCTCCGCCCCACAGCTGTGCGTGCGGTGCCATGGATGCTGCTGCTGCTCGACTTCC

TACGAGACGAGCTCCATCTGAAGGTAGTCTGCGCGACCAACTCCTCCCCAGAAGAGCTGCAA

GAGCTGCGCCACCAGTTTCCGGCCCTCTTTGCCAAGGTCGATGCCACCGTTTCTTCAGGCGA

GGAGGGCGTGGGCAAGCCGTCCGTGCGCTTCCTGCAGGCTGCGTTGGACAAAGCCGGTGTCC

ACGCGCAGCAAACCTTGTATCTTGACTCTTTTGACAGCTTGGAGACCATCATGGCTGCACGC

TCTCTTGGCATGCATGCACTATCTGTAGAGCCATGCCACATTGATGAGCTCACCGCCAGGGC

CTCTTCCGGCCAGCTAAGAGATGCACAGCTTATAAGGCGTATTGTGTGCGCCATGCACGGGC

CAGCAGTATCTGCAGTTGTGTCGGGCAGTATCACATCGTCCGGCCCACAGACAGCAAAGATC

GAGGAATTGCCAACAGCTGCTGATAGTCATCTCCGCAGCGCAGCTCTCACTTCTGCTCAGCA

GTTTTTCCTCAAAGTTATTGCTCCACATCGTCCTGAGAAGCCATTCGTCCAGCTTCCATCTC

TCACCTCGGAGGGCATCCGAATATACGACACCTTTGCACAGTTTGTCATAGCCGACCTGCTC

GACGACACCCGCTTCCTACCCATGCAATCTCCTCCTCCCAATGGGCTCATCACCTTTGTTAA

CCCAAGCGCGTACCTTGCTGATGATATAAAGAATGGCAACAGCCATATTGTCCCGGGTGTGC

AATTTTACGCATCCGATGCGTGCACTCTCATCGACATCCCACATGACCTAGACACCACCTCC

GTTGGCTTGTCAGTACTGCACAAGTTTGGAAAGGTGGACAAGGACACACTCAACAAAGTGCT

AGACAGAATGCTCGAGCAAGTGAGTGAAGACGACGGCATTCTGCAGGTGTATTTTGATGTGG

AGCGTCCGCGCATCGATCCAGTTGTGGTGGCAAACACGGTGTTTCTGTTCCACTTGGGAAAG

AGAGGGCATGAGGTGGCGAGGAGTGAGAAGTTTGTGGAGAGTGTGCTGCTGCAGAGGGCATA

CGAAGAAGGGACGTTGTATTACAACCTGGGGGAAGCATTTTTGGTGAGTGTGGCGAGGCTGG

TGCACGAGTTTAAGGAGCACTTTACAAGGAGCGGCATGAGGAGGGCACTGGAGGAGAGGCTA

AGAGAGCGGGCAAGGGCGGGCATGCAAGAGAGGGATGATGCGCTGGCGCTGGCCATGCGCAT

TCGTGCATGCGCTTTGTGTGGCCTGGCCGGAGAGGGCCTCACAAGAGCAGCAGAGCAGGAGC

TACTGCGCCTGCAGTGCAAGTCCAAGGGCTGTTGGGGGTGCCACCCTTTCTATCGCAATGGC

AGTAATGTGCTCAGCTGGATCGGCAGTGAGGCCCTTACCACTGCTTACGCTATTGCTGCGCT

ACAGCCCATTGATATTTAA

Amino acid Sequence for DfHAD-8(K532R)
(SEQ ID NO: 4)
MEFSASAPPPRLASVIILEPLGFLLTPHYSSQLPKKLLRRLLCTRIWHRYQRGRLRLRDAAM

LLAQLPFLAVSDHPWALDNLASLLRPTAVRAVPWMLLLLDFLRDELHLKVVCATNSSPEELQ

ELRHQFPALFAKVDATVSSGEEGVGKPSVRFLQAALDKAGVHAQQTLYLDSFDSLETIMAAR

SLGMHALSVEPCHIDELTARASSGQLRDAQLIRRIVCAMHGPAVSAVVSGSITSSGPQTAKI

EELPTAADSHLRSAALTSAQQFFLKVIAPHRPEKPFVQLPSLTSEGIRIYDTFAQFVIADLL

DDTRFLPMQSPPPNGLITFVNPSAYLADDIKNGNSHIVPGVQFYASDACTLIDIPHDLDTTS

VGLSVLHKFGKVDKDTLNKVLDRMLEQVSEDDGILQVYFDVERPRIDPVVVANTVFLFHLGK

RGHEVARSEKFVESVLLQRAYEEGTLYYNLGEAFLVSVARLVHEFKEHFTRSGMRRALEERL

RERARAGMQERDDALALAMRIRACALCGLAGEGLTRAAEQELLRLQCKSKGCWGCHPFYRNG

SNVLSWIGSEALTTAYAIAALQPIDI

Coding sequence for DfHAD-9(V274A)
(SEQ ID NO: 5)
ATGGAGTTCTCTGCCTCTGCTCCTCCTCCTAGGCTAGCCAGTGTCATAATATTGGAGCCTCT

CGGCTTCCTCCTCACACCACACTACTCCTCTCAGCTTCCCAAAAAGCTGCTCCGTCGCCTGT

TGTGCACTAGAATCTGGCACAGGTATCAGCGAGGCCGCCTTCGCCTGCGTGACGCTGCTATG

CTGCTCGCCCAGCTCCCATTCCTAGCTGTGTCTGATCACCCCTGGGCTCTGGACAATCTCGC

AAGCCTGCTCCGCCCCACAGCTGTGCGTGCGGTGCCATGGATGCTGCTGCTGCTCGACTTCC

TACGAGACGAGCTCCATCTGAAGGTAGTCTGCGCGACCAACTCCTCCCCAGAAGAGCTGCAA

GAGCTGCGCCACCAGTTTCCGGCCCTCTTTGCCAAGGTCGATGCCACCGTTTCTTCAGGCGA

GGAGGGCGTGGGCAAGCCGTCCGTGCGCTTCCTGCAGGCTGCGTTGGACAAAGCGGTGTCC

ACGCGCAGCAAACCTTGTATCTTGACTCTTTTGACAGCTTGGAGACCATCATGGCTGCACGC

TCTCTTGGCATGCATGCACTATCTGTAGAGCCATGCCACATTGATGAGCTCACCGCCAGGGC

CTCTTCCGGCCAGCTAAGAGATGCACAGCTTATAAGGCGTATTGTGTGCGCCATGCACGGGC

CAGCAGTATCTGCAGTTGTGTCGGGCAGTATCACATCGTCCGGCCCACAGACAGCAAAGATC

GAGGAATTGCCAACAGCTGCTGATAGTCATCTCCGCAGCGCAGCTCTCACTTCTGCTCAGCA

GTTTTTCCTCAAAGCTATTGCTCCACATCGTCCTGAGAAGCCATTCGTCCAGCTTCCATCTC

TCACCTCGGAGGGCATCCGAATATACGACACCTTTGCACAGTTTGTCATAGCCGACCTGCTC

GACGACACCCGCTTCCTACCCATGCAATCTCCTCCTCCCAATGGGCTCATCACCTTTGTTAA

CCCAAGCGCGTACCTTGCTGATGATATAAAGAATGGCAACAGCCATATTGTCCCGGGTGTGC

AATTTTACGCATCTGATGCGTGCACTCTCATCGACATCCCACATGACCTAGACACCACCTCC

GTTGGCTTGTCAGTACTGCACAAGTTTGGAAAGGTGGACAAGGACACACTCAACAAAGTGCT

AGACAGAATGCTGGAGCAAGTGAGTGAAGACGACGGCATTCTCCAGGTGTATTTTGATGTGG

AGCGTCCGCGCATCGATCCAGTTGTGGTGGCAAACACGGTGTTTCTGTTCCACTTGGGAAAG

AGAGGGCATGAGGTGGCGAGGAGTGAGAAGTTTGTGGAGAGTGTGCTGCTGCAGAGGGCATA

CGAAGAAGGGACGTTGTATTACAACCTGGGGGAAGCATTTTTGGTGAGTGTGGCGAGGCTGG

TGCACGAGTTTAAGGAGCACTTTACAAGGAGCGGCATGAGGAGGGCACTGGAGGAGAGGCTA

AGAGAGCGGGCAAGGGCGGGCATGCAAGAGAGGGATGATGCGCTGGCGCTGGCCATGCGCAT

TCGTGCATGCGCTTTGTGTGGCCTGGCCGGAGAGGGCCTCACAAAAGCAGCAGAGCAGGAGC

TACTGCGCCTGCAGTGCAAGTCCAAGGGCTGTTGGGGGTGCCACCCTTTCTATCGCAATGGC

AGTAATGTGCTCAGCTGGATCGGCAGTGAGGCCCTTACCACTGCTTACGCTATTGCTGCGCT

ACAGCCCATTGATATTTAA

Amino acid Sequence for DfHAD-9(V274A)
(SEQ ID NO: 6)
MEFSASAPPPRLASVIILEPLGFLLTPHYSSQLPKKLLRRLLCTRIWHRYQRGRLRLRDAAM

LLAQLPFLAVSDHPWALDNLASLLRPTAVRAVPWMLLLLDFLRDELHLKVVCATNSSPEELQ

ELRHQFPALFAKVDATVSSGEEGVGKPSVRFLQAALDKAGVHAQQTLYLDSFDSLETIMAAR

SLGMHALSVEPCHIDELTARASSGQLRDAQLIRRIVCAMHGPAVSAVVSGSITSSGPQTAKI

EELPTAADSHLRSAALTSAQQFFLKAIAPHRPEKPFVQLPSLTSEGIRIYDTFAQFVIADLL

DDTRFLPMQSPPPNGLITFVNPSAYLADDIKNGNSHIVPGVQFYASDACTLIDIPHDLDTTS

VGLSVLHKFGKVDKDTLNKVLDRMLEQVSEDDGILQVYFDVERPRIDPVVVANTVFLFHLGK

RGHEVARSEKFVESVLLQRAYEEGTLYYNLGEAFLVSVARLVHEFKEHFTRSGMRRALEERL

RERARAGMQERDDALALAMRIRACALCGLAGEGLTKAAEQELLRLQCKSKGCWGCHPFYRNG

SNVLSWIGSEALTTAYAIAALQPIDI

Codon-optimized sequence of DfHAD by Genscript genetic codon
frequency of *E. coli*
(SEQ ID NO: 7)
ATGGAGTTCAGCGCGAGCGCTCCGCCGCCGCGTCTGGCGAGCGTGATCATTCTGGAACCGCT

GGGTTTTCTGCTGACCCCGCACTACAGCAGCCAGCTGCCGAAGAAACTGCTGCGTCGTCTGC

TGTGCACCCGTATCTGGCACCGTTATCAGCGTGGCCGTCTGCGTCTGCGTGACGCGGCGATG

CTGCTGGCGCAACTGCCGTTCCTGGCGGTTAGCGACCACCCGTGGGCGCTGGATAACCTGGC

GAGCCTGCTGCGTCCGACCGCGGTTCGTGCGGTGCCGTGGATGCTGCTGCTGCTGGACTTTC

TGCGTGATGAGCTGCACCTGAAAGTGGTTTGCGCGACCAACAGCAGCCCGGAGGAACTGCAG

GAACTGCGTCACCAATTCCCGGCGCTGTTTGCGAAGGTTGACGCGACCGTGAGCAGCGGCGA

GGAAGGTGTTGGCAAACCGAGCGTGCGTTTCCTGCAAGCGGCGCTGGATAAGGCGGGCGTGC

ACGCGCAGCAAACCCTGTACCTGGACAGCTTTGATAGCCTGGAGACCATCATGGCGGCGCGT

AGCCTGGGTATGCACGCGCTGAGCGTTGAGCCGTGCCACATTGACGAACTGACCGCGCGTGC

GAGCAGCGGTCAGCTGCGTGATGCGCAACTGATCCGTCGTATTGTTTGCGCGATGCACGGTC

CGGCTGTGAGCGCGGTGGTTAGCGGTAGCATCACCAGCAGCGGTCCGCAGACCGCGAAAATT

GAGGAACTGCCGACCGCGGCGGACAGCCACCTGCGTAGCGCGGCGCTGACCAGCGCGCAGCA

ATTCTTTCTGAAAGTGATTGCGCCGCACCGTCCGGAGAAGCCGTTCGTTCAACTGCCGAGCC

TGACCAGCGAAGGTATCCGTATTTATGACACCTTCGCGCAGTTTGTGATCGCGGATCTGCTG

GACGATACCCGTTTCCTGCCGATGCAAAGCCCGCCGCCGAACGGCCTGATTACCTTTGTTAA

CCCGAGCGCGTACCTGGCGGACGATATCAAAAACGGTAACAGCCACATTGTTCCGGGCGTGC

AGTTCTATGCGAGCGACGCGTGCACCCTGATCGATATTCCGCACGACCTGGATACCACCAGC

GTTGGTCTGAGCGTGCTGCACAAGTTTGGCAAAGTTGACAAGGATACCCTGAACAAGGTGCT

GGATCGTATGCTGGAGCAAGTTAGCGAAGACGATGGTATCCTGCAAGTTTACTTTGACGTGG

AGCGTCCGCGTATTGATCCGGTGGTTGTGGCGAACACCGTGTTCCTGTTTCACCTGGGTAAA

CGTGGCCACGAAGTTGCGCGTAGCGAGAAGTTCGTTGAAAGCGTGCTGCTGCAGCGTGCGTA

CGAGGAAGGCACCCTGTACTATAACCTGGGCGAAGCGTTTCTGGTTAGCGTGGCGCGTCTGG

TGCACGAGTTCAAAGAACACTTTACCCGTAGCGGTATGCGTCGTGCGCTGGAGGAACGTCTG

CGTGAGCGTGCGCGTGCGGGTATGCAAGAACGTGACGATGCGCTGGCGCTGGCGATGCGTAT

CCGTGCGTGCGCGCTGTGCGGTCTGGCGGGCGAGGGTCTGACCAAGGCGGCGGAGCAGGAAC

TGCTGCGTCTGCAATGCAAGAGCAAAGGTTGCTGGGGCTGCCACCCGTTCTACCGTAACGGT

AGCAACGTTCTGAGCTGGATCGGCAGCGAAGCGCTGACCACCGCGTATGCGATTGCGGCGCT

GCAGCCGATCGACATTTAA

Codon-optimized sequence of DfHAD by Genscript genetic codon
frequency of tobacco (SEQ ID NO: 8)

ATGGAATTTTCTGCTTCAGCTCCACCTCCAAGACTTGCTTCAGTTATTATTCTTGAGCCTTT

GGGATTTCTTTTGACTCCACATTACTCTTCACAATTGCCTAAGAAACTTTTGAGAAGGCTTT

TGTGTACAAGAATTTGGCATAGGTACCAAAGGGGTAGGCTTAGATTGAGGGATGCTGCTATG

CTTTTGGCTCAACTTCCATTTTTGGCTGTTTCAGATCATCCTTGGGCTCTTGATAATTTGGC

TTCTCTTTTGAGACCAACTGCTGTTAGGGCTGTTCCTTGGATGCTTTTGCTTTTGGATTTTC

TTAGAGATGAACTTCATTTGAAGGTTGTTTGCGCTACTAATTCTTCACCAGAAGAGCTTCAA

GAGTTGAGGCATCAATTTCCTGCTTTGTTTGCTAAGGTTGATGCTACAGTTTCTTCAGGAGA

AGAGGGAGTTGGTAAACCATCTGTTAGATTTCTTCAAGCTGCTTTGGATAAGGCTGGTGTTC

ATGCTCAACAAACTCTTTATTTGGATTCTTTCGATTCACTTGAAACAATTATGGCTGCTAGG

TCATTGGGAATGCATGCTCTTTCTGTTGAACCATGTCATATTGATGAGTTGACTGCTAGAGC

TTCTTCAGGACAATTGAGGGATGCTCAACTTATTAGAAGGATTGTTTGCGCTATGCATGGTC

CTGCTGTTTCAGCTGTTGTTTCTGGATCAATTACTTCTTCAGGTCCACAAACAGCTAAAATT

GAAGAGCTTCCTACTGCTGCTGATTCTCATTTGAGATCAGCTGCTCTTACATCTGCTCAACA

ATTTTTCCTTAAAGTTATTGCTCCACATAGACCTGAAAAGCCATTTGTTCAACTTCCTTCTT

TGACTTCAGAGGGAATCAGGATCTATGATACATTCGCTCAATTCGTTATCGCTGATCTTTTG

GATGATACTAGGTTTTTGCCAATGCAATCACCTCCACCTAATGGTCTTATCACATTCGTTAA

CCCTTCTGCTTATTTGGCTGATGATATTAAAAATGGTAACTCACATATTGTTCCAGGTGTTC

AATTTTACGCTTCTGATGCTTGTACTTTGATTGATATTCCTCATGATCTTGATACTACATCT

GTTGGACTTTCAGTTTTGCATAAGTTCGGTAAAGTTGATAAGGATACACTTAATAAGGTTTT

GGATAGAATGCTTGAACAAGTTTCAGAGGATGATGGAATCCTTCAAGTTTACTTCGATGTTG

AAAGACCTAGGATTGATCCAGTTGTTGTTGCTAACACTGTTTTTCTTTTCCATTTGGGAAAA

AGAGGTCATGAGGTTGCTAGATCAGAAAAGTTTGTTGAGTCTGTTCTTTTGCAAAGAGCTTA

CGAAGAGGGAACTTTGTATTACAATCTTGGTGAAGCTTTTCTTGTTTCTGTTGCTAGACTTG

TTCATGAGTTTAAGGAGCATTTTACAAGGTCTGGAATGAGAAGGGCTTTGGAAGAGAGACTT

AGGGAAAGAGCTAGGGCTGGTATGCAAGAGAGATGATGCTCTTGCTTTGGCTATGAGAAT

TAGGGCTTGTGCTCTTTGCGGTTTGGCTGGAGAAGGTCTTACAAAGGCTGCTGAACAAGAGC

TTTTGAGATTGCAATGCAAGTCTAAAGGATGTTGGGGTTGCCATCCATTCTACAGGAATGGT

TCTAACGTTTTGTCATGGATTGGTTCTGAGGCTCTTACTACAGCTTACGCTATTGCTGCTCT

TCAACCTATTGATATTTGA

Codon-optimized sequence of DfHAD-8(K532R) by Genscript
genetic codon frequency of E. coli (SEQ ID NO: 9)

ATGGAGTTCAGCGCGAGCGCTCCGCCGCCGCGTCTGGCGAGCGTGATCATTCTGGAACCGCT

GGGTTTTCTGCTGACCCCGCACTACAGCAGCCAGCTGCCGAAGAAACTGCTGCGTCGTCTGC

TGTGCACCCGTATCTGGCACCGTTATCAGCGTGGCCGTCTGCGTCTGCGTGACGCGGCGATG

CTGCTGGCGCAACTGCCGTTCCTGGCGGTTAGCGACCACCCGTGGGCGCTGGATAACCTGGC

GAGCCTGCTGCGTCCGACCGCGGTTCGTGCGGTGCCGTGGATGCTGCTGCTGCTGGACTTTC

TGCGTGATGAGCTGCACCTGAAAGTGGTTTGCGCGACCAACAGCAGCCCGGAGGAACTGCAG

-continued
GAACTGCGTCACCAATTCCCGGCGCTGTTTGCGAAGGTTGACGCGACCGTGAGCAGCGGCGA

GGAAGGTGTTGGCAAACCGAGCGTGCGTTTCCTGCAAGCGGCGCTGGATAAGGCGGGCGTGC

ACGCGCAGCAAACCCTGTACCTGGACAGCTTTGATAGCCTGGAGACCATCATGGCGGCGCGT

AGCCTGGGTATGCACGCGCTGAGCGTTGAGCCGTGCCACATTGACGAACTGACCGCGCGTGC

GAGCAGCGGTCAGCTGCGTGATGCGCAACTGATCCGTCGTATTGTTTGCGCGATGCACGGTC

CGGCTGTGAGCGCGGTGGTTAGCGGTAGCATCACCAGCAGCGGTCCGCAGACCGCGAAAATT

GAGGAACTGCCGACCGCGGCGGACAGCCACCTGCGTAGCGCGGCGCTGACCAGCGCGCAGCA

ATTCTTTCTGAAAGTGATTGCGCCGCACCGTCCGGAGAAGCCGTTCGTTCAACTGCCGAGCC

TGACCAGCGAAGGTATCCGTATTTATGACACCTTCGCGCAGTTTGTGATCGCGGATCTGCTG

GACGATACCCGTTTCCTGCCGATGCAAAGCCCGCCGCCGAACGGCCTGATTACCTTTGTTAA

CCCGAGCGCGTACCTGGCGGACGATATCAAAAACGGTAACAGCCACATTGTTCCGGGCGTGC

AGTTCTATGCGAGCGACGCGTGCACCCTGATCGATATTCCGCACGACCTGGATACCACCAGC

GTTGGTCTGAGCGTGCTGCACAAGTTTGGCAAAGTTGACAAGGATACCCTGAACAAGGTGCT

GGATCGTATGCTGGAGCAAGTTAGCGAAGACGATGGTATCCTGCAAGTTTACTTTGACGTGG

AGCGTCCGCGTATTGATCCGGTGGTTGTGGCGAACACCGTGTTCCTGTTTCACCTGGGTAAA

CGTGGCCACGAAGTTGCGCGTAGCGAGAAGTTCGTTGAAAGCGTGCTGCTGCAGCGTGCGTA

CGAGGAAGGCACCCTGTACTATAACCTGGGCGAAGCGTTTCTGGTTAGCGTGGCGCGTCTGG

TGCACGAGTTCAAAGAACACTTTACCCGTAGCGGTATGCGTCGTGCGCTGGAGGAACGTCTG

CGTGAGCGTGCGCGTGCGGGTATGCAAGAACGTGACGATGCGCTGGCGCTGGCGATGCGTAT

CCGTGCGTGCGCGCTGTGCGGTCTGGCGGGCGAGGGTCTGACCCGGGCGGCGGAGCAGGAAC

TGCTGCGTCTGCAATGCAAGAGCAAAGGTTGCTGGGGCTGCCACCCGTTCTACCGTAACGGT

AGCAACGTTCTGAGCTGGATCGGCAGCGAAGCGCTGACCACCGCGTATGCGATTGCGGCGCT

GCAGCCGATCGACATTTAA

Codon-optimized sequence of DfHAD-9(V274A) by Genscript
genetic codon frequency of E. coli
(SEQ ID NO: 10)
ATGGAGTTCAGCGCGAGCGCTCCGCCGCCGCGTCTGGCGAGCGTGATCATTCTGGAACCGCT

GGGTTTTCTGCTGACCCCGCACTACAGCAGCCAGCTGCCGAAGAAACTGCTGCGTCGTCTGC

TGTGCACCCGTATCTGGCACCGTTATCAGCGTGGCCGTCTGCGTCTGCGTGACGCGGCGATG

CTGCTGGCGCAACTGCCGTTCCTGGCGGTTAGCGACCACCCGTGGGCGCTGGATAACCTGGC

GAGCCTGCTGCGTCCGACCGCGGTTCGTGCGGTGCCGTGGATGCTGCTGCTGCTGGACTTTC

TGCGTGATGAGCTGCACCTGAAAGTGGTTTGCGCGACCAACAGCAGCCCGGAGGAACTGCAG

GAACTGCGTCACCAATTCCCGGCGCTGTTTGCGAAGGTTGACGCGACCGTGAGCAGCGGCGA

GGAAGGTGTTGGCAAACCGAGCGTGCGTTTCCTGCAAGCGGCGCTGGATAAGGCGGGCGTGC

ACGCGCAGCAAACCCTGTACCTGGACAGCTTTGATAGCCTGGAGACCATCATGGCGGCGCGT

AGCCTGGGTATGCACGCGCTGAGCGTTGAGCCGTGCCACATTGACGAACTGACCGCGCGTGC

GAGCAGCGGTCAGCTGCGTGATGCGCAACTGATCCGTCGTATTGTTTGCGCGATGCACGGTC

CGGCTGTGAGCGCGGTGGTTAGCGGTAGCATCACCAGCAGCGGTCCGCAGACCGCGAAAATT

GAGGAACTGCCGACCGCGGCGGACAGCCACCTGCGTAGCGCGGCGCTGACCAGCGCGCAGCA

ATTCTTTCTGAAAGCGATTGCGCCGCACCGTCCGGAGAAGCCGTTCGTTCAACTGCCGAGCC

TGACCAGCGAAGGTATCCGTATTTATGACACCTTCGCGCAGTTTGTGATCGCGGATCTGCTG

GACGATACCCGTTTCCTGCCGATGCAAAGCCCGCCGCCGAACGGCCTGATTACCTTTGTTAA

```
CCCGAGCGCGTACCTGGCGGACGATATCAAAAACGGTAACAGCCACATTGTTCCGGGCGTGC

AGTTCTATGCGAGCGACGCGTGCACCCTGATCGATATTCCGCACGACCTGGATACCACCAGC

GTTGGTCTGAGCGTGCTGCACAAGTTTGGCAAAGTTGACAAGGATACCCTGAACAAGGTGCT

GGATCGTATGCTGGAGCAAGTTAGCGAAGACGATGGTATCCTGCAAGTTTACTTTGACGTGG

AGCGTCCGCGTATTGATCCGGTGGTTGTGGCGAACACCGTGTTCCTGTTTCACCTGGGTAAA

CGTGGCCACGAAGTTGCGCGTAGCGAGAAGTTCGTTGAAAGCGTGCTGCTGCAGCGTGCGTA

CGAGGAAGGCACCCTGTACTATAACCTGGGCGAAGCGTTTCTGGTTAGCGTGGCGCGTCTGG

TGCACGAGTTCAAAGAACACTTTACCCGTAGCGGTATGCGTCGTGCGCTGGAGGAACGTCTG

CGTGAGCGTGCGCGTGCGGGTATGCAAGAACGTGACGATGCGCTGGCGCTGGCGATGCGTAT

CCGTGCGTGCGCGCTGTGCGGTCTGGCGGGCGAGGGTCTGACCAAGGCGGCGGAGCAGGAAC

TGCTGCGTCTGCAATGCAAGAGCAAAGGTTGCTGGGGCTGCCACCCGTTCTACCGTAACGGT

AGCAACGTTCTGAGCTGGATCGGCAGCGAAGCGCTGACCACCGCGTATGCGATTGCGGCGCT

GCAGCCGATCGACATTTAA

Modified class I motif:
                                                 (SEQ ID NO: 11)
DSFDxx(D/E)

Modified class II motif:
                                                 (SEQ ID NO: 12)
HDxD(T/S)T Modified class I motif:
                                                 (SEQ ID NO: 13)
DSFDSLE Modified class II motif:
                                                 (SEQ ID NO: 14)
HDLDT forward primer
                                                 (SEQ ID NO: 15)
(5'-ATGGAGTTCTCTGCCTCTG-3')

reverse primer
                                                 (SEQ ID NO: 16)
(5'-GGTTTGGCTTATGGAAGGT-3').

Codon-optimized sequence of DfHAD-6His-GST by Genscript
genetic codon frequency of E. coli
                                                 (SEQ ID NO: 17)
ATGTCTGGTTCTCATCATCATCATCATCATAGCAGCGGTATGTCCCCTATACTAGGTTATTG

GAAAATTAAGGGCCTTGTGCAACCCACTCGACTTCTTTTGGAATATCTTGAAGAAAAATATG

AAGAGCATTTGTATGAGCGCGATGAAGGTGATAAATGGCGAAACAAAAAGTTTGAATTGGGT

TTGGAGTTTCCCAATCTTCCTTATTATATTGATGGTGATGTTAAATTAACACAGTCTATGGC

CATCATACGTTATATAGCTGACAAGCACAACATGTTGGGTGGTTGTCCAAAAGAGCGTGCAG

AGATTTCAATGCTTGAAGGAGCGGTTTTGGATATTAGATACGGTGTTTCGAGAATTGCATAT

AGTAAAGACTTTGAAACTCTCAAAGTTGATTTTCTTAGCAAGCTACCTGAAATGCTGAAAAT

GTTCGAAGATCGTTTATGTCATAAAACATATTTAAATGGTGATCATGTAACCCATCCTGACT

TCATGTTGTATGACGCTCTTGATGTTGTTTTATACATGGACCCAATGTGCCTGGATGCGTTC

CCAAAATTAGTTTGTTTTAAAAAACGTATTGAAGCTATCCCACAAATTGATAAGTACTTGAA

ATCCAGCAAGTATATAGCATGGCCTTTGCAGGGCTGGCAAGCACGTTTGGTGGTGGCGACC

ATCCTCCAAAATCGGATCTGGGCCACACAGGCCATAGATCTGACGACGACGACAAGCATATG

GAGTTCAGCGCGAGCGCTCCGCCGCCGCGTCTGGCGAGCGTGATCATTCTGGAACCGCTGGG

TTTTCTGCTGACCCCGCACTACAGCAGCCAGCTGCCGAAGAAACTGCTGCGTCGTCTGCTGT
```

-continued

```
GCACCCGTATCTGGCACCGTTATCAGCGTGGCCGTCTGCGTCTGCGTGACGCGGCGATGCTG

CTGGCGCAACTGCCGTTCCTGGCGGTTAGCGACCACCCGTGGGCGCTGGATAACCTGGCGAG

CCTGCTGCGTCCGACCGCGGTTCGTGCGGTGCCGTGGATGCTGCTGCTGCTGGACTTTCTGC

GTGATGAGCTGCACCTGAAAGTGGTTTGCGCGACCAACAGCAGCCCGGAGGAACTGCAGGAA

CTGCGTCACCAATTCCCGGCGCTGTTTGCGAAGGTTGACGCGACCGTGAGCAGCGGCGAGGA

AGGTGTTGGCAAACCGAGCGTGCGTTTCCTGCAAGCGGCGCTGGATAAGGCGGGCGTGCACG

CGCAGCAAACCCTGTACCTGGACAGCTTTGATAGCCTGGAGACCATCATGGCGGCGCGTAGC

CTGGGTATGCACGCGCTGAGCGTTGAGCCGTGCCACATTGACGAACTGACCGCGCGTGCGAG

CAGCGGTCAGCTGCGTGATGCGCAACTGATCCGTCGTATTGTTTGCGCGATGCACGGTCCGG

CTGTGAGCGCGGTGGTTAGCGGTAGCATCACCAGCAGCGGTCCGCAGACCGCGAAAATTGAG

GAACTGCCGACCGCGGCGGACAGCCACCTGCGTAGCGCGGCGCTGACCAGCGCGCAGCAATT

CTTTCTGAAAGTGATTGCGCCGCACCGTCCGGAGAAGCCGTTCGTTCAACTGCCGAGCCTGA

CCAGCGAAGGTATCCGTATTTATGACACCTTCGCGCAGTTTGTGATCGCGGATCTGCTGGAC

GATACCCGTTTCCTGCCGATGCAAAGCCCGCCGCCGAACGGCCTGATTACCTTTGTTAACCC

GAGCGCGTACCTGGCGGACGATATCAAAAACGGTAACAGCCACATTGTTCCGGGCGTGCAGT

TCTATGCGAGCGACGCGTGCACCCTGATCGATATTCCGCACGACCTGGATACCACCAGCGTT

GGTCTGAGCGTGCTGCACAAGTTTGGCAAAGTTGACAAGGATACCCTGAACAAGGTGCTGGA

TCGTATGCTGGAGCAAGTTAGCGAAGACGATGGTATCCTGCAAGTTTACTTTGACGTGGAGC

GTCCGCGTATTGATCCGGTGGTTGTGGCGAACACCGTGTTCCTGTTTCACCTGGGTAAACGT

GGCCACGAAGTTGCGCGTAGCGAGAAGTTCGTTGAAAGCGTGCTGCTGCAGCGTGCGTACGA

GGAAGGCACCCTGTACTATAACCTGGGCGAAGCGTTTCTGGTTAGCGTGGCGCGTCTGGTGC

ACGAGTTCAAAGAACACTTTACCCGTAGCGGTATGCGTCGTGCGCTGGAGGAACGTCTGCGT

GAGCGTGCGCGTGCGGGTATGCAAGAACGTGACGATGCGCTGGCGCTGGCGATGCGTATCCG

TGCGTGCGCGCTGTGCGGTCTGGCGGGCGAGGGTCTGACCAAGGCGGCGGAGCAGGAACTGC

TGCGTCTGCAATGCAAGAGCAAAGGTTGCTGGGGCTGCCACCCGTTCTACCGTAACGGTAGC

AACGTTCTGAGCTGGATCGGCAGCGAAGCGCTGACCACCGCGTATGCGATTGCGGCGCTGCA

GCCGATCGACATTTAA
```

Amino acid Sequence for DfHAD-6His-GST (SEQ ID NO: 18)

```
MSGSHHHHHHSSGMSPILGYWKIGLVQPTRLLLEYLEEKYEEHLYERDEGDKWRNKKFELG

LEFPNLPYYIDGDVKLTQSMAIIRYIADKHNMLGGCPKERAEISMLEGAVLDIRYGVSRIAY

SKDFETLKVDFLSKLPEMLKMFEDRLCHKTYLNGDHVTHPDFMLYDALDVVLYMDPMCLDAF

PKLVCFKKRIEAIPQIDKYLKSSKYIAWPLQGWQATFGGGDHPPKSDLGHTGHRSDDDDKHM

EFSASAPPPRLASVIILEPLGFLLTPHYSSQLPKKLLRRLLCTRIWHRYQRGRLRLRDAAML

LAQLPFLAVSDHPWALDNLASLLRPTAVRAVPWMLLLLDFLRDELHLKVVCATNSSPEELQE

LRHQFPALFAKVDATVSSGEEGVGKPSVRFLQAALDKAGVHAQQTLYLDSFDSLETIMAARS

LGMHALSVEPCHIDELTARASSGQLRDAQLIRRIVCAMHGPAVSAVVSGSITSSGPQTAKIE

ELPTAADSHLRSAALTSAQQFFLKVIAPHRPEKPFVQLPSLTSEGIRIYDTFAQFVIADLLD

DTRFLPMQSPPPNGLITFVNPSAYLADDIKNGNSHIVPGVQFYASDACTLIDIPHDLDTTSV

GLSVLHKFGKVDKDTLNKVLDRMLEQVSEDDGILQVYFDVERPRIDPVVVANTVFLFHLGKR

GHEVARSEKFVESVLLQRAYEEGTLYYNLGEAFLVSVARLVHEFKEHFTRSGMRRALEERLR

ERARAGMQERDDALALAMRIRACALCGLAGEGLTKAAEQELLRLQCKSKGCWGCHPFYRNGS
```

NVLSWIGSEALTTAYAIAALQPIDI

Amino acid sequence for mutant DfHAD-QW fungal
(SEQ ID NO: 19)
MEFSASAPPPRLASVIILEPLGFLLTPHYSSQLPKKLLRRLLCTRIWHRYQRGRLRLRDAAM

LLAQLPFLAVSDHPWALDNLASLLRPTAVRAVPWMLLLLDFLRDELHLKVVCATNSSPEELQ

ELRHQFPALFAKVDATVSSGEEGVGKPSVRFLQAALDKAGVHAQQTLYLDSFDSLETIMAAR

SLGMHALSVEPCHIDELTARASSGQLRDAQLIRRIVCAMHGPAVSAVVSGSITSSGPQTAKI

EELPTAADSHLRSAALTSAQQFFLKVIAPHRPEKPFVQLPSLTSEGIRIYDTFAQFVIADLL

DDTRFLPMQSPPPNGLITFVNPSAYLADDIKNGNSHIVPGVQFYASDACTLIDIPHDLDTTS

VGLSVLHKFGKVDKDTLNKVLDRMLEQVSEDDGILQVYFDVERPRIDPVVVANTVFLFHLGK

RGHEVARSEKFVESVLLQRAYEEGTLYYNLGEAFLVSVARLVHEFKEHFTRSGMRRALEERL

RERARAGMQERDDALALAMRIRACALCGLAGEGLTKAAEQELLRLQCEDGGWGCHPFYRNGS

NVLSWIGSEALTTAYAIAALQPIDI*

Amino acid sequence for mutant DfHADQW mut
(SEQ ID NO: 20)
MEFSASAPPPRLASVIILEPLGFLLTPHYSSQLPKKLLRRLLCTRIWHRYQRGRLRLRDAAM

LLAQLPFLAVSDHPWALDNLASLLRPTAVRAVPWMLLLLDFLRDELHLKVVCATNSSPEELQ

ELRHQFPALFAKVDATVSSGEEGVGKPSVRFLQAALDKAGVHAQQTLYLDSFDSLETIMAAR

SLGMHALSVEPCHIDELTARASSGQLRDAQLIRRIVCAMHGPAVSAVVSGSITSSGPQTAKI

EELPTAADSHLRSAALTSAQQFFLKVIAPHRPEKPFVQLPSLTSEGIRIYDTFAQFVIADLL

DDTRFLPMQSPPPNGLITFVNPSAYLADDIKNGNSHIVPGVQFYASDACTLIDIPHDLDTTS

VGLSVLHKFGKVDKDTLNKVLDRMLEQVSEDDGILQVYFDVERPRIDPVVVANTVFLFHLGK

RGHEVARSEKFVESVLLQRAYEEGTLYYNLGEAFLVSVARLVHEFKEHFTRSGMRRALEERL

RERARAGMQERDDALALAMRIRACALCGLAGEGLTKAAEQELLRLQCAAAGCWGCHPFYRNG

SNVLSWIGSEALTTAYAIAALQPIDI*

Amino acid sequence for mutant DfHAD-SEQ64motif
(SEQ ID NO: 21)
MEFSASAPPPRLASVIILEPLGFLLTPHYSSQLPKKLLRRLLCTRIWHRYQRGRLRLRDAAM

LLAQLPFLAVSDHPWALDNLASLLRPTAVRAVPWMLLLLDFLRDELHLKVVCATNSSPEELQ

ELRHQFPALFAKVDATVSSGEEGVGKPSVRFLQAALDKAGVHAQQTLYLDSFDPLETIMAAR

SLGMHALSVEPCHIDELTARASSGQLRDAQLIRRIVCAMHGPAVSAVVSGSITSSGPQTAKI

EELPTAADSHLRSAALTSAQQFFLKVIAPHRPEKPFVQLPSLTSEGIRIYDTFAQFVIADLL

DDTRFLPMQSPPPNGLITFVNPSAYLADDIKNGNSHIVPGVQFYASDACTLIDIPHDLDTTS

VGLSVLHKFGKVDKDTLNKVLDRMLEQVSEDDGILQVYFDVERPRIDPVVVANTVFLFHLGK

RGHEVARSEKFVESVLLQRAYEEGTLYYNLGEAFLVSVARLVHEFKEHFTRSGMRRALEERL

RERARAGMQERDDALALAMRIRACALCGLAGEGLTKAAEQELLRLQCKSKGCWGCHPFYRNG

SNVLSWIGSEALTTAYAIAALQPIDI*

Amino acid sequence for mutant DfHAD-MOSmotif
(SEQ ID NO: 22)
MEFSASAPPPRLASVIILEPLGFLLTPHYSSQLPKKLLRRLLCTRIWHRYQRGRLRLRDAAM

LLAQLPFLAVSDHPWALDNLASLLRPTAVRAVPWMLLLLDFLRDELHLKVVCATNSSPEELQ

ELRHQFPALFAKVDATVSSGEEGVGKPSVRFLQAALDKAGVHAQQTLYLDSFDSLETIMAAR

SLGMHALSVEPCHIDELTARASSGQLRDAQLIRRIVCAMHGPAVSAVVSGSITSSGPQTAKI

EELPTAADSHLRSAALTSAQQFFLKVIAPHRPEKPFVQLPSLTSEGIRIYDTFAQFVIADLL

-continued

DDTRFLPMQSPPPNGLITFVNPSAYLADDIKNGNSHIVPGVQFYASDACTLIDIPHDLDTTS

VGLSVLHKFGKVDKDTLNKVLDRMLEQVSEDDGILQVAAAVERPRIDPVVVANTVFLFHLGK

RGHEVARSEKFVESVLLQRAYEEGTLYYNLGEAFLVSVARLVHEFKEHFTRSGMRRALEERL

RERARAGMQERDDALALAMRIRACALCGLAGEGLTKAAEQELLRLQCKSKGCWGCHPFYRNG

SNVLSWIGSEALTTAYAIAALQPIDI*

Alternative class II motif:
(SEQ ID NO: 23)
DLDTTS

Motif III:
(SEQ ID NO: 24)
QCKSKGCW

Motif IV:
(SEQ ID NO: 25)
DGILQVYFDVERPRIDPVVVAN

Modified Motif III:
(SEQ ID NO: 26)
QCAAAGCW

Modified Motif III:
(SEQ ID NO: 27)
QCEDGGW

Modified Motif IV:
(SEQ ID NO: 28)
DGILQVAAAVERPRIDPVVVAN

Modified class I motif mutated:
(SEQ ID NO: 29)
DSFDPLE

---

The invention claimed is:

1. An isolated polypeptide of the Haloacid dehalogenase-like (HAD-like) hydrolase superfamily, comprising terpene synthase activity, wherein said polypeptide is DfHAD comprising an amino acid sequence having at least 95% sequence identity to SEQ ID NO: 2 and retaining said terpene synthase activity;
   wherein said polypeptide comprises at least one non-naturally occurring modification relative to SEQ ID NO: 2.

2. The polypeptide of claim 1, comprising the ability to produce a drimane sesquiterpene, and/or a diphosphate derivative thereof.

3. The polypeptide of claim 2, comprising the ability to produce albicanyl diphosphate from farnesyl diphosphate (FPP) as substrate.

4. An isolated polypeptide which is a variant of DfHAD of claim 1, further comprising an amino acid substitution selected from the group consisting of:
   a. an amino acid substitution V274A in position 274 of SEQ ID NO:2; and
   b. an amino acid substitution K532R in position 532 of SEQ ID NO:2.

5. The polypeptide of claim 1 further comprising:
   a. a modified class I synthase motif as set forth in SEQ ID NO: 13 (DSFDSLE);
   b. a modified class II synthase motif as set forth in SEQ ID NO: 14 (HDLDT); and
   c. at least one further sequence motif selected from the group consisting of
      i. a partial sequence from position 86 to 195 of SEQ ID NO: 2; and
      ii. a partial sequence from position 40 to 187 of SEQ ID NO: 2.

6. A method for producing a drimane sesquiterpene comprising:
   a. contacting farnesyl diphosphate (FPP) with a polypeptide as defined in claim 1, thereby obtaining at least one diphosphate of drimane sesquiterpene;
   b. chemically or enzymatically cleaving the diphosphate moiety of said at least one diphosphate of drimane sesquiterpene; and
   c. optionally isolating the drimane sesquiterpene.

7. A method of producing (−)-(3aR,5aS,9aS,9bR)-3a,6,6,9a-tetramethyldodecahydronaphto[2,1-b]furan, which method comprises
   a. providing albicanol by a method as recited in claim 6,
   b. optionally isolating albicanol as produced in step a.; and
   c. converting albicanol to (−)-(3aR,5aS,9aS,9bR)-3a,6,6,9a-tetramethyldodecahydronaphto[2,1-b]furan.

8. The method of claim 6, wherein the drimane sesquiterpene is albicanol.

* * * * *